US010087436B2

(12) United States Patent
Li et al.

(10) Patent No.: US 10,087,436 B2
(45) Date of Patent: Oct. 2, 2018

(54) ELECTROPHYSIOLOGICALLY MATURE CARDIOMYOCYTES AND METHODS FOR MAKING SAME

(71) Applicant: The Regents of the University of California, Oakland, CA (US)

(72) Inventors: Ronald A. Li, Davis, CA (US); Deborah K. Lieu, Davis, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 14/615,291

(22) Filed: Feb. 5, 2015

(65) Prior Publication Data

US 2015/0218549 A1 Aug. 6, 2015

Related U.S. Application Data

(60) Provisional application No. 61/936,807, filed on Feb. 6, 2014.

(51) Int. Cl.
*A61K 35/34* (2015.01)
*C12N 13/00* (2006.01)

(52) U.S. Cl.
CPC .............. *C12N 13/00* (2013.01); *A61K 35/34* (2013.01)

(58) Field of Classification Search
None
See application file for complete search history.

(56) References Cited

U.S. PATENT DOCUMENTS

| | | | |
|---|---|---|---|
| 5,733,761 A | 3/1998 | Treco et al. | |
| 6,207,422 B1 | 3/2001 | Brown et al. | |
| 6,214,620 B1 | 4/2001 | Johns et al. | |
| 6,387,369 B1 | 5/2002 | Pittenger et al. | |
| 6,638,369 B1 | 10/2003 | Tucker et al. | |
| 6,686,198 B1 | 2/2004 | Melton et al. | |
| 7,202,080 B2 | 4/2007 | Ramiya et al. | |
| 9,045,731 B2 | 6/2015 | Li et al. | |
| 2004/0033943 A1 | 2/2004 | Strijbos et al. | |
| 2004/0254134 A1 | 12/2004 | Marban et al. | |
| 2005/0042254 A1 | 2/2005 | Freyman et al. | |
| 2005/0058633 A1 | 3/2005 | Epstein et al. | |
| 2005/0244377 A1 | 11/2005 | Sigg et al. | |
| 2006/0128647 A1 | 6/2006 | Sigg et al. | |
| 2007/0025972 A1 | 2/2007 | Rodriguez et al. | |
| 2007/0161107 A1 | 7/2007 | Mummery et al. | |
| 2008/0089874 A1 | 4/2008 | Li et al. | |
| 2012/0027807 A1 | 2/2012 | Chien et al. | |
| 2013/0040335 A1 | 2/2013 | Khine et al. | |
| 2014/0094388 A1 | 4/2014 | Wakatsuki | |
| 2016/0045555 A1 | 2/2016 | Li et al. | |

FOREIGN PATENT DOCUMENTS

| | | |
|---|---|---|
| WO | WO-00/18903 A2 | 4/2000 |
| WO | WO-02/19966 A2 | 3/2002 |
| WO | WO-02/08741 A2 | 11/2002 |
| WO | WO-2006/017566 A2 | 2/2006 |
| WO | WO-2006/017567 A2 | 2/2006 |
| WO | WO-2009/036220 A2 | 3/2009 |
| WO | WO-2009/152482 A2 | 12/2009 |
| WO | WO-2011/028579 A2 | 3/2011 |

OTHER PUBLICATIONS

Edelberg et al Enhancement of Murine Cardiac Chronotropy by the Molecular Transfer of the Human b2 Adrenergic Receptor cDNA J Clin Invest. 1998;101(2):337-343.*
Miake et al Nature. Sep. 12, 2002;419(6903):132-3.Biological pacemaker created by gene transfer.*
Yang et al Human cardiovascular progenitor cells develop from a KDR1 embryonic-stem-cell-derived population Nature 453, 524-528 (May 22, 2008).*
Au et al., Interactive effects of surface topography and pulsatile electrical field stimulation on orientation and elongation of fibroblasts and cardiomyocytes Biomaterials 28 (2007) 4277-4293.*
Radisic et al., Functional assembly of engineered myocardium by electrical stimulation of cardiac myocytes cultured on scaffoldsPNAS _ Dec. 28, 2004 _ vol. 101 _ No. 52 _ 18129-18134.*
Boheler et al Embryonic Stem Cell-Derived Cardiomyocyte Heterogeneity and the Isolation of Immature and Committed Cells for Cardiac Remodeling and Regeneration Stem Cells International vol. 2011 (2011), Article ID 214203, pp. 1-10.*
Halbach et al Electrophysiological Maturation and Integration of Murine Fetal Cardiomyocytes After Transplantation.*
Genetic Technologies Limited,Plaintiff-Appellant Merial L.L.C., Bristol-Myers Squibb Company Apr. 8, 2016 pp. 1-20.*
He et al., Human Embryonic Stem Cells Develop into multiple types of Cardiac Myocytes Circulation Research 2003; 32-39.*
Lieu et al Mechanism-Based Facilitated Maturation of Human Pluripotent Stem Cell-Derived Cardiomyocytes Circulation: Arrhythmia and Electrophysiology. Feb. 7, 2013 pp. 1-25.*
Xue et al Functional Integration of Electrically Active CardiacDerivatives From Genetically Engineered Human Embryonic Stem Cells With Quiescent Recipient Ventricular Cardiomyocytes Insights Into the Development of Cell-Based Pacemakers Circulation 2005 pp. 11-20.*
Wang et al. Stem Cells 23: 1526-34, 2005.*
Jiang et al Electrophysiological properties of human induced pluripotent stem cells American Journal of Physiology—Cell Physiology Published Feb. 24, 2010 vol. 298 No. 3, C486-C495.*
Liu et al., Functional Sarcoplasmic Reticulum for Calcium Handling of Humann Embryonic Stem Cell-Derived Cardiomyocytes: Insights for Driven Maturation Stem Cells 2007;25:3038-3044.*
Abraham, M.R. et al. (2005) "Antiarrhythmic engineering of skeletal myoblasts for cardiac transplantation," Circ. Res. 97(2):159-167.
U.S. Appl. No. 14/726,874, filed Jun. 1, 2015, The Regents of the University of California.
Accili, E.A. et al. (2002) "From Funny Current to HCN Channels: 20 Years of Excitation," News Physiol. Sci. 17:32-37.

(Continued)

Primary Examiner — Maria Gomez Leavitt
(74) Attorney, Agent, or Firm — Foley & Lardner LLP; Antoinette F. Konski; Erika Artinger

(57) ABSTRACT

Methods to prepare electrophysiology mature cells from immature cells are provided, without the need for genetic manipulation.

8 Claims, 18 Drawing Sheets

(56) References Cited

OTHER PUBLICATIONS

Alseikhan, B.A. et al. (2002) "Engineered calmodulins reveal the unexpected eminence of Ca(2+) channel inactivation in controlling heart excitation," Proc. Natl. Acad. Sci. USA 99:17185-17190.

Azene, E.M. et al. (2003) "Molecular basis of the effect of potassium on heterologously expressed pacemaker (HCN) channels," J. Physiol. 547:349-356.

Azene, E.M. et al. (2005) "Non-equilibrium behavior of HCN channels: Insights into the role of HCN channels in native and engineered pacemakers," Cardiovascular Research 67:263-273.

Azene, E.M. et al. (2005) "Pore-to-gate coupling of HCN channels revealed by a pore variant that contributes to gating but not permeation," Biochem. Biophys. Res. Commun. 327:1131-1142.

Baharvand, H. et al. (2005) "The effect of extracellular matrix on embryonic stem cell-derived cardiomyocytes," Journal of Molecular and Cellular Cardiology 38:495-503.

Baruscotti, M. et al. (2004) "Pacemaker Channels," Ann. N.Y. Acad. Sci. 1015:111-121.

Beqqali, A. et al. (2006) "Genome-Wide Transcriptional Profiling of Human Embryonic Stem Cells Differentiating to Cardiomyocytes," Stem Cells 24:1956-1967.

Boheler, K.R. et al. (2002) "Differentiation of Pluripotent Embryonic Stem Cells Into Cardiomyocytes," Circulation Research 91:189-201.

Boyett, M.R. et al. (1998) "Regional differences in effects of 4-aminopyridine within the sinoatrial node," Am. J. Physiol. 275 (Heart Circ. Physiol. 44):H1158-H1168.

Boyett, M.R. et al. (1999) "Downward gradient in action potential duration along conduction path in and around the sinoatrial node," Am. J. Physiol. 276:H686-H698.

Boyett, M.R. et al. (2000) "The sinoatrial node, a heterogeneous pacemaker structure," Cardiovascular Research 47:658-687.

Brown, A.M. (1990) "Regulation of heartbeat by G protein-coupled ion channels," American Journal of Physiology, Heart and Circulatory Physiology 259(6):H1621-H1628.

Bucchi, A.B. et al. (2006) "Wild-type and mutant HCN channels in a tandem biological-electronic cardiac pacemaker," Circulation 114:992-999.

Chan, Y-C. et al. (2010) "Automaticity and conduction properties of bio-artificial pacemakers assessed in an in vitro monolayer model of neonatal rat ventricular myocytes," Eurospace 12:1178-1187.

Cohen, I.S. et al. (2005) "The why, what, how and when of biological pacemakers," Nat. Clin. Pract. Cardiovasc. Med. 2(8):374-375.

DiFrancesco, D. (1993) "Pacemaker mechanisms in cardiac tissue," Annu. Rev. Physiol. 55:455-472.

Dolnikov, K. et al. (2005) "Functional properties of human embryonic stem cell-derived cardiomyocytes," Ann. N.Y. Acad. Sci. 1047:66-75.

Dolnikov, K. et al.(2006) "Functional Properties of Human Embryonic Stem Cell-Derived Cardiomyocytes: Intracellular Ca2 Handling and the Role of Sarcoplasmic Reticulum in the Contraction," Stem Cells 24:236-245.

Donahue, J.K. et al. (2000) "Focal modification of electrical conduction in the heart by viral gene transfer," Nature Medicine 6(12):1395-1398.

Donello, J.E. et al. (1998) "Woodchuck Hepatitis Virus Contains a Tripartite Posttranscriptional Regulatory Element," Journal of Virology 72(6):5085-5092.

Edelberg, J.M. et al. (1998) "Enhancement of Murine Cardiac Chronotropy by the Molecular Transfer of the Human β2 Andrenergic Receptor cDNA," J. Clin. Invest. 101(2):337-343.

El-Kholy, W. et al. (2007) "Hyperpolarizaton-Activated Cyclic Nucleotide-Gated Channels in Pancreatic β-Cells," Molecular Endocrinology 21(3):753-764.

Ennis, I.L. et al. (2002) "Dual gene therapy with SERCA1 and Kir2.1 abbreviates excitation without suppressing contractility," J. Clin. Invest. 109:393-400.

Er, F. et al. (2003) "Dominant-negative suppression of HCN channels markedly reduces the native pacemaker current If and undermines spontaneous beating of neonatal cardiomyocytes," Circulation 107:485-489.

Feld, Y. et al. (2002) "Electrophysiological Modulation of Cardiomyocytic Tissue by Transfected Fibroblasts Expressing Potassium Channels: A Novel Strategy to Manipulate Excitability," Circulation 105:522-529.

Fink, M. et al. (1996) "Dominant negative chimeras provide evidence for homo and heteromultimeric assembly of inward rectifier K+ channel proteins via their N-terminal end," FEBS Letters 378:64-68.

Friedman, B. et al. (1999) "A Comparison of the Pharmacological Properties of Carbohydrate Remodeled Recombinant and Placental-Derived β-Glucocerebrosidase: Implications for Clinical Efficacy in Treatment of Gaucher Disease," Blood 93(9):2807-2816.

Fu, J-D. (2005) "Crucial role of the sarcoplasmic reticulum in the developmental regulation of Ca2+ transients and contraction in cardiomyocytes derived from embryonic stem cells," The FASEB Journal 20(1):1-21.

Fu, J-D. et al. (2006) "Developmental regulation of intracellular calcium transients during cardiomyocyte differentiation of mouse embryonic stem cells," Acta Pharmacologica Sinica 27(7):901-910.

Gepstein, L. et al. (2004) "Somatic gene and cell therapy strategies for the treatment of cardiac arrhythmias," Am J Physiol Heart Circ Physiol. 286:815-822.

Gorza, L. et al. (1993) "Inositol 1,4,5-Trisphosphate Receptor in Heart: Evidence for its Concentration in Purkinje Myocytes of the Conduction System," The Journal of Cell Biology 121(2):345-353.

Graziani, A.T. et al. (2006) "Mechanisms underlying overdrive suppression and overdrive excitation in guinea pig sino-atrial node," Journal of Biomedical Science 13:703-720.

Hamill, O.P. et al. (1981) "Improved patch-clamp techniques for high-resolution current recording from cells and cell-free membrane patches," Pflügers Arch. 391:85-100.

Harth, G. et al. (1999) "Export of Recombinant *Mycobacterium tuberculosis* Superoxide Dismutase is Dependent upon Both Information in the Protein and Mycobacterial Export Machinery: A Model for Studying Export of Leaderless Proteins by Pathogenic Mycobacteria," The Journal of Biological Chemistry 274(7):4281-4292.

He, J-Q. et al. (2003) "Human Embryonic Stem Cells Develop Into Multiple Types of Cardiac Myocytes," Circ. Res. 93:32-39.

Henrikson, C.A. et al. (2003) "Identification of a surface charged residue in the S3-S4 linker of the pacemaker (HCN) channel that influences activation gating," The Journal of Biological Chemistry 278(16):13647-13654.

Hoppe, U.C. et al. (2000) "Adenovirus-mediated inducible gene expression in vivo by a hybrid ecdysone receptor," Molecular Therapy 1(2):159-164.

Huber, I. et al. (2007) "Identification and selection of cardiomyocytes during human embryonic stem cell differentiation," The FASEB Journal 21:2551-2563.

Ibarra, J. et al. (1991) "Dynamics of the inward rectifier K+ current during the action potential of guinea pig ventricular myocytes," Biophys. J. 60:1534-1539.

Kaplitt, M.G. et al. (1994) "Long-term gene expression and phenotypic correction using adeno-associated virus vectors in the mammalian brain," Nature Genetics 8:148-154.

Kapur, N. et al. (2007) "Inositol 1,4,5-trisphosphate-mediated spontaneous activity in mouse embryonic stem cell-derived cardiomyocytes," J Physiol. 581(3):1113-1127.

Kehat, I. et al. (2001) "Human embryonic stem cells can differentiate into myocytes with structural and functional properties of cardiomyocytes," J. Clin. Invest. 108:407-414.

Kiriazis, H. et al. (2000) "Genetically Engineered Models with Alterations in Cardiac Membrane Calcium-Handling Proteins," Annu. Rev. Physiol. 62:321-351.

Klein, R.L. et al. (1998) "Neuron-Specific Transduction in the Rat Septohippocampal or Nigrostriatal Pathway by Recombinant Adeno-associated Virus Vectors," Experimental Neurology 150:183-194.

(56) References Cited

OTHER PUBLICATIONS

Koban, M.U. et al. (1998) "Expressional analysis of the cardiac Na—Ca exchanger in rat development and senescence," Cardiovascular Research 37:405-423.

Kodama, I. et al. (1985) "Regional differences in the electrical activity of the rabbit sinus node," Pflügers Arch. 404:214-226.

Kodama, I. et al. (1997) "Regional differences in the role of the Ca2+ and Na+ currents in pacemaker activity in the sinoatrial node," Am. J. Physiol. 272 (Heart Circ. Physiol. 41):H2793-H2806.

Kolossov, E. et al. (1998) "Functional Characteristics of ES Cell-derived Cardiac Precursor Cells Identified by Tissue-specific Expression of the Green Fluorescent Protein," The Journal of Cell Biology 143(7):2045-2056.

Kumar, D. et al. (2005) "Embryonic stem cells: differentiation into cardiomyocytes and potential for heart repair and regeneration," Coronary Artery Disease 16:111-116.

Kurata, Y. et al. (2002) "Dynamical description of sinoatrial node pacemaking: improved mathematical model for primary pacemaker cell," Am. J. Physiol. Heart Circ. Physiol. 283:H2074-H2101.

Lesso, H. et al. (2003) "Helical secondary structure of the external S3-S4 linker of pacemaker (HCN) channels revealed by site-dependent perturbations of activation phenotype," The Journal of Biological Chemistry 278(25):22290-22297.

Li, J. et al. (2004) "Transgenic upregulation of IK1 in the mouse heart leads to multiple abnormalities of cardiac excitability," Am J Physiol Heart Circ Physiol. 287:H2790-H2802.

Li, R.A. et al. (2005) "Human embryonic stem cell-derived cardiomyocytes: therapeutic potentials and limitations," Journal of Stem Cells 1(2):109-124.

Li, R.K. et al. (1997) "Natural history of fetal rat cardiomyocytes transplanted into adult rat myocardial scar tissue," Circulation 96(9):II-179-186; discussion 186-187.

Liu, G.X. et al. (2001) "Comparison of cloned Kir2 channels with native inward rectifier K+ channels from guinea-pig cardiomyocytes," Journal of Physiology 532.1:115-126.

Liu, J. et al. (2007) "Functional Sarcoplasmic Reticulum for Calcium Handling of Human Embryonic Stem Cell-Derived Cardiomyocytes: Insights for Driven Maturation," Stem Cells 25:3038-3044.

Lopatin, A.N. (2002) "Inward rectification and cardiac excitability," Biologicheskie Membrany 19(1):57-65.

Lopatin, A.N. et al. (2000) "Modulation of potassium channels in the hearts of transgenic and mutant mice with altered polyamine biosynthesis," J. Mol. Cell Cardiol. 32:2007-2024.

Lubas, W.A. et al. (2000) "Functional Expression of O-linked GlcNAc Transferase," The Journal of Biological Chemistry 275(15):10983-10988.

Mandel, R.J. et al. (1998) "Characterization of Intrastriatal Recombinant Adeno-Associated Virus-Mediated Gene Transfer of Human Tyrosine Hydroxylase and Human GTP-Cyclohydrolase I in a Rat Model of Parkinson's Disease," The Journal of Neuroscience 18(11):4271-4284.

Miake, J. et al. (2002) "Biological pacemaker created by gene transfer," Nature 419:132-133.

Miake, J. et al. (2003) "Functional role of inward rectifier current in heart probed by Kir2.1 overexpression and dominant-negative suppression," J Clin Invest. 111(10):1529-1536.

Miller, S.L.W. et al. (2005) "Effects of calsequestrin overexpression on excitation-contraction coupling in isolated rabbit cardiomyocytes," Cardiovascular Research 67:667-677.

Mitra, R. et al. (1986) "Two types of calcium channels in guinea pig ventricular myocytes," Proc. Natl. Acad. Sci. USA 83:5340-5344.

Miyazaki, J. et al. (1989) "Expression vector system based on the chicken β-actin promoter directs efficient production of interleukin-5," Gene 79(2):269-277.

Moore, J.C. et al. (2005) "Human embryonic stem cells: Genetic manipulation on the way to cardiac cell therapies," Reproductive Toxicology 20:377-391.

Mummery, C. et al. (2002) "Differentiation of Human Embryonic Stem Cells to Cardiomyocytes," Circulation 107:2733-2740.

Nakamura, T.Y. et al. (1998) "Inhibition of rat ventricular IK1 with antisense oligonucleotides targeted to Kir2.1 mRNA," Am. J. Physiol. 274 (Heart Circ. Physiol. 43):H892-H900.

National Center for Biotechnology Information [online], GenBank Entrez CoreNucleotide Accession No. AB074970 [retrieved on Sep. 3, 2008] Retrieved from the internet: http://www.ncbi.nlm.nih.gov/entrez/viewer.fcgi?db=nuccore&id=21693121.

National Center for Biotechnology Information [online], GenBank Entrez CoreNucleotide Accession No. AB182123 [retrieved on Sep. 3, 2008] Retrieved from the internet: http://www.ncbi.nlm.nih.gov/entrez/viewer.fcgi?db=nuccore&id=48927625.

National Center for Biotechnology Information [online], GenBank Entrez CoreNucleotide Accession No. AF153819 [retrieved on Sep. 3, 2008] Retrieved from the internet: http://www.ncbi.nlm.nih.gov/entrez/viewer.fcgi?db=nuccore&id=8132300.

National Center for Biotechnology Information [online], GenBank Entrez CoreNucleotide Accession No. AF181988 [retrieved on Sep. 3, 2008] Retrieved from the internet: http://www.ncbi.nlm.nih.gov/entrez/viewer.fcgi?db=nuccore&id=9719053.

National Center for Biotechnology Information [online], GenBank Entrez CoreNucleotide Accession No. AF187964 [retrieved on Sep. 3, 2008] Retrieved from the internet: http://www.ncbi.nlm.nih.gov/entrez/viewer.fcgi?db=nuccore&id=6007796.

National Center for Biotechnology Information [online], GenBank Entrez CoreNucleotide Accession No. AF482710 [retrieved on Sep. 3, 2008] Retrieved from the internet: http://www.ncbi.nlm.nih.gov/entrez/viewer.fcgi?db=nuccore&id=19526413.

National Center for Biotechnology Information [online], GenBank Entrez CoreNucleotide Accession No. AF488549 [retrieved on Sep. 3, 2008] Retrieved from the internet: http://www.ncbi.nlm.nih.gov/entrez/viewer.fcgi?db=nuccore&id=28629105.

National Center for Biotechnology Information [online], GenBank Entrez CoreNucleotide Accession No. AF488550 [retrieved on Sep. 3, 2008] Retrieved from the internet: http://www.ncbi.nlm.nih.gov/entrez/viewer.fcgi?db=nuccore&id=28629107.

National Center for Biotechnology Information [online], GenBank Entrez CoreNucleotide Accession No. AJ010969 [retrieved on Sep. 3, 2008] Retrieved from the internet: http://www.ncbi.nlm.nih.gov/entrez/viewer.fcgi?db=nuccore&id=6006516.

National Center for Biotechnology Information [online], GenBank Entrez CoreNucleotide Accession No. AJ310887 [retrieved on Sep. 3, 2008] Retrieved from the internet: http://www.ncbi.nlm.nih.gov/entrez/viewer.fcgi?db=nuccore&id=18073678.

National Center for Biotechnology Information [online], GenBank Entrez CoreNucleotide Accession No. BC089439 [retrieved on Sep. 3, 2008] Retrieved from the internet: http://www.ncbi.nlm.nih.gov/entrez/viewer.fcgi?db=nuccore&id=58477273.

National Center for Biotechnology Information [online], GenBank Entrez CoreNucleotide Accession No. CH471051 [retrieved on Sep. 3, 2008] Retrieved from the internet: http://www.ncbi.nlm.nih.gov/entrez/viewer.fcgi?db=nuccore&id=74230054.

National Center for Biotechnology Information [online], GenBank Entrez CoreNucleotide Accession No. CH474029 [retrieved on Sep. 3, 2008] Retrieved from the internet: http://www.ncbi.nlm.nih.gov/entrez/viewer.fcgi?db=nuccore&id=71679471.

National Center for Biotechnology Information [online], GenBank Entrez CoreNucleotide Accession No. DQ023214 [retrieved on Sep. 3, 2008] Retrieved from the internet: http://www.ncbi.nlm.nih.gov/entrez/viewer.fcgi?db=nuccore&id=66735455.

National Center for Biotechnology Information [online], GenBank Entrez CoreNucleotide Accession No. EU107280 [retrieved on Sep. 3, 2008] Retrieved from the internet: http://www.ncbi.nlm.nih.gov/entrez/viewer.fcgi?db=nuccore&id=157142987.

National Center for Biotechnology Information [online], GenBank Entrez CoreNucleotide Accession No. NM_000165 [retrieved on Sep. 3, 2008] Retrieved from the internet: http://www.ncbi.nlm.nih.gov/entrez/viewer.fcgi?db=nuccore&id=122939163.

National Center for Biotechnology Information [online], GenBank Entrez CoreNucleotide Accession No. NM_000166 [retrieved on Sep. 3, 2008] Retrieved from the internet: http://www.ncbi.nlm.nih.gov/entrez/viewer.fcgi?db=nuccore&id=195222738.

National Center for Biotechnology Information [online], GenBank Entrez CoreNucleotide Accession No. NM_000218 [retrieved on

(56) References Cited

OTHER PUBLICATIONS

Sep. 3, 2008] Retrieved from the internet: http://www.ncbi.nlm.nih.gov/entrez/viewer.fcgi?db=nuccore&id=32479526.
National Center for Biotechnology Information [online], GenBank Entrez CoreNucleotide Accession No. NM_000363 [retrieved on Sep. 3, 2008] Retrieved from the internet: http://www.ncbi.nlm.nih.gov/entrez/viewer.fcgi?db=nuccore&id=151101269.
National Center for Biotechnology Information [online], GenBank Entrez CoreNucleotide Accession No. NM_000432 [retrieved on Sep. 3, 2008] Retrieved from the internet: http://www.ncbi.nlm.nih.gov/entrez/viewer.fcgi?db=nuccore&id=190358510.
National Center for Biotechnology Information [online], GenBank Entrez CoreNucleotide Accession No. NM_000719 [retrieved on Sep. 3, 2008] Retrieved from the internet: http://www.ncbi.nlm.nih.gov/entrez/viewer.fcgi?db=nuccore&id=193788716.
National Center for Biotechnology Information [online], GenBank Entrez CoreNucleotide Accession No. NM_000891 [retrieved on Sep. 3, 2008] Retrieved from the internet: http://www.ncbi.nlm.nih.gov/entrez/viewer.fcgi?db=nuccore&id=22095339.
National Center for Biotechnology Information [online], GenBank Entrez CoreNucleotide Accession No. NM_001001787 [retrieved on Sep. 3, 2008] Retrieved from the internet: http://www.ncbi.nlm.nih.gov/entrez/viewer.fcgi?db=nuccore&id=49574488.
National Center for Biotechnology Information [online], GenBank Entrez CoreNucleotide Accession No. NM_001018007 [retrieved on Sep. 3, 2008] Retrieved from the internet: http://www.ncbi.nlm.nih.gov/entrez/viewer.fcgi?db=nuccore&id=63252901.
National Center for Biotechnology Information [online], GenBank Entrez CoreNucleotide Accession No. NM_001024690 [retrieved on Sep. 3, 2008] Retrieved from the internet: http://www.ncbi.nlm.nih.gov/entrez/viewer.fcgi?db=nuccore&id=125991763.
National Center for Biotechnology Information [online], GenBank Entrez CoreNucleotide Accession No. NM_001039321 [retrieved on Sep. 3, 2008] Retrieved from the internet: http://www.ncbi.nlm.nih.gov/entrez/viewer.fcgi?db=nuccore&id=86129553.
National Center for Biotechnology Information [online], GenBank Entrez CoreNucleotide Accession No. NM_001102 [retrieved on Sep. 3, 2008] Retrieved from the internet: http://www.ncbi.nlm.nih.gov/entrez/viewer.fcgi?db=nuccore&id=194097348.
National Center for Biotechnology Information [online], GenBank Entrez CoreNucleotide Accession No. NM_001103 [retrieved on Sep. 3, 2008] Retrieved from the internet: http://www.ncbi.nlm.nih.gov/entrez/viewer.fcgi?db=nuccore&id=161377421.
National Center for Biotechnology Information [online], GenBank Entrez CoreNucleotide Accession No. NM_001194 [retrieved on Sep. 3, 2008] Retrieved from the internet: http://www.ncbi.nlm.nih.gov/entrez/viewer.fcgi?db=nuccore&id=156071469.
National Center for Biotechnology Information [online], GenBank Entrez CoreNucleotide Accession No. NM_002472 [retrieved on Sep. 3, 2008] Retrieved from the internet: http://www.ncbi.nlm.nih.gov/entrez/viewer.fcgi?db=nuccore&id=153945789.
National Center for Biotechnology Information [online], GenBank Entrez CoreNucleotide Accession No. NM_004004 [retrieved on Sep. 3, 2008] Retrieved from theinternet: http://www.ncbi.nlm.nih.gov/entrez/viewer.fcgi?db=nuccore&id=195539329.
National Center for Biotechnology Information [online], GenBank Entrez CoreNucleotide Accession No. NM_004924 [retrieved on Sep. 3, 2008] Retrieved from the internet: http://www.ncbi.nlm.nih.gov/entrez/viewer.fcgi?db=nuccore&id=34452697.
National Center for Biotechnology Information [online], GenBank Entrez CoreNucleotide Accession No. NM_004981 [retrieved on Sep. 3, 2008] Retrieved from the internet: http://www.ncbi.nlm.nih.gov/entrez/viewer.fcgi?db=nuccore&id=4826797.
National Center for Biotechnology Information [online], GenBank Entrez CoreNucleotide Accession No. NM_005267 [retrieved on Sep. 3, 2008] Retrieved from the internet: http://www.ncbi.nlm.nih.gov/entrez/viewer.fcgi?db=nuccore&id=55953075.
National Center for Biotechnology Information [online], GenBank Entrez CoreNucleotide Accession No. NM_005268 [retrieved on Sep. 3, 2008] Retrieved from the internet: http://www.ncbi.nlm.nih.gov/entrez/viewer.fcgi?db=nuccore&id=31542847.
National Center for Biotechnology Information [online], GenBank Entrez CoreNucleotide Accession No. NM_005477 [retrieved on Sep. 3, 2008] Retrieved from the internet: http://www.ncbi.nlm.nih.gov/entrez/viewer.fcgi?db=nuccore&id=4885406.
National Center for Biotechnology Information [online], GenBank Entrez CoreNucleotide Accession No. NM_005497 [retrieved on Sep. 3, 2008] Retrieved from the internet: http://www.ncbi.nlm.nih.gov/entrez/viewer.fcgi?db=nuccore&id=122939170.
National Center for Biotechnology Information [online], GenBank Entrez CoreNucleotide Accession No. NM_006783 [retrieved on Sep. 3, 2008] Retrieved from the internet: http://www.ncbi.nlm.nih.gov/entrez/viewer.fcgi?db=nuccore&id=194306613.
National Center for Biotechnology Information [online], GenBank Entrez CoreNucleotide Accession No. NM_010408 [retrieved on Sep. 3, 2008] Retrieved from the internet: http://www.ncbi.nlm.nih.gov/entrez/viewer.fcgi?db=nuccore&id=6754167.
National Center for Biotechnology Information [online], GenBank Entrez CoreNucleotide Accession No. NM_020660 [retrieved on Sep. 3, 2008] Retrieved from the internet: http://www.ncbi.nlm.nih.gov/entrez/viewer.fcgi?db=nuccore&id=10190697.
National Center for Biotechnology Information [online], GenBank Entrez CoreNucleotide Accession No. NM_020897 [retrieved on Sep. 3, 2008] Retrieved from the internet: http://www.ncbi.nlm.nih.gov/entrez/viewer.fcgi?db=nuccore&id=38327036.
National Center for Biotechnology Information [online], GenBank Entrez CoreNucleotide Accession No. NM_021012 [retrieved on Sep. 3, 2008] Retrieved from the internet: http://www.ncbi.nlm.nih.gov/entrez/viewer.fcgi?db=nuccore&id=118582281.
National Center for Biotechnology Information [online], GenBank Entrez CoreNucleotide Accession No. NM_021954 [retrieved on Sep. 3, 2008] Retrieved from the internet: http://www.ncbi.nlm.nih.gov/entrez/viewer.fcgi?db=nuccore&id=115392136.
National Center for Biotechnology Information [online], GenBank Entrez CoreNucleotide Accession No. NM_030772 [retrieved on Sep. 3, 2008] Retrieved from the internet: http://www.ncbi.nlm.nih.gov/entrez/viewer.fcgi?db=nuccore&id=62079290.
National Center for Biotechnology Information [online], GenBank Entrez CoreNucleotide Accession No. NM_053684 [retrieved on Sep. 3, 2008] Retrieved from the internet: http://www.ncbi.nlm.nih.gov/entrez/viewer.fcgi?db=nuccore&id=50878266.
National Center for Biotechnology Information [online], GenBank Entrez CoreNucleotide Accession No. NM_133497 [retrieved on Sep. 3, 2008] Retrieved from the internet: http://www.ncbi.nlm.nih.gov/entrez/viewer.fcgi?db=nuccore&id=28329446.
National Center for Biotechnology Information [online], GenBank Entrez CoreNucleotide Accession No. NM_152219 [retrieved on Sep. 3, 2008] Retrieved from the internet: http://www.ncbi.nlm.nih.gov/entrez/viewer.fcgi?db=nuccore&id=148839377.
National Center for Biotechnology Information [online], GenBank Entrez CoreNucleotide Accession No. NM_152263 [retrieved on Sep. 3, 2008] Retrieved from the internet: http://www.ncbi.nlm.nih.gov/entrez/viewer.fcgi?db=nuccore&id=114155139.
National Center for Biotechnology Information [online], GenBank Entrez CoreNucleotide Accession No. NM 152868 [retrieved on Sep. 3, 2008] Retrieved from the internet: http://www.ncbi.nlm.nih.gov/entrez/viewer.fcgi?db=nuccore&id=23110983.
National Center for Biotechnology Information [online], GenBank Entrez CoreNucleotide Accession No. NM_153212 [retrieved on Sep. 3, 2008] Retrieved from the internet: http://www.ncbi.nlm.nih.gov/entrez/viewer.fcgi?db=nuccore&id=23397463.
National Center for Biotechnology Information [online], GenBank Entrez CoreNucleotide Accession No. NM_153368 [retrieved on Sep. 3, 2008] Retrieved from the internet: http://www.ncbi.nlm.nih.gov/entrez/viewer.fcgi?db=nuccore&id=145699104.
National Center for Biotechnology Information [online], GenBank Entrez CoreNucleotide Accession No. NM_170720 [retrieved on Sep. 3, 2008] Retrieved from the internet: http://www.ncbi.nlm.nih.gov/entrez/viewer.fcgi?db=nuccore&id=25777634.
National Center for Biotechnology Information [online], GenBank Entrez CoreNucleotide Accession No. NM_181538 [retrieved on

(56) References Cited

OTHER PUBLICATIONS

Sep. 3, 2008] Retrieved from the internet: http://www.ncbi.nlm.nih.gov/entrez/viewer.fcgi?db=nuccore&id=31559820.
National Center for Biotechnology Information [online], GenBank Entrez CoreNucleotide Accession No. NM_198568 [retrieved on Sep. 3, 2008] Retrieved from the internet: http://www.ncbi.nlm.nih.gov/entrez/viewer.fcgi?db=nuccore&id=38348411.
National Center for Biotechnology Information [online], GenBank Entrez CoreNucleotide Accession No. NP_000354 [retrieved on Sep. 3, 2008] Retrieved from the internet: http://www.ncbi.nlm.nih.gov/entrez/viewer.fcgi?db=protein&id=151101270.
National Center for Biotechnology Information [online], GenBank Entrez CoreNucleotide Accession No. NP_066550 [retrieved on Sep. 3, 2008] Retrieved from the internet: http://www.ncbi.nlm.nih.gov/entrez/viewer.fcgi?db=protein&id=116325989.
National Center for Biotechnology Information [online], GenBank Entrez CoreNucleotide Accession No. X80417 [retrieved on Sep. 3, 2008] Retrieved from the internet: http://www.ncbi.nlm.nih.gov/entrez/viewer.fcgi?db=nuccore&id=550388.
National Center for Biotechnology Information [online], GenBank Entrez CoreNucleotide Accession No. Y13033 [retrieved on Sep. 3, 2008] Retrieved from the internet: http://www.ncbi.nlm.nih.gov/entrez/viewer.fcgi?db=nuccore&id=2463214.
National Center for Biotechnology Information [online], GenBank Entrez Protein Accession No. AAA36771 [retrieved on Sep. 3, 2008] Retrieved from the internet:: http://www.ncbi.nlm.nih.gov/entrez/viewer.fcgi?db=protein&id=339944.
National Center for Biotechnology Information [online], GenBank Entrez Protein Accession No. AAA59855 [retrieved on Sep. 3, 2008] Retrieved from the internet:: http://www.ncbi.nlm.nih.gov/entrez/viewer.fcgi?db=protein&id=188594.
National Center for Biotechnology Information [online], GenBank Entrez Protein Accession No. AAA59891 [retrieved on Sep. 3, 2008] Retrieved from the internet:: http://www.ncbi.nlm.nih.gov/entrez/viewer.fcgi?db=protein&id=189015.
National Center for Biotechnology Information [online], GenBank Entrez Protein Accession No. AAA59895 [retrieved on Sep. 3, 2008] Retrieved from the internet:: http://www.ncbi.nlm.nih.gov/entrez/viewer.fcgi?db=protein&id=189027.
National Center for Biotechnology Information [online], GenBank Entrez Protein Accession No. AAB59509 [retrieved on Sep. 3, 2008] Retrieved from the internet:: http://www.ncbi.nlm.nih.gov/entrez/viewer.fcgi?db=protein&id=339731.
National Center for Biotechnology Information [online], GenBank Entrez Protein Accession No. AAB91993 [retrieved on Sep. 3, 2008] Retrieved from the internet:: http://www.ncbi.nlm.nih.gov/entrez/viewer.fcgi?db=protein&id=2460247.
National Center for Biotechnology Information [online], GenBank Entrez Protein Accession No. AAD29948 [retrieved on Sep. 3, 2008] Retrieved from the internet: http://www.ncbi.nlm.nih.gov/entrez/viewer.fcgi?db=protein&id=4808809.
National Center for Biotechnology Information [online], GenBank Entrez Protein Accession No. AAF01045 [retrieved on Sep. 3, 2008] Retrieved from the internet: http://www.ncbi.nlm.nih.gov/entrez/viewer.fcgi?db=protein&id=6007797.
National Center for Biotechnology Information [online], GenBank Entrez Protein Accession No. AAF73241 [retrieved on Sep. 3, 2008] Retrieved from the internet: http://www.ncbi.nlm.nih.gov/entrez/viewer.fcgi?db=protein&id=8132297.
National Center for Biotechnology Information [online], GenBank Entrez Protein Accession No. AAF73242 [retrieved on Sep. 3, 2008] Retrieved from the internet: http://www.ncbi.nlm.nih.gov/entrez/viewer.fcgi?db=protein&id=8132301.
National Center for Biotechnology Information [online], GenBank Entrez Protein Accession No. AAF97619 [retrieved on Sep. 3, 2008] Retrieved from the internet: http://www.ncbi.nlm.nih.gov/entrez/viewer.fcgi?db=protein&id=9719054.
National Center for Biotechnology Information [online], GenBank Entrez Protein Accession No. AAH31006 [retrieved on Sep. 3, 2008] Retrieved from the internet: http://www.ncbi.nlm.nih.gov/entrez/viewer.fcgi?db=protein&id=21411329.
National Center for Biotechnology Information [online], GenBank Entrez Protein Accession No. AAH89439 [retrieved on Sep. 3, 2008] Retrieved from the internet: http://www.ncbi.nlm.nih.gov/entrez/viewer.fcgi?db=protein&id=58477274.
National Center for Biotechnology Information [online], GenBank Entrez Protein Accession No. AAI07534 [retrieved on Sep. 3, 2008] Retrieved from the internet: http://www.ncbi.nlm.nih.gov/entrez/viewer.fcgi?db=protein&id=77567675.
National Center for Biotechnology Information [online], GenBank Entrez Protein Accession No. AAL89708 [retrieved on Sep. 3, 2008] Retrieved from the internet: http://www.ncbi.nlm.nih.gov/entrez/viewer.fcgi?db=protein&id=19526414.
National Center for Biotechnology Information [online], GenBank Entrez Protein Accession No. AAO49469 [retrieved on Sep. 3, 2008] Retrieved from the internet: http://www.ncbi.nlm.nih.gov/entrez/viewer.fcgi?db=protein&id=28629106.
National Center for Biotechnology Information [online], GenBank Entrez Protein Accession No. AAO49470 [retrieved on Sep. 3, 2008] Retrieved from the internet: http://www.ncbi.nlm.nih.gov/entrez/viewer.fcgi?db=protein&id=28629108.
National Center for Biotechnology Information [online], GenBank Entrez Protein Accession No. AAY53910 [retrieved on Sep. 3, 2008] Retrieved from the internet: http://www.ncbi.nlm.nih.gov/entrez/viewer.fcgi?db=protein&id=66735456.
National Center for Biotechnology Information [online], GenBank Entrez Protein Accession No. ABC84220 [retrieved on Sep. 3, 2008] Retrieved from the internet: http://www.ncbi.nlm.nih.gov/entrez/viewer.fcgi?db=protein&id=85812161.
National Center for Biotechnology Information [online], GenBank Entrez Protein Accession No. ABR18779 [retrieved on Sep. 3, 2008] Retrieved from the internet: http://www.ncbi.nlm.nih.gov/entrez/viewer.fcgi?db=protein&id=148913210.
National Center for Biotechnology Information [online], GenBank Entrez Protein Accession No. ABV24476 [retrieved on Sep. 3, 2008] Retrieved from the internet: http://www.ncbi.nlm.nih.gov/entrez/viewer.fcgi?db=protein&id=157142988.
National Center for Biotechnology Information [online], GenBank Entrez Protein Accession No. BAC02718 [retrieved on Sep. 3, 2008] Retrieved from the internet: http://www.ncbi.nlm.nih.gov/entrez/viewer.fcgi?db=protein&id=21693122.
National Center for Biotechnology Information [online], GenBank Entrez Protein Accession No. BAD23901 [retrieved on Sep. 3, 2008] Retrieved from the internet: http://www.ncbi.nlm.nih.gov/entrez/viewer.fcgi?db=protein&id=48927626.
National Center for Biotechnology Information [online], GenBank Entrez Protein Accession No. CAA29119 [retrieved on Sep. 3, 2008] Retrieved from the internet: http://www.ncbi.nlm.nih.gov/entrez/viewer.fcgi?db=protein&id=34644.
National Center for Biotechnology Information [online], GenBank Entrez Protein Accession No. CAA37068 [retrieved on Sep. 3, 2008] Retrieved from the internet: http://www.ncbi.nlm.nih.gov/entrez/viewer.fcgi?db=protein&id=29727.
National Center for Biotechnology Information [online], GenBank Entrez Protein Accession No. CAA56622 [retrieved on Sep. 3, 2008] Retrieved from the internet: http://www.ncbi.nlm.nih.gov/entrez/viewer.fcgi?db=protein&id=550389.
National Center for Biotechnology Information [online], GenBank Entrez Protein Accession No. CAA73478 [retrieved on Sep. 3, 2008] Retrieved from the internet: http://www.ncbi.nlm.nih.gov/entrez/viewer.fcgi?db=protein&id=2463215.
National Center for Biotechnology Information [online], GenBank Entrez Protein Accession No. CAB56841 [retrieved on Sep. 3, 2008] Retrieved from the internet: http://www.ncbi.nlm.nih.gov/entrez/viewer.fcgi?db=protein&id=6006517.
National Center for Biotechnology Information [online], GenBank Entrez Protein Accession No. CAC70712 [retrieved on Sep. 3, 2008] Retrieved from the internet: http://www.ncbi.nlm.nih.gov/entrez/viewer.fcgi?db=protein&id=20338988.
National Center for Biotechnology Information [online], GenBank Entrez Protein Accession No. CAC70714 [retrieved on Sep. 3,

(56) References Cited

OTHER PUBLICATIONS

2008] Retrieved from the internet: http://www.ncbi.nlm.nih.gov/entrez/viewer.fcgi?db=protein&id=20338989.
National Center for Biotechnology Information [online], GenBank Entrez Protein Accession No. CAC84530 [retrieved on Sep. 3, 2008] Retrieved from the internet: http://www.ncbi.nlm.nih.gov/entrez/viewer.fcgi?db=protein&id=18073679.
National Center for Biotechnology Information [online], GenBank Entrez Protein Accession No. EAW48537 [retrieved on Sep. 3, 2008] Retrieved from the internet: http://www.ncbi.nlm.nih.gov/entrez/viewer.fcgi?db=protein&id=119568922.
National Center for Biotechnology Information [online], GenBank Entrez Protein Accession No. EDL89402 [retrieved on Sep. 3, 2008] Retrieved from the internet: http://www.ncbi.nlm.nih.gov/entrez/viewer.fcgi?db=protein&id=149034665.
National Center for Biotechnology Information [online], GenBank Entrez Protein Accession No. NP_000156 [retrieved on Sep. 3, 2008] Retrieved from the internet: http://www.ncbi.nlm.nih.gov/entrez/viewer.fcgi?db=protein&id=4504001.
National Center for Biotechnology Information [online], GenBank Entrez Protein Accession No. NP_000157 [retrieved on Sep. 3, 2008] Retrieved from the internet: http://www.ncbi.nlm.nih.gov/entrez/viewer.fcgi?db=protein&id=4504005.
National Center for Biotechnology Information [online], GenBank Entrez Protein Accession No. NP_000209 [retrieved on Sep. 3, 2008] Retrieved from the internet: http://www.ncbi.nlm.nih.gov/entrez/viewer.fcgi?db=protein&id=32479527.
National Center for Biotechnology Information [online], GenBank Entrez Protein Accession No. NP_000248 [retrieved on Sep. 3, 2008] Retrieved from the internet: http://www.ncbi.nlm.nih.gov/entrez/viewer.fcgi?db=protein&id=115496169.
National Center for Biotechnology Information [online], GenBank Entrez Protein Accession No. NP_000423 [retrieved on Sep. 3, 2008] Retrieved from the internet: http://www.ncbi.nlm.nih.gov/entrez/viewer.fcgi?db=protein&id=94981553.
National Center for Biotechnology Information [online], GenBank Entrez Protein Accession No. NP_000710 [retrieved on Sep. 3, 2008] Retrieved from the internet: http://www.ncbi.nlm.nih.gov/entrez/viewer.fcgi?db=protein&id=120433602.
National Center for Biotechnology Information [online], GenBank Entrez Protein Accession No. NP_000882 [retrieved on Sep. 3, 2008] Retrieved from the internet: http://www.ncbi.nlm.nih.gov/entrez/viewer.fcgi?db=protein&id=4504835.
National Center for Biotechnology Information [online], GenBank Entrez Protein Accession No. NP_001001430 [retrieved on Sep. 3, 2008] Retrieved from the internet: http://www.ncbi.nlm.nih.gov/entrez/viewer.fcgi?db=protein&id=48255879.
National Center for Biotechnology Information [online], GenBank Entrez Protein Accession No. NP_001001787 [retrieved on Sep. 3, 2008] Retrieved from the internet: http://www.ncbi.nlm.nih.gov/entrez/viewer.fcgi?db=protein&id=49574489.
National Center for Biotechnology Information [online], GenBank Entrez Protein Accession No. NP_001005752 [retrieved on Sep. 3, 2008] Retrieved from the internet: http://www.ncbi.nlm.nih.gov/entrez/viewer.fcgi?db=protein&id=54607056.
National Center for Biotechnology Information [online], GenBank Entrez Protein Accession No. NP_001018007 [retrieved on Sep. 3, 2008] Retrieved from the internet: http://www.ncbi.nlm.nih.gov/entrez/viewer.fcgi?db=protein&id=63252902.
National Center for Biotechnology Information [online], GenBank Entrez Protein Accession No. NP_001019861 [retrieved on Sep. 3, 2008] Retrieved from the internet: http://www.ncbi.nlm.nih.gov/entrez/viewer.fcgi?db=protein&id=125991764.
National Center for Biotechnology Information [online], GenBank Entrez Protein Accession No. NP_001029807 [retrieved on Sep. 3, 2008] Retrieved from the internet: http://www.ncbi.nlm.nih.gov/entrez/viewer.fcgi?db=protein&id=77736221.
National Center for Biotechnology Information [online], GenBank Entrez Protein Accession No. NP_001034410 [retrieved on Sep. 3, 2008] Retrieved from the internet: http://www.ncbi.nlm.nih.gov/entrez/viewer.fcgi?db=protein&id=86129554.
National Center for Biotechnology Information [online], GenBank Entrez Protein Accession No. NP_001093 [retrieved on Sep. 3, 2008] Retrieved from the internet: http://www.ncbi.nlm.nih.gov/entrez/viewer.fcgi?db=protein&id=4501891.
National Center for Biotechnology Information [online], GenBank Entrez Protein Accession No. NP_001094 [retrieved on Sep. 3, 2008] Retrieved from the internet: http://www.ncbi.nlm.nih.gov/entrez/viewer.fcgi?db=protein&id=4501893.
National Center for Biotechnology Information [online], GenBank Entrez Protein Accession No. NP_001095 [retrieved on Sep. 3, 2008] Retrieved from the internet: http://www.ncbi.nlm.nih.gov/entrez/viewer.fcgi?db=protein&id=4557241.
National Center for Biotechnology Information [online], GenBank Entrez Protein Accession No. NP_001185 [retrieved on Sep. 3, 2008] Retrieved from the internet: http://www.ncbi.nlm.nih.gov/entrez/viewer.fcgi?db=protein&id=156071470.
National Center for Biotechnology Information [online], GenBank Entrez Protein Accession No. NP_003272 [retrieved on Sep. 3, 2008] Retrieved from the internet: http://www.ncbi.nlm.nih.gov/entrez/viewer.fcgi?db=protein&id=56682969.
National Center for Biotechnology Information [online], GenBank Entrez Protein Accession No. NP_003995 [retrieved on Sep. 3, 2008] Retrieved from the internet: http://www.ncbi.nlm.nih.gov/entrez/viewer.fcgi?db=protein&id=42558283.
National Center for Biotechnology Information [online], GenBank Entrez Protein Accession No. NP_004915 [retrieved on Sep. 3, 2008] Retrieved from the internet: http://www.ncbi.nlm.nih.gov/entrez/viewer.fcgi?db=protein&id=12025678.
National Center for Biotechnology Information [online], GenBank Entrez Protein Accession No. NP_004972 [retrieved on Sep. 3, 2008] Retrieved from the internet: http://www.ncbi.nlm.nih.gov/entrez/viewer.fcgi?db=protein&id=4826798.
National Center for Biotechnology Information [online], GenBank Entrez Protein Accession No. NP_005258 [retrieved on Sep. 3, 2008] Retrieved from the internet: http://www.ncbi.nlm.nih.gov/entrez/viewer.fcgi?db=protein&id=55953076.
National Center for Biotechnology Information [online], GenBank Entrez Protein Accession No. NP_005259 [retrieved on Sep. 3, 2008] Retrieved from the internet: http://www.ncbi.nlm.nih.gov/entrez/viewer.fcgi?db=protein&id=10835079.
National Center for Biotechnology Information [online], GenBank Entrez Protein Accession No. NP_005468 [retrieved on Sep. 3, 2008] Retrieved from the internet: http://www.ncbi.nlm.nih.gov/entrez/viewer.fcgi?db=protein&id=4885407.
National Center for Biotechnology Information [online], GenBank Entrez Protein Accession No. NP_005488 [retrieved on Sep. 3, 2008] Retrieved from the internet: http://www.ncbi.nlm.nih.gov/entrez/viewer.fcgi?db=protein&id=69122473.
National Center for Biotechnology Information [online], GenBank Entrez Protein Accession No. NP_006774 [retrieved on Sep. 3, 2008] Retrieved from the internet: http://www.ncbi.nlm.nih.gov/entrez/viewer.fcgi?db=protein&id=40254837.
National Center for Biotechnology Information [online], GenBank Entrez Protein Accession No. NP_065711 [retrieved on Sep. 3, 2008] Retrieved from the internet: http://www.ncbi.nlm.nih.gov/entrez/viewer.fcgi?db=protein&id=10190698.
National Center for Biotechnology Information [online], GenBank Entrez Protein Accession No. NP_065948 [retrieved on Sep. 3, 2008] Retrieved from the internet: http://www.ncbi.nlm.nih.gov/entrez/viewer.fcgi?db=protein&id=38327037.
National Center for Biotechnology Information [online], GenBank Entrez Protein Accession No. NP_066292 [retrieved on Sep. 3, 2008] Retrieved from the internet: http://www.ncbi.nlm.nih.gov/entrez/viewer.fcgi?db=protein&id=23110982.
National Center for Biotechnology Information [online], GenBank Entrez Protein Accession No. NP_068773 [retrieved on Sep. 3, 2008] Retrieved from the internet: http://www.ncbi.nlm.nih.gov/entrez/viewer.fcgi?db=protein&id=22779877.
National Center for Biotechnology Information [online], GenBank Entrez Protein Accession No. NP_110399 [retrieved on Sep. 3,

(56) References Cited

OTHER PUBLICATIONS

2008] Retrieved from the internet: http://www.ncbi.nlm.nih.gov/entrez/viewer.fcgi?db=protein&id=31542845.
National Center for Biotechnology Information [online], GenBank Entrez Protein Accession No. NP_112267 [retrieved on Sep. 3, 2008] Retrieved from the internet: http://www.ncbi.nlm.nih.gov/entrez/viewer.fcgi?db=protein&id=13591902.
National Center for Biotechnology Information [online], GenBank Entrez Protein Accession No. NP_445827 [retrieved on Sep. 3, 2008] Retrieved from the internet: http://www.ncbi.nlm.nih.gov/entrez/viewer.fcgi?db=protein&id=16758108.
National Center for Biotechnology Information [online], GenBank Entrez Protein Accession No. NP_446136 [retrieved on Sep. 3, 2008] Retrieved from the internet: http://www.ncbi.nlm.nih.gov/entrez/viewer.fcgi?db=protein&id=50878267.
National Center for Biotechnology Information [online], GenBank Entrez Protein Accession No. NP_598004 [retrieved on Sep. 3, 2008] Retrieved from the internet: http://www.ncbi.nlm.nih.gov/entrez/viewer.fcgi?db=protein&id=19424136.
National Center for Biotechnology Information [online], GenBank Entrez Protein Accession No. NP_598917 [retrieved on Sep. 3, 2008] Retrieved from the internet: http://www.ncbi.nlm.nih.gov/entrez/viewer.fcgi?db=protein&id=61097906.
National Center for Biotechnology Information [online], GenBank Entrez Protein Accession No. NP_609903 [retrieved on Sep. 3, 2008] Retrieved from the internet: http://www.ncbi.nlm.nih.gov/entrez/viewer.fcgi?db=protein&id=62484243.
National Center for Biotechnology Information [online], GenBank Entrez Protein Accession No. NP_689343 [retrieved on Sep. 3, 2008] Retrieved from the internet: http://www.ncbi.nlm.nih.gov/entrez/viewer.fcgi?db=protein&id=148839378.
National Center for Biotechnology Information [online], GenBank Entrez Protein Accession No. NP_690607 [retrieved on Sep. 3, 2008] Retrieved from the internet: http://www.ncbi.nlm.nih.gov/entrez/viewer.fcgi?db=protein&id=23110984.
National Center for Biotechnology Information [online], GenBank Entrez Protein Accession No. NP_694944 [retrieved on Sep. 3, 2008] Retrieved from the internet: http://www.ncbi.nlm.nih.gov/entrez/viewer.fcgi?db=protein&id=23397464.
National Center for Biotechnology Information [online], GenBank Entrez Protein Accession No. NP_699199 [retrieved on Sep. 3, 2008] Retrieved from the internet: http://www.ncbi.nlm.nih.gov/entrez/viewer.fcgi?db=protein&id=145699105.
National Center for Biotechnology Information [online], GenBank Entrez Protein Accession No. NP_733838 [retrieved on Sep. 3, 2008] Retrieved from the internet: http://www.ncbi.nlm.nih.gov/entrez/viewer.fcgi?db=protein&id=25777635.
National Center for Biotechnology Information [online], GenBank Entrez Protein Accession No. NP_853516 [retrieved on Sep. 3, 2008] Retrieved from the internet: http://www.ncbi.nlm.nih.gov/entrez/viewer.fcgi?db=protein&id=31559821.
National Center for Biotechnology Information [online], GenBank Entrez Protein Accession No. NP_940970 [retrieved on Sep. 3, 2008] Retrieved from the internet: http://www.ncbi.nlm.nih.gov/entrez/viewer.fcgi?db=protein&id=38348412.
National Center for Biotechnology Information [online], GenBank Entrez Protein Accession No. O18839 [retrieved on Sep. 3, 2008] Retrieved from the internet: http://www.ncbi.nlm.nih.gov/entrez/viewer.fcgi?db=protein&id=3024031.
National Center for Biotechnology Information [online], GenBank Entrez Protein Accession No. O19182 [retrieved on Sep. 3, 2008] Retrieved from the internet: http://www.ncbi.nlm.nih.gov/entrez/viewer.fcgi?db=protein&id=9910716.
National Center for Biotechnology Information [online], GenBank Entrez Protein Accession No. O70596 [retrieved on Sep. 3, 2008] Retrieved from the internet: http://www.ncbi.nlm.nih.gov/entrez/viewer.fcgi?db=protein&id=54036089.
National Center for Biotechnology Information [online], GenBank Entrez Protein Accession No. O75712 [retrieved on Sep. 3, 2008] Retrieved from the internet: http://www.ncbi.nlm.nih.gov/entrez/viewer.fcgi?db=protein&id=6014758.
National Center for Biotechnology Information [online], GenBank Entrez Protein Accession No. P08034 [retrieved on Sep. 3, 2008] Retrieved from the internet: http://www.ncbi.nlm.nih.gov/entrez/viewer.fcgi?db=protein&id=117688.
National Center for Biotechnology Information [online], GenBank Entrez Protein Accession No. P12883 [retrieved on Sep. 3, 2008] Retrieved from the internet: http://www.ncbi.nlm.nih.gov/entrez/viewer.fcgi?db=protein&id=83304912.
National Center for Biotechnology Information [online], GenBank Entrez Protein Accession No. P13533 [retrieved on Sep. 3, 2008] Retrieved from the internet: http://www.ncbi.nlm.nih.gov/entrez/viewer.fcgi?db=protein&id=3041706.
National Center for Biotechnology Information [online], GenBank Entrez Protein Accession No. P19429 [retrieved on Sep. 3, 2008] Retrieved from the internet: http://www.ncbi.nlm.nih.gov/entrez/viewer.fcgi?db=protein&id=136213.
National Center for Biotechnology Information [online], GenBank Entrez Protein Accession No. P35561 [retrieved on Sep. 3, 2008] Retrieved from the internet: http://www.ncbi.nlm.nih.gov/entrez/viewer.fcgi?db=protein&id=547735.
National Center for Biotechnology Information [online], GenBank Entrez Protein Accession No. P35609 [retrieved on Sep. 3, 2008] Retrieved from the internet: http://www.ncbi.nlm.nih.gov/entrez/viewer.fcgi?db=protein&id=543742.
National Center for Biotechnology Information [online], GenBank Entrez Protein Accession No. P49656 [retrieved on Sep. 3, 2008] Retrieved from the internet: http://www.ncbi.nlm.nih.gov/entrez/viewer.fcgi?db=protein&id=1352481.
National Center for Biotechnology Information [online], GenBank Entrez Protein Accession No. P52185 [retrieved on Sep. 3, 2008] Retrieved from the internet: http://www.ncbi.nlm.nih.gov/entrez/viewer.fcgi?db=protein&id=1708549.
National Center for Biotechnology Information [online], GenBank Entrez Protein Accession No. P52187 [retrieved on Sep. 3, 2008] Retrieved from the internet: http://www.ncbi.nlm.nih.gov/entrez/viewer.fcgi?db=protein&id=1708554.
National Center for Biotechnology Information [online], GenBank Entrez Protein Accession No. P52188 [retrieved on Sep. 3, 2008] Retrieved from the internet: http://www.ncbi.nlm.nih.gov/entrez/viewer.fcgi?db=protein&id=1708555.
National Center for Biotechnology Information [online], GenBank Entrez Protein Accession No. P52189 [retrieved on Sep. 3, 2008] Retrieved from the internet: http://www.ncbi.nlm.nih.gov/entrez/viewer.fcgi?db=protein&id=1708551.
National Center for Biotechnology Information [online], GenBank Entrez Protein Accession No. P52190 [retrieved on Sep. 3, 2008] Retrieved from the internet: http://www.ncbi.nlm.nih.gov/entrez/viewer.fcgi?db=protein&id=1708552.
National Center for Biotechnology Information [online], GenBank Entrez Protein Accession No. P63252 [retrieved on Sep. 3, 2008] Retrieved from the internet: http://www.ncbi.nlm.nih.gov/entrez/viewer.fcgi?db=protein&id=54037433.
National Center for Biotechnology Information [online], GenBank Entrez Protein Accession No. Q14500 [retrieved on Sep. 3, 2008] Retrieved from the internet: http://www.ncbi.nlm.nih.gov/entrez/viewer.fcgi?db=protein&id=77416868.
National Center for Biotechnology Information [online], GenBank Entrez Protein Accession No. Q5T442 [retrieved on Sep. 3, 2008] Retrieved from the internet: http://www.ncbi.nlm.nih.gov/entrez/viewer.fcgi?db=protein&id=74744875.
National Center for Biotechnology Information [online], GenBank Entrez Protein Accession No. Q64198 [retrieved on Sep. 3, 2008] Retrieved from the internet: http://www.ncbi.nlm.nih.gov/entrez/viewer.fcgi?db=protein&id=2493598.
National Center for Biotechnology Information [online], GenBank Entrez Protein Accession No. Q64273 [retrieved on Sep. 3, 2008] Retrieved from the internet: http://www.ncbi.nlm.nih.gov/entrez/viewer.fcgi?db=protein&id=2493597.
National Center for Biotechnology Information [online], GenBank Entrez Protein Accession No. Q6PEY0 [retrieved on Sep. 3, 2008]

(56) References Cited

OTHER PUBLICATIONS

Retrieved from the internet: http://www.ncbi.nlm.nih.gov/entrez/viewer.fcgi?db=protein&id=74749171.
National Center for Biotechnology Information [online], GenBank Entrez Protein Accession No. Q8JZN3 [retrieved on Sep. 3, 2008] Retrieved from the internet: http://www.ncbi.nlm.nih.gov/entrez/viewer.fcgi?db=protein&id=54036145.
National Center for Biotechnology Information [online], GenBank Entrez Protein Accession No. Q9UL51 [retrieved on Sep. 3, 2008] Retrieved from the internet: http://www.ncbi.nlm.nih.gov/entrez/viewer.fcgi?db=protein&id=108935843.
Parton, R.G. et al. (1997) "Caveolin-3 Associates with Developing T-tubules during Muscle Differentiation," The Journal of Cell Biology 136(1):137-154.
Plaster, N.M. et al. (2001) "Mutations in Kir2.1 Cause the Developmental and Episodic Electrical Phenotypes of Andersen's Syndrome," Cell 105:511-519.
Proenza, C. et al. (2002) "Pacemaker channels produce an instantaneous current," Journal of Biological Chemistry 277(7): 5101-5109.
Qu, J. et al. (2001) "HCN2 Overexpression in Newborn and Adult Ventricular Myocytes: Distinct Effects on Gating and Excitability," Circulation Research 89:e8-e14.
Qu, J. et al. (2003) "Expression and Function of a Biological Pacemaker in Canine Heart," Circulation 107:1106-1109.
Sartiani, L. et al. (2007) "Developmental Changes in Cardiomyocytes Differentiated from Human Embryonic Stem Cells: A Molecular and Electrophysiological Approach," Stem Cells 25:1136-1144.
Satin, J. et al. (2004) "Mechanism of spontaneous excitability in human embryonic stem cell derived cardiomyocytes," J Physiol. 559(2):479-496.
Satoh, H. (2003) "Sino-Atrial Nodal Cells of Mammalian Hearts: Ionic Currents and Gene Expression of Pacemaker Ionic Channels," J. Smooth Muscle Res. 39(5):175-193.
Sauer, H. et al. (2001) "Characteristics of calcium sparks in cardiomyocytes derived from embryonic stem cells," Am J Physiol Heart Cir Physiol. 281:H411-H421.
Schram, G. et al. (2002) "Differential Distribution of Cardiac Ion Channel Expression as a Basis for Regional Specialization in Electrical Function," Circulation Research 90:939-950.
Sekar, R.B. et al. (2007) "Lentiviral vector-mediated expression of GFP or Kir2.1 alters the electrophysiology of neonatal rat ventricular myocytes without inducing cytotoxicity," Am J Physiol Heart Circ Physiol 293:H2757-H2770.
Shi, W. et al. (1999) "Distribution and Prevalence of Hyperpolarization-Activated Cation Channel (HCN) mRNA Expression in Cardiac Tissues," Circulation Research 85:e1-e6.
Shipley, J.M. et al. (1991) "Analysis of the 5′ Flanking Region of the Human β-Glucuronidase Gene," Genomics 10:1009-1018.
Siu, C.W. et al. (2006) "HCN-Encoded Pacemaker Channels: From Physiology and Biophysics to Bioengineering," J. Membrane Biol. 214(3):115-122.
Siu, C.W. et al. (2007) "Human Embryonic Stem Cell-Derived Cardiomyocytes for Heart Therapies," Cardiovascular & Haematological Disorders-Drug Targets 7(2):145-152.
Smits, P.C. (2004) "Myocardial repair with autologous skeletal myoblasts: a review of the clinical studies and problems," Minerva Cardioangiol. 52:525-535.
Sobey, C.G. et al. (2000) "Knockout Blow for Channel Identity Crisis, Vasodilation to Potassium is Mediated via Kir2.1," Circulation Research 87:83-84.
Terentyev, D. et al. (2003) "Calsequestrin determines the functional size and stability of cardiac intracellular calcium stores: Mechanism for hereditary arrhythmia," PNAS 100(20):11759-11764.
Tomita, Y. et al. (2007) "Application of mesenchymal stem cell-derived cardiomyocytes as bio-pacemakers: current status and problems to be solved," Med. Bio. Eng. Comput. 45:209-220.
Tsang, S.Y. et al. (2004) "Critical intra-linker interactions of HCN1-encoded pacemaker channels revealed by interchange of S3-S4 determinants," Biochem. Biophys. Res. Commun. 322:652-658.
Tsang, S.Y. et al. (2004) "Dissecting the Structural and Functional Roles of the S3-S4 Linker of Pacemaker (HCN) Channels by Systematic Length Alterations," The Journal of Biological Chemistry 279(42):43752-43759.
Tse, H-F. et al. (2006) "Bioartificial Sinus Node Constructed via in Vivo Gene Transfer of an Engineered Pacemaker HCN Channel Reduces the Dependence on Electronic Pacemaker in a Sick-Sinus Syndrome Model," Circulation 114:1000-1011.
Tse, H-F. et al. (2009) "Synergistic effects of Inward Rectifier (IK1) and Pacemaker (If) Currents on the Induction of Bioengineered Cardiac Automaticity," J Cardiovasc Electrophysiol. 20(9):1048-1054.
Vinogradova, T.M. et al. (2005) "Rhythmic Ca2+ Oscillations Drive Sinoatrial Nodal Cell Pacemaker Function to Make the Heart Tick," Ann. N.Y. Acad. Sci. 1047:138-156.
Wainger, B.J. et al. (2001) "Molecular mechanism of cAMP modulation of HCN pacemaker channels," Nature 411:805-810.
Wang, K.W. et al. (2005) "Electrophysiological Properties of Pluripotent Human and Mouse Embryonic Stem Cells," Stem Cells 23(10):1526-1534.
Watanabe, E-I. et al. (1996) "Inactivation of the calcium current is involved in overdrive suppression of rabbit sinoatrial node cells," Am. J. Physiol. Heart Circ. Physiol. 271 (Heart Circ. Physiol. 40):H2097-H2107.
Wellner-Kienitz, M-C. et al. (2004) "Voltage dependence of ATP-dependent K(+) current in rat cardiac myocytes is affected by I[K1] and 1[K(ACh)]," J Physiol 561.2:459-469.
Wilson, J.M. et al. (1990) "Expression of human adenosine deaminase in mice reconstituted with retrovirus-transduced hematopoietic stem cells," Proc. Natl. Acad. Sci. USA 87:439-443.
Wobus, A.M. et al. (2002) "Embryonic stem cells as a model to study cardiac, skeletal muscle, and vascular smooth muscle cell differentiation," Methods in Molecular Biology 185:127-156.
Xu, C. et al. (2002) "Characterization and Enrichment of Cardiomyocytes Derived From Human Embryonic Stem Cells," Circulation Research 91:501-508.
Xu, R. et al. (2001) "Quantitative comparison of expression with adeno-associated virus (AAV-2) brain-specific gene cassettes," Gene Therapy 8:1323-1332.
Xue et al. (2005) "Functional integration of electrically active cardiac derivatives from genetically engineered human embryonic stem cells with quiescent recipient ventricular cardiomyocytes: insights into the development of cell-based pacemakers" Circulation 111(1):11-20.
Xue, T. et al. (2002) "An external determinant in the S5-P linker of the pacemaker (HCN) channel identified by sulfhydryl modification," The Journal of Biological Chemistry 277(48):46233-46242.
Xue, T. et al. (2002) "Dominant-Negative Suppression of HCN1- and HCN2-Encoded Pacemaker Currents by an Engineered HCN1 Construct: Insights Into Structure-Function Relationships and Multimerization," Circulation Research 90:1267-1273.
Xue, T. et al. (2005) "Functional Integration of Electrically Active Cardiac Derivatives From Genetically Engineered Human Embryonic Stem Cells With Quiescent Recipient Ventricular Cardiomyocytes," Circulation 111:11-20.
Xue, T. et al. (2007) "Mechanistic role of If revealed by induction of ventricular automaticity by somatic gene transfer of gating-engineered pacemaker (HCN) channels," Circulation 115:1839-1850.
Yang, H-T. et al. (2002) "The ryanodine receptor modulates the spontaneous beating rate of cardiomyocytes during development," PNAS 99(14):9225-9230.
Yu, H. et al. (1993) "Pacemaker Current Exists in Ventricular Myocytes," Circulation Research 72:232-236.
Zaritsky, J.J. et al. (2000) "Targeted Disruption of Kir2.1 and Kir2.2 Genes Reveals the Essential Role of the Inwardly Rectifying K+ Current in K+-Mediated Vasodilation," Circulation Research 87:160-166.
Zaritsky, J.J. et al. (2001) "The consequences of disrupting cardiac inwardly rectifying K+ current (IK1) as revealed by the targeted deletion of the murine Kir2.1 and Kir2.2 genes," Journal of Physiology 533.3:697-710.

(56) References Cited

OTHER PUBLICATIONS

Zhang, Y.M. et al. (2002) "Stem cell-derived cardiomyocytes demonstrate arrhythmic potential," Circulation 106:1294-1299.
Restriction Requirement in U.S. Appl. No. 11/864,755, dated Apr. 1, 2010.
Non-Final Office Action in U.S. Appl. No. 11/864,755, dated Sep. 17, 2010.
Final Office Action in U.S. Appl. No. 11/864,755, dated Jan. 31, 2013.
Non-Final Office Action in U.S. Appl. No. 11/864,755, dated Mar. 11, 2014.
Final Office Action in U.S. Appl. No. 11/864,755, dated Sep. 26, 2014.
Non-Final Office Action in U.S. Appl. No. 11/864,755, dated Mar. 12, 2015.
Final Office Action in U.S. Appl. No. 11/864,755, dated Dec. 31, 2015.
Restriction Requirement in U.S. Appl. No. 12/677,790, dated Feb. 27, 2012.
Non-Final Office Action in U.S. Appl. No. 12/677,790, dated Aug. 30, 2012.
Final Office Action in U.S. Appl. No. 12/677,790, dated Apr. 25, 2013.
Notice of Allowance in U.S. Appl. No. 12/677,790, dated Jan. 27, 2015.
International Search Report and Written Opinion (ISA/US) for International Application No. PCT/US07/80013, dated Mar. 25, 2008.
International Search Report and Written Opinion (ISA/US) for International Application No. PCT/US08/76084, dated Feb. 19, 2009.
Bettinger, C.J. et al. (2009) "Engineering Substrate Micro- and Nanotopography to Control Cell Function," Angew Chem Int Ed Engl. 48(30):5406-5415.
Chen, A. et al. (2011) "Shrink-Film Configurable Multiscale Wrinkles for Functional Alignment of Human Embyronic Stem Cells and Their Cardiac Derivatives," Advanced Materials, 23:5785-5791.
Karakikes, I. et al. (2014) "Small Molecule-Mediated Directed Differentiation of Human Embryonic Stem Cells Toward Ventricular Cardiomyocytes," Stem Cells Translational Medicine 3:18-31.
Lieu, D.K. et al. (2013) "Mechanism-Based Facilitated Maturation of Human Pluripotent Stem Cell-Derived Cardiomyocytes," Circ Arrhythm Electrophysiol. 6:191-201.
Luna, J.I. et al. (2011) "Multiscale Biomimetic Topography for the Alignment of Neonatal and Embryonic Stem Cell-Derived Heart Cells," Tissue Engineering: Part C, 17(5):579-588.
Poon, E. et al. (2011) "Human Pluripotent Stem Cell-Based Approaches for Myocardial Repair: From the Electrophysical Perspective," Mol Pharmacol. 8:1495-1504.
U.S. Office Action dated Feb. 14, 2018, from U.S. Appl. No. 14/762,777.
Wang, J. et al. (2013) "Effect of engineered anisotropy on the susceptibility of human pluripotent stem cell-derived ventricular cardiomyocytes to arrhythmias," Biomaterials 34(35):8878-8886.
Yang, et al. 'Engineering Adolescence Maturation of Human Pluripotent Stem Cell-Derived Cardiomyocytes', Circulation Research, Jan. 31, 2014, DOI: 10.1161/CIRCRESAHA.114.300558.
Itzhaki, et al. "Calcium Handling in Embryonic Stem Cell-Derived Cardiac Myocytes of Mice and Men," (Ann. New York Academy of Sciences; 1080: 207-215, 2006).
U.S. Office Action dated Nov. 21, 2016, from U.S. Appl. No. 14/726,874.
Kim, T., et al., "Substrate Rigidity Regulates Ca2 Oscillation Via RhoA Pathway in Stem Cells," Journal of Cellular Physiology, 218: 285-293, 2008.
Lytton, Jonathan, "Na+/Ca2+ exchangers: three mammalian gene families control Ca2+ transport," Biochem. J. (2007) 406, 365-382.
Satin, et al., "Calcium Handling in Human Embryonic Stem Cell-Derived Cardiomyocytes," Stem Cells 2008; 26: 1961-1972.
U.S. Office Action dated Aug. 1, 2017, from U.S. Appl. No. 14/726,874.

\* cited by examiner

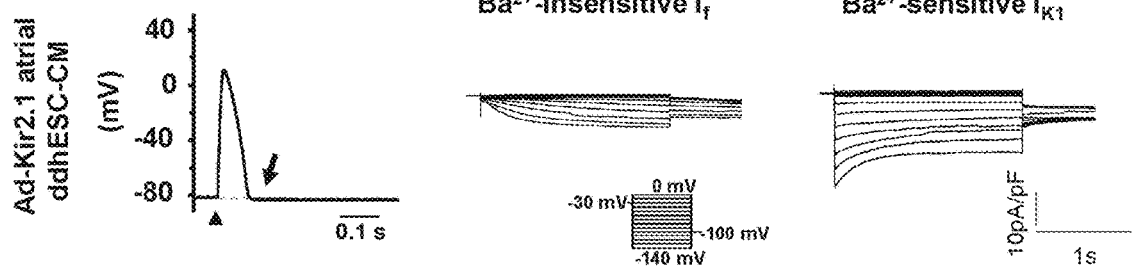
FIG. 5A
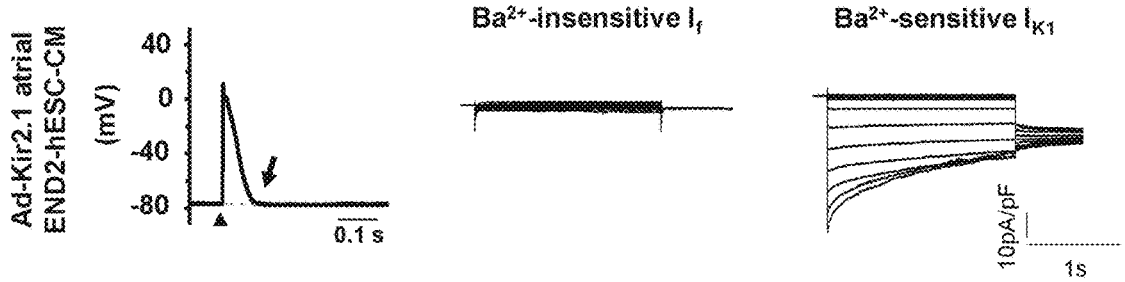
FIG. 5B
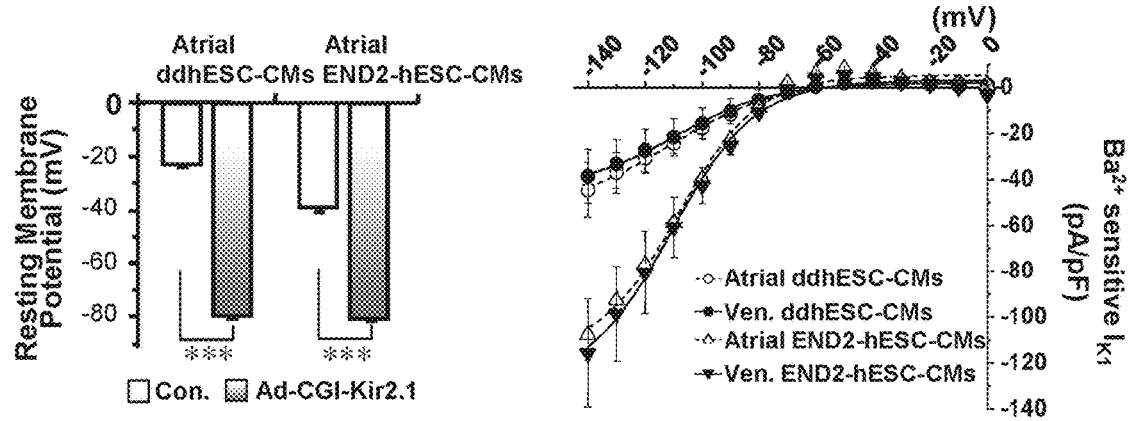
FIG. 5C
FIG. 5D

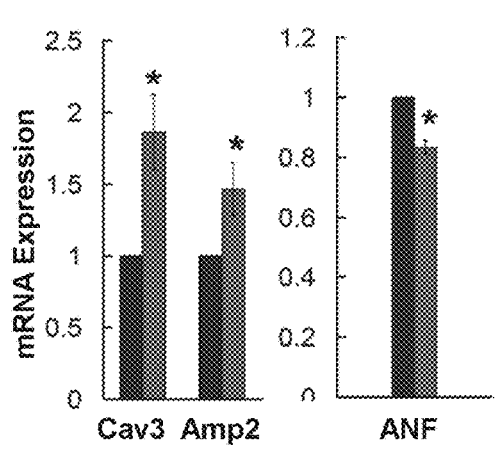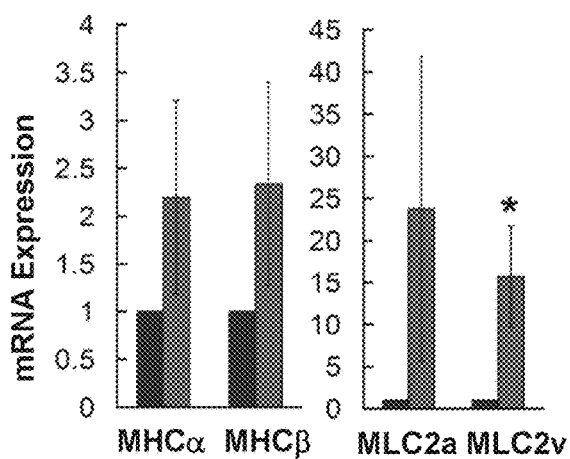
FIG. 6E
FIG. 6F
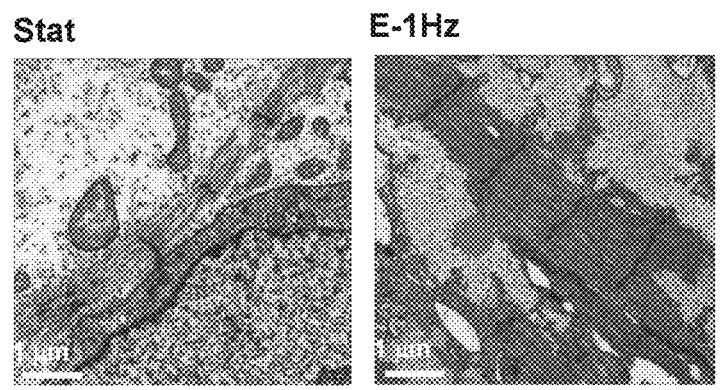
FIG. 6G

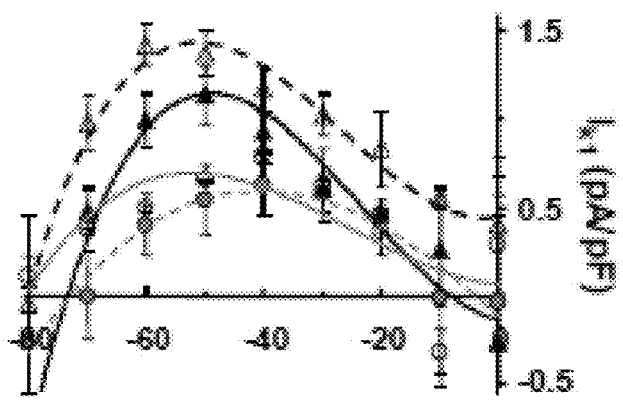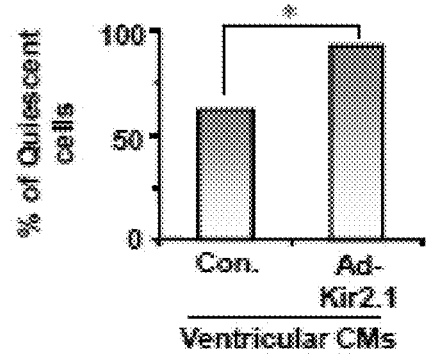
FIG. 9D　　　　　　　　　　　FIG. 9E
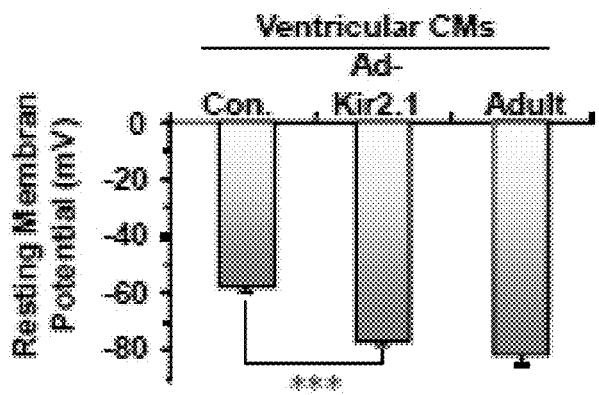
FIG. 9F
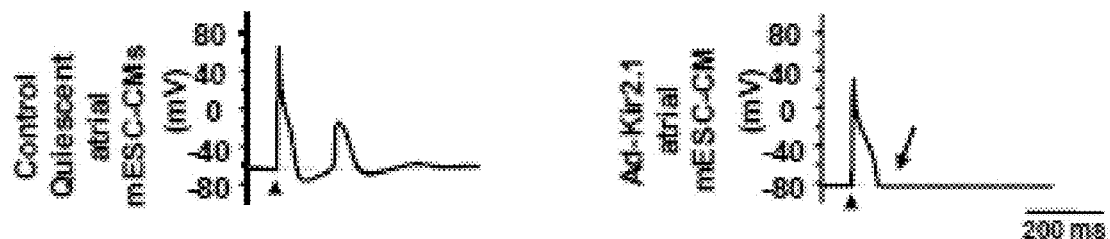
FIG. 10A

Static Control

E-1Hz

ELECTROPHYSIOLOGICALLY MATURE CARDIOMYOCYTES AND METHODS FOR MAKING SAME

CROSS-REFERENCE TO RELATED APPLICATIONS

This application claims the benefit under 35 U.S.C. § 119(e) of U.S. Provisional Application Ser. No. 61/936,807, filed Feb. 6, 2014, the content of which is incorporated by reference in its entirety into the present application.

STATEMENT OF GOVERNMENT SUPPORT

This invention was supported in whole or in part under Grant Number RO1 HL72857 awarded by National Institutes of Health (NIH). Accordingly, the U.S. government has rights to the inventions disclosed herein.

BACKGROUND

Throughout this disclosure, various publications, patents and published patent specifications are referenced by an identifying citation. Also within this disclosure are Arabic numerals referring to referenced citations, the full bibliographic details of which are provided immediately preceding the claims. The disclosures of these publications, patents and published patent specifications are hereby incorporated by reference into the present disclosure to more fully describe the state of the art to which this invention pertains.

Loss of non-regenerative, terminally differentiated cardiomyocytes (CMs) is irreversible; myocardial repair is further hampered by a severe shortage of donor cells and organs. CMs can be differentiated from human (h) embryonic stem cells (ESCs) that can propagate indefinitely in culture while maintaining their pluripotency (Kehat, I. et al. (2001) The Journal of Clinical Investigation 108:407-414; Mummery, C. et al. (2003) Circulation 107:2733-2740; Pera, M. F. et al. (2000) Journal of Cell Science 113(Pt 1):5-10; Thomson, J. A. et al. (1998) Curr. Top Dev. Biol. 38:133-165; Xue, T. et al. (2005) Circulation 111:11-20; Thomson, J. A. et al. (1998) Science 282:1145-1147; Reubinoff, B. E. et al. (2000) Nat. Biotechnol. 18:399-404; Xu, C. et al. (2002) Circ Res. 91:501-508; He, J. Q. et al. (2003) Circ. Res. 93:32-39). Therefore, hESCs can provide an unlimited ex vivo source of CMs for clinical application and drug testing. While existing efforts mostly focus on the derivation of heart cells from hESCs, it is imperative that these derived CMs are functionally mature in ways similar to their adult counterparts before the desired therapeutic outcome can be achieved. In fact, hESC-CMs exhibit embryonic- or fetal-like electrophysiological properties (Mummery, C. et al. (2003) Circulation 107:2733-2740; He, J. Q. et al. (2003) Circ. Res. 93:32-39; Satin, J. et al. (2004) J. Physiol. 559:479-496). For instance, hESC-derived ventricular CMs exhibit spontaneously firing action potentials (AP), in contrast to the normally quiescent-yet-excitable phenotype of adult. Indeed, it was previously demonstrated that transplantation of a node of electrically-active hESC-CMs, consisting of a mixture of ventricular, atrial and nodal cells, could collectively serve as a surrogate pacemaker in vitro and in vivo (Xue, T. et al. (2005) Circulation 111:11-20). Thus, immature hESC-CMs are potentially arrhythmogenic after transplantation. Moreover, there is a need to develop protocols for rescuing the immature phenotypes for their eventual clinical and other applications (e.g., cardiotoxicity screening and heart disease models that accurately reflects the adult heart). This disclosure satisfies this need and provides related advantages as well.

SUMMARY

In one aspect, this disclosure provides methods to mature the electrophysiological phenotype of a cell, a population of cells, and/or a tissue by contacting or applying to the cell or tissue an electrical current, i.e., electrical pacing. The phenotype of the cardiac muscle cell produced by the method comprises the five phases of a cardiac action potential; specifically, they are quiescent-yet-excitable, without Phase 4 depolarization or spontaneous firing, and maintain a relatively negative resting potential (at ~−80 mV)−.

The disclosure also provides methods for treating a patient in need thereof, wherein the patient is in need of one or more of promoting functional integration of these cells with the recipient heart after transplantation, thus providing therapeutic benefit such as to eliminate or reduce the arrhythmogenicity of immature cells and/or cardiomyocytes due to the immature electrophysiology of the cell or other resultant electrical disturbances. This disclosure also provides in vitro compositions and methods for drug discovery, cardiotoxicity screening and disease modeling, as the matured cells or their engineered tissues can more accurately reflect the properties of the native adult heart.

In one aspect, the disclosure provides a method for inducing expression of the Kir2.1 gene in a cell lacking functional Kir2.1 gene expression, with the proviso that the method excludes genetic manipulation of the cell, comprising, or alternatively consisting essentially of, or yet further consisting of, administering to the cell an effective amount of electrical pacing, thereby inducing expression of Kir2.1 gene expression in the cell.

In another aspect, a method is provided for inducing an electrophysiologically mature phenotype in a cell that is not terminally differentiated and/or electrophysiologically mature, comprising, or alternatively consisting essentially of, or yet further consisting of, administering to the cell that is not terminally differentiated and/or electrophysiologically mature an effective amount of electrical pacing, thereby inducing an electrophysiologically mature phenotype in the cell. As used herein, the term electrophysiologically immature phenotype intends a cell that displays one or more of a degree of automaticity (i.e., repetitive or spontaneous firing of AP at least 0.5 1, 2, 3 Hz or higher, Phase 4 depolarization, a relatively positive resting membrane potential or MDP of more positive than −80 mV, and delayed after-depolarization). In one aspect, the method excludes genetic manipulation of the cell to enhance or increase Kir2.1 expression.

In another aspect, a method is provided for preparing an electrophysiologically mature cardiomyocyte from a cell that is not terminally differentiated, comprising, or alternatively consisting essentially of, or yet further consisting of, administering to the cell that is not terminally differentiated, an effective amount of electrical pacing, thereby preparing an electrophysiologically mature cardiomyocyte. In one aspect, the method excludes genetic manipulation of the cell to enhance or increase Kir2.1 expression.

Cells that can be used in the method include cells that are not terminally differentiated, e.g., an embryonic stem cell, a pluriopotent stem cell, an embryoid body, a mesodermal cardiosphere or an induced pluripotent stem cell, or their cardiac derivatives.

In one aspect, the electrophysiologically mature cardiomyocyte exhibits one or more of a decrease of the atrial natriuretic factor (ANF) and/or an increase in one or more of the contractile proteins MHCα, MHCβ, MLC2a and MLC2v as well as cardiac calcium ion channel proteins. Methods to detect and monitor expression of these markers are described herein, or are known in the art and described in U.S. Patent Application Publication Nos. 2008/0089874 and 2012/0014924, each incorporated by reference herein.

In another aspect, the electrophysiologically mature cardiomyocyte comprises a cardiac cell of the group of a ventricular cell or an atrial cell. The cell is a mammalian cell, e.g., a murine cell, a bovine cell, a canine cell, a feline cell, an equine cell or a human cell.

In any of the above methods, the electrical pacing comprises applying or administering a pulsed electrical current of about 2.0 v/cm to about 3.0 v/cm, or alternatively about 2.5 v/cm, for about 2 msecs to about 8 msecs, or alternatively about 5 msec at a width of about 0.5 HZ to about 1.5 HZ, or alternatively about 1 HZ. In any of the above methods, the electrical pacing comprises a pulsed electrical current of about 1, 2.5, 10, etc. v/cm, for about 2, 5, 10 msec, etc. at a frequency of 1, 2, 3, 10 HZ etc. for various durations (1, 3, 5, 7 days, 2, 3, 4 weeks, etc.).

Further provided is an isolated cell prepared by the method as described above herein. In one aspect, the cell can be expanded or cultured to produce a population of cells that in one aspect, are substantially homogenous. In a further aspect, the substantially homogenous population is a clonal population. After the cell has been modified by a method as disclosed herein, it may be expanded to a substantially homogenous population (e.g., a clonal population) of these cells or alternatively, differentiated to a more mature cell type. Compositions containing these cells and populations of cells are also provided by this disclosure.

Thus, in one aspect, this disclosure provides an isolated electrophysiologically immature cell, such as an embryonic stem cell, pluripotent stem cell or a iPSC, or their derivatives, that has been modified to provide a mature electrophysiological phenotype. The disclosure also provides for a clonal population or a population of cells differentiated from electrophysiologically immature cells to provide a mature electrophysiological phenotype. In one aspect, the cells or tissues are further characterized by not being modified in one or more of the following manners: by transduction of a polynucleotide that promotes or inhibits $I_{K1}$ activity of the cells; by transduction of a polynucleotide that modulates Kir2 and HCN protein expression; by transduction of a polynucleotide that encodes a Connexin protein or enhances the expression of a Connexin protein; by transduction of a polynucleotide that modifies the calcium handling properties such as calsequestrin (CSQ); and by transduction of a polynucleotide that modifies other critical electrophysiological activties of the cells such as $I_{Kr}$, $I_{Ks}$, $I_{Na}$, $I_{Ca}$, $I_{to1}$, $I_{NaCa}$, $I_{NaK}$ and $I_{pCa}$. Methods to detect and monitor expression of these markers are known in the art and described in U.S. Patent Application Publication Nos. 2008/0089874 and 2012/0014924, each incorporated by reference herein.

These cells, populations and compositions have therapeutic and diagnostic uses. Non-limiting therapeutic uses include regenerating cardiac tissue, improving cardiac function, restoring action potential of cardiac tissue; and treating or preventing cardiac malfunction. These methods can be achieved by administering an effective amount of a cell or population of cells or tissue to a host in need thereof, e.g., a mammal such as a murine, a bovine, an equine, a canine, a feline, or a human patient. The cells and population of cells can be used diagnostically to screen drug or other therapeutic candidates.

The cells and compositions of the present invention can be used in the manufacture of medicaments and for the treatment of humans and other animals.

BRIEF DESCRIPTION OF THE FIGURES

FIG. 1A shows representative tracings of spontaneously firing (left) and quiescent (right) ventricular (top), atrial (middle) and pacemaker (bottom) action potentials (APs) recorded from ddhESC-CMs. The arrows denote a phase 4-like depolarization, which can be a proarrhythmic substrate of automaticity. FIG. 1B shows the percentage distribution of ventricular, atrial and pacemaker phenotypes, and FIG. 1C shows the percentage distribution of spontaneously-firing and quiescent ddhESC-CMs (n=70). FIG. 1D shows occurrence of DAD in ddhESC-CMs. FIG. 1E shows representative current tracings of $I_{CaL}$, $I_{Na}$, $I_{K1}$ and $I_f$, $I_{Kr}$ and $I_{Ks}$ in ventricular ddhESC-CMs. FIG. 1F shows representative tracings of spontaneously firing (left) and quiescent (right) ventricular and atrial human iPSC-CMs.

FIG. 2A shows current-voltage (I-V) relationships of $I_f$ in ventricular (n=6) and atrial (n=6) ddhESC-CMs. FIG. 2B shows steady-state activation curves of $I_f$ in ventricular (n=6) and atrial (n=6) ddhESC-CMs. FIG. 2C shows I-V relationships of $I_{CaL}$ in ventricular (n=17) and atrial (n=7) ddhESC-CMs. FIG. 2D shows steady-state inactivation curves of $I_{CaL}$ in ventricular (n=17) and atrial (n=7) ddhESC-CMs. FIG. 2E shows I-V relationship of $I_{Na}$ in ventricular ddhESC-CMs (n=4). FIG. 2F shows I-V relationships of $I_{Kr}$ in ventricular (n=6) and atrial (n=3) ddhESCCMs.

FIG. 3A shows representative action potential (AP) waveforms of spontaneous and quiescent ventricular, atrial and pacemaker END2-hESC-CMs as indicated (left), showing percentage distribution of ventricular, atrial and pacemaker phenotypes (top left), and the percentage distribution of spontaneously firing vs. quiescent END2-hESC-CMs (bottom left; n=33). The arrows indicate a phase 4-like depolarization, which can be a pro-arrhythmic substrate for automaticity. FIG. 3B shows representative current (I-V) tracings of $I_f$ and $I_{K1}$ in ventricular END2-hESC-CMs. FIG. 3C shows I-V curves of $I_f$ in ventricular (n=4) and atrial (n=4) END2-hESC-CMs. FIG. 3D shows representative AP waveforms of ventricular, atrial and pacemaker EB-hESC-CMs (top), current tracings of $I_f$ and $I_{K1}$ in ventricular EB-hESC-CMs (bottom left) and the percentage distributions of ventricular, atrial and pacemaker phenotypes, and spontaneously firing vs. quiescent EB-hESC-CMs (bottom right; n=18).

FIG. 4A shows in silico analysis of $I_{K1}$ effects on the maturation of ventricular embryonic electrophysiological phenotypes. FIG. 4B shows action potentials (APs), $I_f$ and $I_{K1}$ of Ad-Kir2.1-transduced ventricular ddhESC-CMs. FIG. 4C shows APs, $I_f$ and $I_{K1}$ of Ad-Kir2.1-transduced ventricular END2-hESC-CMs. Ad-Kir2.1 transduction eliminated the presence of phase 4-depolarization in both cell types (arrows). DAD was also never observed in Ad-Kir2.1-transduced cells. FIG. 4D shows the percentage of quiescent ventricular ddhESC-(n=45) and END2-hESC-CMs (n=20) increased significantly to 100% after Ad-CGI-Kir2.1 transduction (n=7 and n=13). FIG. 4E shows resting membrane potentials (RMPs) of Ad-Kir2.1-transduced CMs became significantly hyperpolarized relative to control and comparable to healthy adult CMs. FIG. 4F shows Ad-Kir2.1-silenced ventricular hESC-CMs spontaneously fired APs upon the addition of 200 µM $Ba^{2+}$, a potent $I_{K1}$ blocker, indicating $I_{K1}$ is a dominant regulator in controlling the automaticity of hESC-CMs. FIG. 4G shows the mRNA expression of contractile elements is significantly reduced after Ad-Kir2.1 transduction relative to control hESC-CMs (n=3).

FIGS. 5A-5D show Kir2.1 overexpression confers upon atrial ddhESC- and END2-hESC-CMs the electrophysiological properties of mature CMs. Representative APs, $I_f$ and $I_{K1}$ of Ad-Kir2.1-transduced atrial ddhESC-CMs (FIG. 5A) and atrial END2-hESC-CMs (FIG. 5B). In both cell types, Ad-Kir2.1 transduction eliminated the appearance of phase 4-depolarization (arrows). FIG. 5C shows resting membrane potentials (RMPs) of Ad-Kir2.1-transduced atrial ddhESC-(n=4) and END2-hESC-CMs (n=9) were significantly hyperpolarized compared to untransduced controls (n=42 and n=11). FIG. 5D shows current-voltage (I-V) curve of $I_{K1}$ in Ad-Kir2.1-transduced atrial and ventricular ddhESC-(n=4 and n=4) and END2-hESC-CMs (n=5 and n=4). I-V relationships of the transgenic Kir2.1 are similar between the atrial and ventricular CMs of each differentiation method.

FIGS. 6A-6G show effects of electrical conditioning on ddhESC-CMs. FIG. 6A shows electrophysiology of electrically conditioned ddhESC-CMs. Action potential (AP) profiles (left) of electrically conditioned atrial and ventricular ddhESC-CMs showed the absence of phase 4-deloparization (n=11). Both cell types also displayed more hyperpolarized resting membrane potential (RMP) (middle) that have resulted from an electrically induced increase in Kir2.1 expression (right). FIG. 6B shows electrically induced $Ca^{2+}$ transients and $Ca^{2+}$ wavefronts from unpaced control (top left; n=20) and electrically conditioned ddhESC-CMs (bottom left; n=34) and their average peak amplitude (right). FIG. 6C shows caffeine-induced $Ca^{2+}$ transients from unpaced control (top, black; n=23) and electrically conditioned ddhESC-CMs (bottom, gray; n=17) with their average peak amplitude (right; control, left bar, conditioned, right bar). FIG. 6D shows transcript analysis of $Ca^{2+}$-handling proteins (calsequestrin (CSQ), voltage-gated L-type $Ca^+$ channel or dihyropyridine receptor (DHPR), junctin (Junct), phospholamban (Phlmb), ryanodine receptor (RyR), sarco/endoplasmic reticulum $Ca^{2+}$ ATPase (SERCA), and triadin (Trdn)) showed significant increase for CSQ, Junct and Trdn (n=5). FIG. 6E shows mRNA expression of the t-tubule biogenesis proteins caveolin-3 (Cav3) and amphiphysin-2 (Amp2)) and adult atrial-specific marker (atrial natriuretic factor (ANF)) (n=5). FIG. 6F shows mRNA expression of contractile elements (myosin heavy chain (MHC)α, MHCβ, myosin light chain (MLC)2a, and MLC2v) (n=5). All bar graphs shown as mean±SEM with * denoting statistical significance (p<0.05). FIG. 6G shows typical TEM images of myofilaments in unpaced (n=15) and electrically conditioned (n=13) ddhESC-CMs showing distinct z-lines (arrows).

FIG. 8A shows representative tracings of spontaneously firing (left) and quiescent (right) ventricular (top), atrial (middle) and pacemaker (bottom) APs of mESC-CMs. The arrows indicate a phase 4-like depolarization, a proarrhythmic substrate of automaticity. FIG. 8B shows the percentage distribution of ventricular, atrial and pacemaker phenotypes (left) and the percentage distribution of spontaneously firing vs. quiescent characteristics (right) of total of mESC-CMs (n=60).

FIGS. 9A-9F show Kir2.1 overexpression confers upon mouse (m)ESC-CMs the electrophysiological properties of mature CMs. FIG. 9A shows a representative tracing of control ventricular mESC-CMs with DAD (left) and after Ad-Kir2.1 transduction showing absence of a phase 4-depolarization (right, arrow). Arrow heads indicate time of electrical stimulation. FIG. 9B shows total, $Ba^{2+}$-insensitive $I_f$ and $Ba^{2+}$-sensitive $I_{K1}$ currents recorded from the same cells in FIG. 9A. FIG. 9C shows current-voltage (I-V) relationships of $I_{K1}$ recorded from control spontaneously firing (open circles; n=3), control quiescent (solid circles; n=5), Ad-Kir2.1-transduced ventricular mESC-CMs (solid triangles; n=4) and adult mouse ventricular CMs (open triangles; n=5). FIG. 9D shows the zoomed-in outward components of $I_{K1}$ from FIG. 9C. FIG. 9E shows Kir2.1-overexpression (n=15) rendered nearly all ventricular mESC-CMs quiescent compared to control (n=24). FIG. 9F shows Ad-Kir2.1-transduced ventricular mESC-CMs (n=15) displayed a hyperpolarized resting membrane potential relative to the control mESC-CMs (n=24) and comparable to the adult counterparts (n=15). * denotes p<0.05.

FIGS. 10A-10E show overexpression of Kir2.1 similarly matures the electrophysiological phenotypes of atrial mouse (m)ESC-derived CMs. FIG. 10A shows a representative tracing of APs of a control atrial mESC-CMs with DAD (left) and after Ad-Kir2.1 transduction (right). Phase 4-depolarization is absent in Ad-Kir2.1-transduce atrial mESC-CMs (arrow). FIG. 10B shows $Ba^{2+}$-insensitive $I_f$ and $Ba^{2+}$-sensitive $I_{K1}$ currents recorded from the same cells from FIG. 10A. FIG. 10C shows current-voltage (I-V) relationships of $I_{K1}$ recorded from control spontaneously firing (open circles; n=3), control quiescent (solid circles; n=4) and Ad-Kir2.1-transduced atrial mESC-CMs (solid triangles; n=6). FIG. 10D shows Kir2.1 overexpression (n=22) rendered nearly all atrial mESC-CMs quiescent compared to control (n=29). FIG. 10E shows Ad-Kir2.1-transduced atrial mESC-CMs (n=22) displayed hyperpolarized resting membrane potential relative to control mESC-CMs (n=29), similar to their adult counterparts (n=8). * denotes p<0.05.

FIG. 13A shows a representative flow cytometric dot plot of unpaced control and electrically conditioned CMs derived from Lv-EF1α-GFP-MLC2v-DsRed reporter mESC line showing increased population of MLC2v positive cells in the polygonal gate. FIG. 13B shows average percentage of MLC2v-positive and median of unpaced control and electrically conditioned mESC-CMs (n=5). * indicates p<0.05.

DETAILED DESCRIPTION

Definitions

Figure 1A:
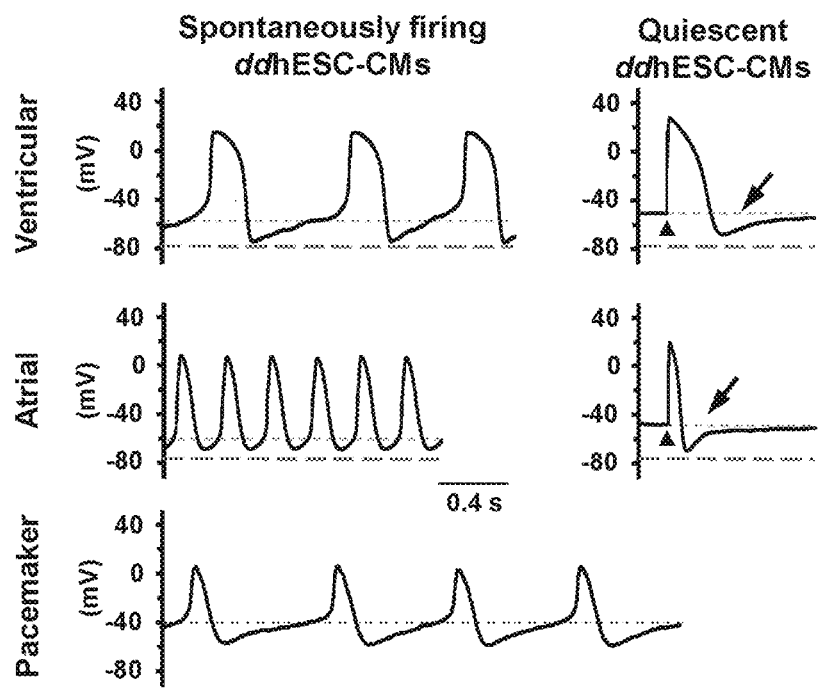
FIGS. 1A-1F show electrophysiology of pluripotent stem cell derived CMs.

The practice of the present invention will employ, unless otherwise indicated, conventional techniques of tissue culture, immunology, molecular biology, microbiology, cell biology and recombinant DNA, which are within the skill of the art. See, e.g., Sambrook, Fritsch and Maniatis, Molecular Cloning: A Laboratory Manual, $2^{nd}$ edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)); Harlow and Lane, eds. (1988) Antibodies, A Laboratory Manual; Harlow and Lane, eds. (1999) Using Antibodies, a Laboratory Manual; and Animal Cell Culture (R. I. Freshney, ed. (1987)).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a cell" includes a plurality of cells, including mixtures thereof.

"WT" is an abbreviation for "wild type." Wild type defines the cell, composition, tissue or other biological material as its exists in nature.

The "electrophysiology" of a cell or tissue is the electrical properties of said cell or tissue. These electrical properties are measurements of voltage change or electrical current flow at variety scales including, but are not limited to, single ion channel proteins, single cells, small populations of cells, tissues comprised of various cell populations, and whole organs (e.g. the heart). Several cell types and the tissues they comprise have electrical properties including, but not limited to, muscle cells, liver cells, pancreatic cells, ocular cells and neuronal cells. The electrical properties of a cell or tissue can be measured by the use of electrodes (examples include, but are not limited to, simple solid conductors including discs and needles, tracings on printed circuit boards, and hollow tubes, such as glass pipettes, filled an electrolyte). Intracellular recordings can be made by using techniques such as the voltage clamp, current clamp, patch-clamp, or sharp electrode. Extracellular recordings can be made by using techniques such as single unit recording, field potentials, and amperometry. A technique for high throughput analysis can also be used, such as the planar patch clamp. In another aspect, the Bioelectric Recognition Assay (BERA) can be used to measure changes in the membrane potential of cells. The above techniques are described in the following U.S. Pat. Nos. 7,270,730; 5,993,778; 6,461,860 and described in the following literature Hamill et al. (1981) Pflugers Arch. 391(2):85-100; Alvarez et al. (2002) Adv. Physiol. Educ. 26(1-4):327-341; Kornreich (2007) J. Vet. Cardiol. 9(1):25-37; Perkins (2006) J. Neurosci. Methods. 154(1-2):1-18; Gurney (2000) J. Pharmacol. Toxicol. Methods. 44(22):409-420; Baker et al. (1999) J. Neurosci. Methods 94(1):5-17; McNames and Pearson (2006) Conf. Proc. IEEE Eng. Med. Biol. Soc. 1(1):1185-1188; Porterfield (2007) Biosens. Bioelectron. 22(7):1186-1196; Wang and Li (2003) Assay Drug Dev. Technol. 1(5):695-708; and Kintzios et al. (2001) Biosens. Bioelectron. 16(4-5):325-336.

In addition to the electrophysiology of a cell or tissue being measured by the techniques described above, the electrophysiology of larger organs which are comprised of this cell or tissue can be measured by additional techniques, examples of which include, but are not limited to electrocardiograms (ECG or EKG). An ECG records the electrical activity of the heart over time. Analysis of the depolarization and repolarization waves results a description of the electrophysiology of the total heart muscle. In one embodiment, an ECG can be used to measure the cardiac function in a patient prior to and following administration of the cells or population of cells described herein.

The term "phenotype" refers to a description of an individual's trait or characteristic that is measurable and that is expressed only in a subset of individuals within a population. In one aspect of the invention, an individual's phenotype includes the phenotype of a single cell, a substantially homogeneous population of cells, a population of differentiated cells, or a tissue comprised of a population of cells.

In one aspect, an "electrophysiological phenotype" of a cell or tissue is the measurement of a cell or tissue's action potential. An action potential is a spike of electrical discharge that travels along the membrane of a cell. The properties of action potentials differ depending on the cell type or tissue. For example, cardiac action potentials are significantly different from the action potentials of most neuronal cells. In one embodiment, the action potential is a cardiac action potential. The "cardiac action potential" is a specialized action potential in the heart, with unique properties necessary for function of the electrical conduction system of the heart. The cardiac action potential has 5 phases; phase 4 (resting membrane potential), phase 0 (rapid depolarization), phase 1 (inactivation of the fast $Na^+$ channels causing a small downward deflection of the action potential), phase 2 (a.k.a. the plateau phase, is the sustained balance between inward movement of $Ca^{2+}$ and outward movement of $K^+$), phase 3 (cell repolarization), and back to phase 4. The cardiac action potentials of cells comprising the different portions of the heart have unique features and patterns specific to those cells including, atrial, ventricular, and pacemaker action potentials. One embodiment of the invention is the electrophysiological phenotype of an adult cardiac ventricular or atrial muscle cell that have normally electrically silent-yet-excitable properties.

"$I_{K1}$ activity" is the activity of a cell which results in the inward rectifier current of the cell. It is contemplated that the $I_{K1}$ activity is a stabilizer of a cell's resting membrane potential. This activity is controlled by a family of proteins termed the inward-rectifier potassium ion channels (Kir channels). There are seven subfamilies of Kir channels (Kir1, Kir2, Kir3, Kir4, Kir5, Kir6, and Kir7). Each subfamily has multiple members (e.g., Kir2.1, Kir2.2, Kir2.3, etc). The Kir2 subclass has four members, Kir2.1, Kir2.2, Kir2.3, and Kir2.4. The active Kir channels are formed from homotetrameric membrane proteins. Additionally, heterotetramers can form between members of the same subfamily (e.g., Kir2.1 and Kir2.3) when the channels are overexpressed. The proteins Kir2.1, Kir2.2, Kir2.3, and Kir2.4 are also known as IRK1, IRK2, IRK3, and IRK4, respectively.

These proteins have been sequenced and characterized, see for example GenBank Accession Nos. AAF73241, AAF73242, BAC02718, NP_000882, BAD23901, NP_066292, AAL89708, P63252, P52185, P52190, O19182, O18839, Q64273, P49656, P35561, CAA56622, AAY53910, Q14500, P52188, P52187, NP_001019861, NP_690607, NP_609903, Q64198, P52189, NP_004972, AAF97619, NP_733838, Q8JZN3 and O70596. The genes for these proteins have been sequenced and characterized, see for example GenBank Accession Nos. AB074970, AF153819, NM 000891, AB182123, NM_021012, AF482710, X80417, DQ023214, NM_001024690, NM_152868, NM_004981, AF181988, and NM_170720.

"$I_f$ activity" is the activity of a cell which results in the "funny" or pacemaker current of the cell. It is contemplated that this current functionally modulates pacing of cells which compose the heart (specifically the cells which compose the SA node). The $I_f$ activity is a mixed $Na^+/K^+$ inward current activated by hyperpolarization and modulated by the autonomic nervous system. This activity is controlled by a family of proteins termed the hyperpolarization-activated cyclic-nucleotide-modulated channels (HCN channels). There are four members of the HCN family (e.g., HCN1, HCN2, HCN3, and HCN4). HCN isoforms have been shown to coassemble and form heteromultimers. An HCN channel is activated by membrane hyperpolarization and modulated by cAMP and cGMP. These proteins have been sequenced and characterized, see for example GenBank Accession Nos. AA049470, AA049469, NP_446136, Q9UL51, NP_001185, NP_005468, NP_065948, EDL89402, NP_445827, NP_001034410 and NP_066550. The genes for these proteins have been sequenced and characterized, see for example GenBank Accession Nos. AF488550, AF488549, NM_053684, NM_001194, NM_005477, NM_020897, CH474029 and NM_001039321.

Examples of electrophysiological activities include, but are not limited to, $I_K$, $I_{Ks}$, $I_{Na}$, $I_{Ca}$, $I_{to1}$, $I_{NaCa}$, $I_{NaK}$ and $I_{pCa}$. Examples of proteins that modulate these activities include Nav1.5, Cav1.2, Kv4.2, Kv4.3, Kv7.1, Kv11.1, $3Na^+$-$1Ca^{2+}$-exchanger (NCX1), $3Na^+$-$2K^+$-ATPase, and $Ca^{2+}$-transporting ATPase. These proteins have been sequenced and characterized, see for example GenBank Accession Nos. CAC84530, NP 000710, CAB56841, AAF01045, NP_000209, NP_598004, CAA73478, ABV24476 and NP_001001787. The genes for these proteins have been sequenced and characterized, see for example GenBank Accession Nos. AJ310887, NM_000719, AJ010969, AF187964, NM_000218, NM_133497, Y13033, EU107280, NM_001001787.

A "ryanodine receptor" or (RyR) is a receptor that mediates the release of calcium ($Ca^{2+}$) from the sarcoplasmic reticulum. In skeletal muscle, it is believed that activation occurs via a physical coupling to the L-type calcium channel, while in cardiac muscle, the primary mechanism is calcium-induced calcium release. There are multiple isoforms of ryanodine: RyR1 primarily expressed in skeletal muscle; RyR2 primarily expressed in the myocardium; RyR3 is more widely expressed, but is especially in the brain; and and a fourth form found only in fish. These proteins have been sequenced and characterized, see for example GenBank Accession Nos. CAA01501, AAP29981, NP_001001534, NP_001095188, NP_001076231, BAA08309, AAB29457, Q92736, AAH59061, P30957, Q15413, AAI16743, NP_996757, CAA69029, and AAB58117. The gene for this protein has also been sequenced and characterized, see for example GenBank Accession Nos. NM_000540, NM_001035, NM_023868, NM_001001534, NM_177652. The above GenBank Accession Nos. were last accessed on Sep. 12, 2007.

A "Sarco/Endoplasmid Reticulum $Ca^{2+}$-ATPase" or (SERCA) is a 110-kDA transmembrane calcium pump which transfers $Ca^{2+}$ from the cytosol of the cell to the lumen of the sarcoplasmic reticulum at the expense of ATP hydrolysis during muscle relaxation. There are five isoforms of SERCA genes and the cardiac/slow skeletal muscle type splicing variant of the SERCA2a gene is the predominant SERCA isotype expressed in both normal and failing hearts. These proteins have been sequenced and characterized, see for example GenBank Accession Nos. NP_777617, NP_777615, NP_777614, NP_004311, NP_777618, NP_777613, NP_775293, CAB38029, CAA76764, BAD73969, BAD73967, AAB82290, NP_031530, NP_058025, NP_478120, AAB08097, NP_990850, NP_001672, NP_733765, and NP_001003214. The gene for this protein has also been sequenced and characterized, see for example GenBank Accession Nos. NM_001001396, NM_001684, NM_004320, and NM_174955. The above GenBank Accession Nos. were last accessed on Sep. 12, 2007.

A "$Na^+/Ca^{2+}$ exchanger" or (NCX) is a transmembrane protein and member of the cation/$Ca^{2+}$ antiporter family which plays a key role in maintaining cellular $Ca^{2+}$ homeostasis in a variety of cell types. These proteins have been sequenced and characterized, see for example GenBank Accession Nos. BAA83463, AAB50166, P70414, NP_524423, NP_732576, NP_732577, AAP37041, AAF06363, AAB46708, and NP_573484. The gene for this protein has also been sequenced and characterized, see for example GenBank Accession Nos. NM_170665, NM_001681, NM_001037102, NM_011406, NM_080440, NM_176632, and NM_012652. The above GenBank Accession Nos. were last accessed on Sep. 12, 2007.

A "cardiomyocyte or cardiac myocyte" is a specialized muscle cell which primarily forms the myocardium of the heart. Cardiamyocytes have five major components: 1. cell membrane (sarcolemma) and T-tubules, for impulse conduction, 2. sarcoplasmic reticulum, a calcium reservoir needed for contraction, 3. contractile elements, 4. mitochondria, and 5. a nucleus. Stem cells can be propagated to mimic the physiological functions of cardiomyocytes or alternatively, differentiate into cardiomyocytes. This differentiation can be detected by the use markers selected from, but not limited to, myosin heavy chain, myosin light chain, actinin, troponin, and tropomyosin.

The regulatory protein "Junctin" is a 26-kDa integral membrane protein, which forms a quaternary protein complex with the ryanodine receptor, calsequestrin and triadin at the junctional sarcoplasmic reticulum membrane in cardiac and skeletal muscles. Junctin is believed to work in conjunction with triadin as calsequestrin-anchoring proteins that couple calsequestrin to RyR and facilitate $Ca^{2+}$ release. These proteins have been sequenced and characterized, see for example GenBank Accession Nos. AAF82246, AAG16983, AAF82247, 2206415A, AAF37204, AAK00614, AAN87550, AAN87549, AAL09319, AAL09320, and AAL09321. The above GenBank Accession Nos. were last accessed on Sep. 12, 2007. The gene for this protein has also been sequenced and characterized, see for example Wetzel et al. (2000) Mol Genet. Metab. 69(3):252-258.

The regulatory protein "Triadin" is a 95 kDa integral membrane protein, which forms a quaternary protein complex with the ryanodine receptor (RyR), calsequestrin and junctin as described above. Triadin has also been shown to interact with dihydropyridine receptors (DHPR's). Triadin has been shown to co-localize with both DHPR and RyR at the junctional face of the terminal cisternae. These proteins have been sequenced and characterized, see for example GenBank Accession Nos. NP_006064, CAC44894, Q28820, NP_001076212, NP_001003154, CAD33526, AAA75315, CAI41045, CAI19636, AAC48496, AAC48497, AAC48498, AAL33878, AAL33877, and AAL33876. The gene for this protein has also been sequenced and characterized, see for example GenBank Accession Nos. NM_006073, NM_001003154, and BC139910. The above GenBank Accession Nos. were last accessed on Sep. 12, 2007.

The protein "Calsequestrin" ("CSQ") is the major calcium storage protein of the SR. Intraluminar $Ca^{2+}$ binds to calsequestrin during diastole to prevent $Ca^{2+}$ precipitation and to lower its free ionic concentration to facilitate efficient storage. Calsequestrin forms part of a large quaternary complex with the ryanodine receptor, triadin, and junctin as described above. These proteins have been sequenced and characterized, see for example GenBank Accession Nos. NP_001222, NP_001223, BAA23494, CAI23373, CAI14532, CAI15276, EAW52736, AAH22289, AAA48674, CAA45609, NP_001095161, AAB87570, AAC69472, AAI05186, BAF34916, and AAI33410. The gene for this protein has also been sequenced and characterized, see for example GenBank Accession Nos. NM_001232 and NM_001231. The above GenBank Accession Nos. were last accessed on Sep. 12, 2007.

The protein "Phospholamban" is a 52 amino acid integral membrane protein that regulates the $Ca^{2+}$ pump in cardiac muscle cells. Dephosphorylated phospholamban interacts with the $Ca^{2+}$ ATPase pump SERCA to lower its activity and sensitivity to $Ca^{+2}$, thus decreasing $Ca^{2+}$ uptake into the sarcoplasmic reticulum. Thus, when phospholamban is phosphorylated, its interact with SERCA is reduced, resulting in an increase in $Ca^{2+}$ transport into the sarcoplasmic reticulum. This protein has been sequenced and characterized, see for example GenBank Accession Nos. NP_002658, NP_073198, NP_075618, NP_001003332, NP_999378, NP_001076090, NP_990741, and P61012. The gene for this protein has also been sequenced and characterized, see for example GenBank Accession Nos. NM_214213, NM_002667, NM_023129 and NM_001003332. The above GenBank Accession Nos. were last accessed on Sep. 12, 2007.

The cadiomyocyte marker "myosin heavy chain" and "myosin light chain" are part of a large family of motor proteins found in muscle cells responsible for producing contractile force. These proteins have been sequenced and characterized, see for example GenBank Accession Nos. AAD29948, CAC70714, CAC70712, CAA29119, P12883, NP_000248, P13533, CAA37068, ABR18779, AAA59895, AAA59891, AAA59855, AAB91993, AAH31006, NP_000423, and ABC84220. The genes for these proteins has also been sequenced and characterized, see for example GenBank Accession Nos. NM_002472 and NM_000432. The above GenBank Accession Nos. were last accessed on Sep. 12, 2007.

The cardiomyocyte marker "actinin" is a mircrofilament protein which are the thinnest filaments of the cytoskeleton found in the cytoplasm of all eukaryotic cells. Actin polymers also play a role in actomyosin-driven contractile processes and serve as platforms for myosin's ATP hydrolysis-dependent pulling action in muscle contraction. This protein has been sequenced and characterized, see for example GenBank Accession Nos. NP_001093, NP_001095, NP_001094, NP_004915, P35609, NP_598917, NP_112267, AAI07534, and NP_001029807. The gene for this protein has also been sequenced and characterized, see for example GenBank Accession Nos. NM_001102, NM_004924, and NM_001103. The above GenBank Accession Nos. were last accessed on Sep. 12, 2007.

The cardiomyocyte marker "troponin" is a complex of three proteins that is intergral to muscle contraction in skeletal and cardiac muscle. Troponin is attached to the protein "tropomyosin" and lies within the groove between actin filaments in muscle tissue. Tropomyosin can be used as a cardiomyocyte marker. These proteins have been sequenced and characterized, see for example GenBank Accession Nos. NP_000354, NP_003272, P19429, NP_001001430, AAB59509, AAA36771, and NP_001018007. The gene for this protein has also been sequenced and characterized, see for example GenBank Accession Nos. NM_000363, NM_152263, and NM_001018007. The above GenBank Accession Nos. were last accessed on Sep. 12, 2007.

The protein "caveolin 3" is a 151 amino acid (~20-kDA) protein shown to be associated with the caveolar plasma membranes and is a muscle specific form of the caveolin family. Caveolins in general are believed to act as scaffolding proteins within caveolar membranes. This protein has been sequenced and characterized, see for example GenBank Accession Nos. NP_203123, NP_001225, P56539, NP_062028, NP_031643, and Q2KI43. The gene for this protein has also been sequenced and characterized, see for example GenBank Accession Nos. NM_019155 and Z18951. The above GenBank Accession Nos. were last accessed on Sep. 12, 2007.

The protein "amphiphysin 2" (also known as Binl) have a putative role in membrane deformation at endocytic sites. An isoform of amphiphysin 2 concentrated at T-tubules induces tubular plasma membrane invaginations when expressed in nonmuscle cells. In developing myotubes, amphiphysin 2 and caveolin 3 segregate in tubular and vesicular portions of the T-tubules system, respectively. These proteins have been sequenced and characterized, see for example GenBank Accession Nos. NP_647477, CAA57197, P49418, NP_778172, and CAA73807. The gene for this protein has also been sequenced and characterized, see for example GenBank Accession Nos. NM_009668, NM_139343, NM_139344, NM_139346, NM_139347, NM_139349, NM_139345, NM_139348, NM_004305, NM_139350, and NM_139351. The above GenBank Accession Nos. were last accessed on Sep. 12, 2007.

In one aspect, an "electrophysiological phenotype" of a cell or tissue is the measurement of a cell or tissue's action potential. An action potential is a spike of electrical discharge that travels along the membrane of a cell. The properties of action potentials differ depending on the cell type or tissue. For example, cardiac action potentials are significantly different from the action potentials of most neuronal cells. In one embodiment, the action potential is a cardiac action potential. The "cardiac action potential" is a specialized action potential in the heart, with unique properties necessary for function of the electrical conduction system of the heart. The cardiac action potential has 5 phases; phase 4 (resting membrane potential), phase 0 (rapid depolarization), phase 1 (inactivation of the fast $Na^+$ channels causing a small downward deflection of the action potential), phase 2 (a.k.a. the plateau phase, is the sustained balance between inward movement of $Ca^{2+}$ and outward movement of $K^+$), phase 3 (cell repolarization), and back to phase 4. The cardiac action potentials of cells comprising the different portions of the heart have unique features and patterns specific to those cells including, atrial, ventricular, and pacemaker action potentials. This action potential is a unique property of SA nodal cells and most importantly the spontaneous depolarization (a.k.a. automaticity) necessary for SA node's pacemaker activity. The normal activity of SA nodal cells of the heart is to spontaneously depolarize at regular rhythm, thus generating a normal heart rate. Another embodiment of the invention is the electrophysiological phenotype of an adult cardiac ventricular or atrial muscle cell that have normally electrically silent-yet-excitable properties.

"$I_{K1}$ activity" is the activity of a cell which results in the inward rectifier current of the cell. It is contemplated that the $I_{K1}$ activity is a stabilizer of a cell's resting membrane potential. This activity is controlled by a family of proteins termed the inward-rectifier potassium ion channels (Kir channels). There are seven subfamilies of Kir channels (Kir1, Kir2, Kir3, Kir4, Kir5, Kir6, and Kir7). Each subfamily has multiple members (e.g. Kir2.1, Kir2.2, Kir2.3, etc). The Kir2 subclass has four members, Kir2.1, Kir2.2, Kir2.3, and Kir2.4. The active Kir channels are formed from homotetrameric membrane proteins. Additionally, heterotetramers can form between members of the same subfamily (e.g. Kir2.1 and Kir2.3) when the channels are overexpressed. The proteins Kir2.1, Kir2.2, Kir2.3, and Kir2.4 are also known as IRK1, IRK2, IRK3, and IRK4, respectively. These proteins have been sequenced and characterized, see for example GenBank Accession Nos. AAF73241, AAF73242, BACO2718, NP_000882, BAD23901, NP_066292, AAL89708, P63252, P52185, P52190, O19182, O18839, Q64273, P49656, P35561, CAA56622, AAY53910, Q14500, P52188, P52187, NP_001019861, NP_690607, NP_609903, Q64198, P52189, NP_004972, AAF97619, NP_733838, Q8JZN3 and O70596, last accessed on Sep. 28, 2007. The genes for these proteins have been sequenced and characterized, see for example GenBank Accession Nos. AB074970, AF153819, NM_000891, AB182123, NM_021012, AF482710, X80417, DQ023214, NM_001024690, NM_152868, NM_004981, AF181988, and NM_170720, last accessed on Sep. 28, 2007.

"$I_f$ activity" is the activity of a cell which results in the "funny" or pacemaker current of the cell. It is contemplated that this current functionally modulates pacing of cells which compose the heart (specifically the cells which compose the SA node). The $I_f$ activity is a mixed $Na^+/K^+$ inward current activated by hyperpolarization and modulated by the autonomic nervous system.

Atrial Natriuretic Factor (ANF) is a short (approximately 28 amino acids) peptide that is produced, stored and released by cardiac myocytes of the atria of the heart. It is released in response to atrial stretch and a variety of other signals. The amino acid and putative gene for an ANF precursor is known in the art, for example at GenBank Accession No. X01471, last accessed on Sep. 10, 2008. A synthetic gene and its translation product ANF is reported at GenBank Accession No. X08077, last accessed on Sep. 10, 2008.

The phrase "equivalent protein" refers to protein or polynucleotide which hybridizes to the exemplified polynucleotide under stringent conditions and which exhibit similar or enhanced biological activity in vivo, e.g., over 120%, or alternatively over 110%, or alternatively over 100%, or alternatively, over 90% or alternatively over 85% or alternatively over 80%, or alternatively over 70%, as compared to the standard or control biological activity. Additional embodiments within the scope of this invention are identified by having more than 80%, or alternatively, more than 85%, or alternatively, more than 90%, or alternatively, more than 95%, or alternatively more than 97%, or alternatively, more than 98 or 99% sequence identity. Percentage identity can be determined by sequence comparison programs such as BLAST run under appropriate conditions. In one aspect, the program is run under default parameters.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

A "gene" refers to a polynucleotide containing at least one open reading frame (ORF) that is capable of encoding a particular polypeptide or protein after being transcribed and translated. Any of the polynucleotide sequences described herein may be used to identify larger fragments or full-length coding sequences of the gene with which they are associated. Methods of isolating larger fragment sequences are known to those of skill in the art.

The term "express" refers to the production of a gene product.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell. "Differentially expressed" as applied to a gene, refers to the differential production of the mRNA transcribed from the gene or the protein product encoded by the gene. A differentially expressed gene may be overexpressed or underexpressed (a.k.a. inhibited) as compared to the expression level of a normal or control cell. In one aspect, it refers to overexpression that is 1.5 times, or alternatively, 2 times, or alternatively, at least 2.5 times, or alternatively, at least 3.0 times, or alternatively, at least 3.5 times, or alternatively, at least 4.0 times, or alternatively, at least 5 times, or alternatively 10 times higher (i.e., and therefore overexpressed) or lower than the expression level detected in a control sample. The term "differentially expressed" also refers to nucleotide sequences in a cell or tissue which are expressed where silent in a control cell or not expressed where expressed in a control cell.

A "gene product" or alternatively a "gene expression product" refers to the amino acid (e.g., peptide or polypeptide) generated when a gene is transcribed and translated.

"Connexin" or gap junction proteins, are a family of structurally related transmembrane proteins that assemble to form vertebrate gap junctions. Each gap junction comprises 2 hemichannels, or "connexons", which are themselves each constructed out of 6 connexin proteins. It is contemplated that these gap junctions are essential for proper coordinated depolarization of cardiomyocytes composing heart muscle. Connexins are most commonly named according to their molecular weights (e.g. Cx26 is the connexin protein of 26 kDa). However, these proteins are also known by a different nomenclature known as the Gja/Gjb system. A description of this system can be found at (http://www.gene.ucl.ac.uk/nomenclature/genefamily/gj.html). These proteins have been sequenced and characterized, see for example GenBank Accession Nos. NP_003995, Q6PEYO, NP_940970, NP_006774, NP_853516, NP_699199, NP_689343, NP_694944, O75712, NP_001005752, NP_005259, P08034, NP_000157, NP_065711, NP_000156, NP_005488, NP_068773, Q5T442, AAH89439, NP_005258, NP_110399 and EAW48537. The genes for these proteins have been sequenced and characterized, see for example GenBank Accession Nos. NM_004004, NM_198568, NM_006783, NM_181538, NM_153368, NM_152219, NM_153212, NM_005268, NM_000166, NM_020660, NM_000165, NM_005497, NM_021954, BC089439, NM_005267, NM_030772, and CH471051.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" intends the polynucleotides are arranged in a manner that allows them to function in a cell.

"Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors, e.g., viral vectors, are known to be capable of mediating transfer of genes to mammalian cells, as is known in the art and described herein.

A "probe" when used in the context of polynucleotide manipulation refers to an oligonucleotide that is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and proteins, including enzymes.

A "primer" is a short polynucleotide, generally with a free 3'-OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in "PCR: A Practical Approach" (M. MacPherson et al., IRL Press at Oxford University Press (1991)). All processes of producing replicate copies of a polynucleotide, such as PCR or gene cloning, are collectively referred to herein as "replication." A primer can also be used as a probe in hybridization reactions, such as Southern or Northern blot analyses. Sambrook et al., infra.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example those described in Current Protocols in Molecular Biology (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/cgi-bin/BLAST.

The term "polypeptide" is used interchangeably with the term "protein" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" refers to a juxtaposition wherein the elements are in an arrangement allowing them to function.

As used herein, the term "comprising" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "isolated" means separated from constituents, cellular and otherwise, in which the cell, tissue, polynucleotide, peptide, polypeptide, protein, antibody or fragment(s) thereof, which are normally associated in nature. For example, an isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart. An isolated cell is a cell that is separated form tissue or cells of dissimilar phenotype or genotype.

As used herein, "stem cell" defines a cell with the ability to divide for indefinite periods in culture and give rise to specialized cells. At this time and for convenience, stem cells are categorized as somatic (adult) or embryonic. A somatic stem cell is an undifferentiated cell found in a differentiated tissue that can renew itself (clonal) and (with certain limitations) differentiate to yield all the specialized cell types of the tissue from which it originated. An embryonic stem cell is a primitive (undifferentiated) cell from the embryo that has the potential to become a wide variety of specialized cell types. An embryonic stem cell is one that has been cultured under in vitro conditions that allow proliferation without differentiation for months to years. Pluripotent embryonic stem cells can be distinguished from other types of cells by the use of marker including, but not limited to, Oct-4, alkaline phosphatase, CD30, TDGF-1, GCTM-2, Genesis, Germ cell nuclear factor, SSEA1, SSEA3, and SSEA4. The term "stem cell" also includes "dedifferentiated" stem cells, an example of which is a somatic cell which is directly converted to a stem cell, i.e. reprogrammed. A clone is a line of cells that is genetically identical to the originating cell; in this case, a stem cell.

An "induced pluripotent cell" intends embryonic-like cells reprogrammed to the immature phenotype from adult cells. Various methods are known in the art, e.g., "A simple new way to induce pluripotency" Nature, 29 Jan. 2014 and available at sciencedaily com/releases/2014/01/140129184445, last accessed on Feb. 5, 2014 and U.S. Patent Application Publication No. 2010/0041054. Human iPSCs also express stem cell markers and are capable of generating cells characteristic of all three germ layers.

The term "propagate" means to grow or alter the phenotype of a cell or population of cells. The term "growing" or "expanding" refers to the proliferation of cells in the presence of supporting media, nutrients, growth factors, support cells, or any chemical or biological compound necessary for obtaining the desired number of cells or cell type. In one embodiment, the growing of cells results in the regeneration of tissue. In yet another embodiment, the tissue is comprised of cardiomyocytes.

The term "culturing" refers to the in vitro propagation of cells or organisms on or in media of various kinds. It is understood that the descendants of a cell grown in culture may not be completely identical (i.e., morphologically, genetically, or phenotypically) to the parent cell. By "expanded" is meant any proliferation or division of cells.

"Clonal proliferation" refers to the growth of a population of cells by the continuous division of single cells into two identical daughter cells and/or population of identical cells.

As used herein, the "lineage" of a cell defines the heredity of the cell, i.e., its predecessors and progeny. The lineage of a cell places the cell within a hereditary scheme of development and differentiation.

"Differentiation" describes the process whereby an unspecialized cell acquires the features of a specialized cell such as a heart, liver, or muscle cell. "Directed differentiation" refers to the manipulation of stem cell culture conditions to induce differentiation into a particular cell type or phenotype. "Dedifferentiated" defines a cell that reverts to a less committed position within the lineage of a cell. As used herein, the term "differentiates or differentiated" defines a cell that takes on a more committed ("differentiated") position within the lineage of a cell. As used herein, "a cell that differentiates into a mesodermal (or ectodermal or endodermal) lineage" defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, leiomyogenic, chondrogenic, cardiogenic, dermatogenic, hematopoetic, hemangiogenic, myogenic, nephrogenic, urogenitogenic, osteogenic, pericardiogenic, or stromal.

Examples of cells that differentiate into ectodermal lineage include, but are not limited to epidermal cells, neurogenic cells, and neurogliagenic cells.

Examples of cells that differentiate into endodermal lineage include, but are not limited to pleurogenic cells, and hepatogenic cells, cell that give rise to the lining of the intestine, and cells that give rise to pancreogenic and splanchogenic cells.

As used herein, a "pluripotent cell" defines a less differentiated cell that can give rise to at least two distinct (genotypically and/or phenotypically) further differentiated progeny cells.

A "multi-lineage stem cell" or "multipotent stem cell" refers to a stem cell that reproduces itself and at least two further differentiated progeny cells from distinct developmental lineages. The lineages can be from the same germ layer (i.e., mesoderm, ectoderm or endoderm), or from different germ layers. An example of two progeny cells with distinct developmental lineages from differentiation of a multilineage stem cell is a myogenic cell and an adipogenic cell (both are of mesodermal origin, yet give rise to different tissues). Another example is a neurogenic cell (of ectodermal origin) and adipogenic cell (of mesodermal origin).

As used herein, the term "electrical pacing" intends to apply a small electrical current(s) at particular frequencies and durations to artificially produce or mimic a cardiac contraction (e.g., a heartbeat).

"Substantially homogeneous" describes a population of cells in which more than about 50%, or alternatively more than about 60%, or alternatively more than 70%, or alternatively more than 75%, or alternatively more than 80%, or alternatively more than 85%, or alternatively more than 90%, or alternatively, more than 95%, of the cells are of the same or similar phenotype. Phenotype can be determined by a pre-selected cell surface marker or other marker, e.g., myosin or actin or the expression of a gene or protein, A "biocompatible scaffold" refers to a scaffold or matrix for tissue-engineering purposes with the ability to perform as a substrate that will support the appropriate cellular activity to generate the desired tissue, including the facilitation of molecular and mechanical signaling systems, without eliciting any undesirable effect in those cells or inducing any undesirable local or systemic responses in the eventual host. In other embodiments, a biocompatible scaffold is a precursor to an implantable device which has the ability to perform its intended function, with the desired degree of incorporation in the host, without eliciting an undesirable local or systemic effects in the host. Biocompatible scaffolds are described in U.S. Pat. No. 6,638,369.

A "composition" is intended to mean a combination of active agent, cell or population of cells and another compound or composition, inert (for example, a detectable agent or label) or active, such as a biocompatible scaffold.

A "pharmaceutical composition" is intended to include the combination of an active agent with a carrier, inert or active such as a biocompatible scaffold, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, Remington's Pharm. Sci., 15th Ed. (Mack Publ. Co., Easton (1975)).

An "effective amount" is an amount sufficient to effect beneficial or desired results. An effective amount can be administered in one or more administrations, applications or dosages.

A "subject," "individual" or "patient" is used interchangeably herein, and refers to a vertebrate, preferably a mammal, more preferably a human. Mammals include, but are not limited to, murines, rats, simians, bovines, canines, humans, farm animals, sport animals and pets.

Unmodified cells are sometimes referred to as "source cells" or "source stem cells". The cells may be prokaryotic or eukaryotic, and include but are not limited to bacterial cells, yeast cells, plant cells, insect cells, animal cells, and mammalian cells, e.g., murines, rats, simians, bovines, canines, porcines and humans.

In one embodiment, an "immature cell" refers to a cell which does not possess the desired (adult) phenotype or genotype. For example, in one embodiment, a mature cell is a cell that is being replaced. The immature cell can be subjected to techniques including physical, biological, or chemical processes which changes, initiates a change, or alters the phenotype or genotype of the cell into a "mature cell." A "mature cell" refers to a cell which possess the desired phenotype or genotype. In one embodiment, a mature cell has the phenotype or genotype of, but is not limited to, an adult cardiomyocyte, atrial cardiomyocyte, ventricular cardiomyocyte.

A "control" is an alternative subject or sample used in an experiment for comparison purpose. A control can be "positive" or "negative". For example, where the purpose of the experiment is to determine a correlation of an altered expression level of a gene with a particular phenotype, it is generally preferable to use a positive control (a sample from a subject, carrying such alteration and exhibiting the desired phenotype), and a negative control (a subject or a sample from a subject lacking the altered expression or phenotype).

As used herein, the terms "treating," "treatment" and the like are used herein to mean obtaining a desired pharmacologic and/or physiologic effect. The effect can be prophylactic in terms of completely or partially preventing a disorder or sign or symptom thereof, and/or can be therapeutic in terms of a partial or complete cure for a disorder and/or adverse effect attributable to the disorder. Examples of "treatment" include but are not limited to: preventing a disorder from occurring in a subject that may be predisposed to a disorder, but has not yet been diagnosed as having it; inhibiting a disorder, i.e., arresting its development; and/or relieving or ameliorating the symptoms of disorder, e.g., cardiac arrhythmia. As is understood by those skilled in the art, "treatment" can include systemic amelioration of the symptoms associated with the pathology and/or a delay in onset of symptoms such as chest pain. Clinical and sub-clinical evidence of "treatment" will vary with the pathology, the individual and the treatment.

The phrase "cardiac malfunction" refers to the heart, portions of the heart, or individual cells of the heart which do not have the proper electrophysiological phenotype to perform their necessary activity to maintain normal beating of the heart muscle. Cardiac malfunction can be caused by, but not limited to, diseases or disorders including sick sinus syndrome, congestive heart failure, isolated diastolic heart failure, bradyarrhythmia, atrial tachyarrhythmia, ventricular tachyarrhythmia, myocardial infarction, and cardiac arrhythmia. Cardiac arrhythmia includes, but is not limited to, bradycardia, tachycardia, abnormal sinus node function, or atrioventricular block.

Modified Cells and Populations of Cells

One embodiment of the invention is an isolated electrophysiologically immature cell that has been modified by electrical pacing to provide the phenotype of an electrophysiologically mature cell. Examples of cells that can be modified include, but are not limited to embryonic stem cells, iPSCs, progenitor cells and adult stem cells that possess the ability to further differentiate into cells of a desired lineage. The cells can be isolated from a host or can be obtained from an established cell culture. Methods to isolate and culture ESC are known in the art and described in Xue et al. (2005) Circulation 111:11-20, Thomson et al. (1998) Science 282:1145-1147, Moore et al. (2005) Reproductive Toxicology 20:377-391, and Wang et al. (2005) Stem Cells 23:1526-1534. Available sources of these cells include, for example, from the NIH Human Embryonic Stem Cell Registry.

The cells can be from any suitable source, e.g., an animal or vertebrate. Non-limiting examples include murine, rat, canine, simian, porcine and human.

The mature electrophysiology phenotype is obtained by modifying the phenotype of the source cell. In one aspect, the modification of the source cell or its derivative expressly excludes transducing the source cell with a polynucleotide that modulates $I_{K1}$ and $I_f$ activity of the cell. In another aspect, modification of the cell or its derivative expressly excludes modification by transducing the cell with a polynucleotide that promotes or inhibits the expression of a protein that modulates $I_{K1}$ activity. Examples of proteins that modulate $I_{K1}$ and CSQ activity of the cell include, but are not limited to, the Kir2 family of proteins and the HCN family of proteins. The Kir2 family includes the Kir2.1, Kir2.2, Kir2.3, Kir2.4 and a functionally equivalent protein thereof. In yet another aspect, the modification expressly excludes modification of the isolated electrophysiologically immature cell to comprise a polynucleotide that encodes a Connexin protein or a polypeptide that enhances the expression of a Connexin protein. Examples of Connexin proteins include, but are not limited to Cx23, Cx25, Cx26, Cx30.2, Cx30, Cx31.9, Cx30.3, Cx31, Cx31.1, Cx32, Cx36, Cx43, Cx45, Cx46, Cx47, Cx50, Cx59, and Cx62.

Another embodiment of the disclosure is an isolated electrophysiologically immature cell that has other modified electrophysiology activities including, but not limited to, $I_{K1}$, $I_{Ks}$, $I_{Na}$, $I_{Ca}$, $I_{to1}$, $I_{NaCa}$, $I_{NaK}$ and $I_{pCa}$ activity. Examples of proteins that modulate these activities include Nav1.5, Cav1.2, Kv4.2, Kv4.3, Kv7.1, Kv1.1.1, 3Na$^+$-1Ca$^{2+}$-exchanger, 3Na$^+$-2K$^+$-ATPase, and Ca$^{2+}$-transporting ATPase.

This invention also provides a cell that has been modified as described above, wherein the cell further expresses a cardiomyocyte marker selected from, but not limited to, myosin heavy chain, myosin light chain, actinin, troponin, tropomyosin and cardiac calcium handling proteins. Examples of calcium channel proteins include, but are not limited to ryanodine receptor (RyR), calsequestrin, junctin, triadin, phospholamban. In one aspect, the cell expresses on or more calcium pump proteins, sarco/endoplasmic reticulum CA$^{2+}$-ATPase (SERCA) protein, and/or reduced expression of the Na$^+$/Ca$^{2+}$ exchanger (NCX) protein.

The immature or source cell is modified to provide the desired electrophysiological phenotype by contacting the cell with an electrical current, e.g., by electrical pacing of the cells.

This invention also provides a substantially homogeneous population of electrophysiologically immature cells that have been modified as described above. One embodiment of the invention is a substantially homogeneous population of electrophysiological immature cells that are modified by electrical pacing.

Another embodiment of the invention is a substantially homogeneous population of electrophysiologically immature cells, in one aspect a clonal population, that have other modified electrophysiology activities including, but not limited to, $I_{Kr}$, $I_{Ks}$, $I_{Na}$, $I_{Ca}$, $I_{to1}$, $I_{NaCa}$, $I_{NaK}$ and $I_{pCa}$ activity. Examples of proteins that modulate these activities include Nav1.5, Cav1.2, Kv4.2, Kv4.3, Kv7.1, Kv11.1, 3Na$^+$-1Ca$^{2+}$-exchanger, 3Na$^+$-2K$^+$-ATPase, and Ca$^{2+}$-transporting ATPase. This invention also provides a substantially homogeneous population of electrophysiologically immature cells that has been modified as described above, wherein the cells further express a cardiomyocyte marker selected from, but not limited to, myosin heavy chain, myosin light chain, actinin, troponin and tropomyosin. Examples of proteins that modulate these activities include Nav1.5, Cav1.2, Kv4.2, Kv4.3, Kv7.1, Kv11.1, 3Na$^+$-1Ca$^{2+}$-exchanger, 3Na$^+$-2K$^+$-ATPase, and Ca$^{2+}$-transporting ATPase. In one aspect, the population the cells express cardiac calcium handling proteins. Examples of calcium channel proteins include, but are not limited to ryanodine receptor (RyR), calsequestrin, junctin, triadin, phospholamban. In one aspect, the cell expresses on or more calcium pump proteins, sarco/endoplasmic reticulum CA$^{2+}$-ATPase (SERCA) protein, and/or reduced expression of the Na$^+$/Ca$^{2+}$ exchanger (NCX) protein in the cell.

In one aspect of the disclosure including all of the above embodiments, the source cells are comprised of embryonic stem cells, iPSCs or pluripotent stem cells. In another aspect of the disclosure including all of the above embodiments, the substantially homogeneous population of cells are comprised of mammalian cells. In a further embodiment, the mammalian cells are human cells. Compositions and methods to differentiate stem cells to cardiac cells are known in the art, e.g., U.S. Pat. No. 6,387,369 and U.S. Patent Application Publication No. 2007/0025972 A1.

This disclosure also provides a population of cells that have been differentiated from electrophysiologically immature cells and modified as described above, wherein the cells further express a cardiomyocyte marker selected from, but not limited to, myosin heavy chain, myosin light chain, actinin, troponin and tropomyosin, and/or a cardiac calcium handling protein. In another aspect, the cardiomyocytes may be further differentiated into atrial cardiomyocytes or ventricular cardiomyocytes. In another aspect of the invention, including all of the above embodiments, the population of cells that have been differentiated from electrophysiologically immature cells are comprised of embryonic stem cells or pluripotent stem cells. In another aspect of the invention including all of the above embodiments, the population of cells that have been differentiated from electrophysiologically immature cells are comprised of mammalian cells. In a further embodiment, the mammalian cells are human cells. Compositions and methods to differentiate stem cells to cardiac cells are known in the art, e.g., U.S. Pat. No. 6,387,369 and U.S. Patent Application Publication No. 2007/0025972 A1.

Yet another embodiment of the invention is a composition of any one of the above-noted independent modifications and a carrier. In another further embodiment, the carrier is, but not limited to, a biocompatible scaffold, or a pharmaceutically acceptable carrier.

Further provided by this invention are any one or more combinations of the above-noted independent modifications. Thus, Applicants' invention includes any one or more combination of the independently described modifications. The preferred modification or combination of modifications will be determined by the use of the modified cells and in some aspects, the patient to be treated with the modified cell or population of cells.

Also provided by this invention is a population of differentiated cells produced by propagating the above-noted isolated cell(s) or substantially homogeneous population of cells. In one aspect, the cells and/or populations are propagated under conditions that produce immature or mature cardiomyocytes, atrial cells or ventricular cells. These methods are known to those skilled in the art and are described, for example in Xue et al. (2005) Circulation 111:11-20, Moore et al. (2005) Reproductive Toxicology 20:377-391, and Wang et al. (2005) Stem Cells 23:1526-1534.

In a separate aspect, they are propagated under conditions that produce clonal populations of substantially identical or identical cells.

Methods to Produce Modified Cells and Populations of Cells

In one aspect, the disclosure provides a method for inducing expression of the Kir2.1 gene in a cell lacking functional Kir2.1 gene expression, with the proviso that the method excludes genetic manipulation of the cell, comprising, or alternatively consisting essentially of, or yet further consisting of, administering to the cell an effective amount of electrical pacing, thereby inducing expression of Kir2.1 gene expression in the cell.

In another aspect, a method is provided for inducing an electrophysiologically mature phenotype in a cell that is not terminally differentiated, comprising, or alternatively consisting essentially of, or yet further consisting of, administering to the cell that is not terminally differentiated an effective amount of electrical pacing, thereby inducing an electrophysiologically mature phenotype in the cell. In one aspect, the method excludes genetic manipulation of the cell to enhance or increase Kir2.1 expression.

In another aspect, a method for preparing an electrophysiologically mature cardiomyocyte from a cell that is not terminally differentiated, comprising, or alternatively consisting essentially of, or yet further consisting of, administering to the cell that is not terminally differentiated, an effective amount of electrical pacing, thereby preparing an electrophysiologically mature cardiomyocyte. In one aspect, the method excludes genetic manipulation of the cell to enhance or increase Kir2.1 expression and other cardiac ion channels, e.g., the Ca handling proteins.

Cells that can be used in the method include cells that are not terminally differentiated, e.g., an embryonic stem cell, a pluriopotent stem cell, an embryoid body, a mesodermal cardiosphere or an induced pluripotent stem cell.

In one aspect, the electrophysiologically mature cardiomyocyte exhibits one or more of a decrease of the atrial natriuretic factor (ANF) and/or an increase in one or more of the contractile proteins MHCα, MHCβ, MLC2a, MLC2v, cardiac calcium handling proteins.

In another aspect, the electrophysiologically mature cardiomyocyte comprises a cardiac cell of the group of a ventricular cell, an atrial cell. The cell is a mammalian cell, e.g., a murine cell, a bovine cell, a canine cell, a feline cell, an equine cell or a human cell.

In any of the above methods, the electrical pacing comprises a pulsed electrical current of about 2.5 v/cm, for about 5 msec at a width of 1 HZ. In another aspect, the electrical pacing comprises a pulsed electrical current of about 1, 2.5, 10, etc. v/cm, for about 2, 5, 10 msec, etc. at a frequency of 1, 2, 3, 10 HZ etc for various durations (1, 3, 5, 7 days, 2, 3, 4 weeks, etc.).

Further provided is an isolated cell prepared by the method as described above herein. In one aspect, the cell can be expanded or cultured to produce a population of cells that in one aspect, are substantially homogenous. In a further aspect, the substantially homogenous population is a clonal population. After the cell has been modified by a method as disclosed herein, it may be expanded to a substantially homogenous population (e.g., a clonal population) of these cells or alternatively, differentiated to a more mature cell type. Compositions containing these cells and populations of cells are also provided by this disclosure.

Thus, in one aspect, this invention provides an isolated electrophysiologically immature cell, such as an embryonic stem cell or pluripotent stem cell or their derivatives, that has been modified to provide a mature electrophysiological phenotype. The invention also provides for a clonal population or a population of cells differentiated from electrophysiologically immature cells to provide a mature electrophysiological phenotype. In one aspect, the cells or tissues are further characterized by not being modified in one or more of the following manners: by transduction of a polynucleotide that promotes or inhibits $I_{K1}$ activity of the cells; by transduction of a polynucleotide that modulates Kir2 and CSQ protein expression; by transduction of a polynucleotide that encodes a Connexin protein or enhances the expression of a Connexin protein; and by transduction of a polynucleotide that modifies other critical electrophysiological activties of the cells such as $I_{Kr}$, $I_{Ks}$, $I_{Na}$, $I_{Ca}$, $I_{to1}$, $I_{NaCa}$, $Na_{NaK}$ and $I_{pCa}$.

Detection

One can determine if the cell is a more mature cell by using methods known in the art, e.g., by traditional hybridization techniques, immunohistochemistry or PCR. Specific examples include hybridization to DNA microarrays, in situ hybridization, PCR, RNase protection assays and Northern blot analysis. Alternatively expression of the encoded polypeptide can be detected using antibodies that specifically recognize and bind the polypeptide or protein. Such antibodies are useful for visualizing cells that express the polypeptide using techniques such as immunohistology, ELISA, and Western blotting.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention. The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the $V_L$, $V_H$, $C_L$ and CH, domains;

a F(ab')2 fragment, a bivalent fragment comprising two Fab fragments linked by a disulfide bridge at the hinge region; a Fd fragment consisting of the $V_H$ and $C_H$, domains; a Fv fragment consisting of the $V_L$ and $V_H$ domains of a single arm of an antibody, a dAb fragment (Ward et al. (1989) Nature 341:544-546), which consists of a $V_H$ domain; and an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)). Bird et al. (1988) Science 242:423-426 and Huston et al. (1988) Proc. Natl. Acad Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

Various antibody preparations can also be used in analytical methods such as ELISA assays or Western blots to demonstrate the expression of proteins encoded by the identified genes by test cells in vitro or in vivo. Fragments of such proteins generated by protease degradation during metabolism can also be identified by using appropriate polyclonal antisera with samples derived from experimental samples.

Compositions

This invention also provides compositions containing the cells, population of cells and/or differentiated cells in combination with a carrier, such as a biocompatible scaffold or a pharmaceutically acceptable carrier. In one embodiment, the composition is intended for therapeutic use and therefore, an effective amount of the modified cell, population of cells or differentiated cells are provided in the composition.

Uses of the Cells and Cell Populations

Yet another embodiment of the invention is a method for restoring cardiac function in a tissue or host in need thereof. This and other therapeutic uses are described herein.

In one embodiment, the invention provides methods for regenerating cardiac muscle tissue by growing an effective amount of the modified cell or population of immature cells described above. Yet another embodiment of the invention is a method for regenerating cardiac muscle tissue by growing an effective amount of a substantially homogeneous population of immature cells described above.

Yet another embodiment of the invention is a method for regenerating cardiac muscle tissue in a suitable host by administering to the host an effective amount of the isolated cell or population of cells as described above.

A further embodiment of the invention is the host is a mammalian patient and the isolated cell is mammalian. In another embodiment, the host is a human patient and the isolated cell is human.

Another embodiment of the invention is a method for regenerating cardiac muscle tissue in a suitable host by administering to the host an effective amount of an isolated electrically paced cell as described herein. In a further embodiment the host is a mammalian patient and the isolated cell is mammalian. In another embodiment, the host is a human patient and the isolated cell is human.

Another embodiment of the invention is a method of improving cardiac function in a patient in need thereof by the administration of an effective amount of an electrically paced cell as described herein to provide the phenotype of an electrophysiologically mature cell. The patients of this embodiment are suffering from a disease or disorder associated with cardiac malfunction including, but not limited to, congestive heart failure, isolated diastolic heart failure, myocardial infarction, and cardiac arrhythmia. There are several forms of cardiac arrhythmia that can be treated including, but not limited to, sick sinus syndrome, bradyarrhythmia, abnormal sinus node function, atrioventricular block, and atrial and ventricular tachyarrhythmia.

Administration of the cells or compositions can be effected in one dose, continuously or intermittently throughout the course of treatment. Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. Suitable dosage formulations and methods of administering the agents are known in the art. In a further aspect, the cells and composition of the invention can be administered in combination with other treatments.

The cells and populations of cell are administered to the host using methods known in the art and described, for example, in U.S. Pat. No. 6,638,369. This administration of the cells or compositions of the invention can be done to generate an animal model of the desired disease, disorder, or condition for experimental and screening assays.

Screening Assays

The present invention provides methods for screening various agents that modulate cardiac function and for studying cardiac function in vitro. For the purposes of this invention, an "agent" is intended to include, but not be limited to a biological or chemical compound such as a simple or complex organic or inorganic molecule, a peptide, a protein (e.g., antibody), a polynucleotide (e.g., anti-sense) or a ribozyme. A vast array of compounds can be synthesized, for example polymers, such as polypeptides and polynucleotides, and synthetic organic compounds based on various core structures, and these are also included in the term "agent." In addition, various natural sources can provide compounds for screening, such as plant or animal extracts, and the like. It should be understood, although not always explicitly stated that the agent is used alone or in combination with another agent, having the same or different biological activity as the agents identified by the inventive screen.

To practice the screening method in vitro, suitable cell cultures or tissue cultures containing the modified cell(s) are first provided. When the agent is a composition other than a DNA or RNA, such as a small molecule as described above, the agent can be directly added to the cell culture or added to culture medium for addition. As is apparent to those skilled in the art, an "effective" a mount must be added which can be empirically determined. When agent is a polynucleotide, it can be directly added by use of a gene gun or electroporation. Alternatively, it can be inserted into the cell using a gene delivery vehicle or other method as described above. Positive and negative controls can be assayed to confirm the purported activity of the drug or other agent.

The following examples are intended to illustrate and not limit the inventions as provided herein.

Culture and Directed Differentiation

HES2 human ESC line (ESI, Singapore) was cultured and differentiated by co-culturing with the immortalized endoderm-like END2 cells as previously reported (Mummery, C. et al. (2003) Circulation 107:2733-2740; Reubinoff, B. E. et al. (2000) Nat. Biotechnol. 18:399-404). H1 human ESC line (WiCell, Madison, Wis.) was cultured and differentiated by embryoid body (EB) formation (Kehat, I. et al. (2001) The Journal of Clinical Investigation 108:407-414; Xu, C. et al. (2002) Circ Res. 91:501-508; He, J. Q. et al. (2003) Circ. Res. 93:32-39) as described previously. Human induced pluripotent stem cells (iPSC ES4skin-clone 3), a kind gift from Dr. James Thomson (Wis., Madison), were also maintained as described (Yu, J. et al. (2007) Science 318:1917-1920). IPSC-CMs were derived via EB formation following the H1 hESC differentiation protocol. D3 murine ESCs were cultivated and differentiated into spontaneously beating CMs as previously described (Wobus, A. M. et al. (2002) Methods Mol. Biol. 185:127-156).

For directed differentiation (dd) of HES2 hESCs into the cardiac lineage, cardiogenic EBs (or mesodermal cardiospheres) were generated for 24 hours in the presence of 0.5 ng/ml BMP4 in STEMPRO 34 media as described (Yang, L. et al. (2008) Nature 453:524-528). From days 1-4 the EBs were induced with 10 ng/ml BMP4, 5 ng/ml bFGF and 3 ng/ml activin A and then from days 4-8, they were cultured in 150 ng/ml DKK1 and 10 ng/ml VEGF. From day 8 onwards the EBs were maintained in the presence of 10 ng/ml VEGF, and 5 ng/ml bFGF. Cultures were maintained in a 5% $CO_2$/5% $O_2$/90% $N_2$ environment for the first 10-12 days and were then transferred into a 5% $CO_2$/air environment. Directed differentiation typically results in aggregates consisting of 40-50% CMs as assessed by expression of cardiac troponin T using FACS. For driven maturation, ddhESCs-CMs of 24-28 days were plated for electrical stimulation at 2.5 V/cm with 5 msec pulse width at 1 Hz for 14 days before experiments.

Adenovirus-Mediated Gene Transfer of Single Derived-CMs

The full-length coding sequence of human Kir2.1 was cloned into the multiple-cloning site of pAd-CMV-IRES-GFP (pAd-GFP) to generate pAd-CMV-GFP-IRES-Kir2.1 (pAd-Kir2.1), where GFP allows for identification of positively transduced cells. Adenoviruses were generated by Cre-lox recombination of purified Ψ5 viral DNA and shuttle vector DNA as previously described (Hardy, S. et al. (1997) J. Virol. 71:1842-1849). The recombinant products were plaque purified, expanded and purified by CsCl gradient, yielding concentrations on the order of $10^{10}$ PFU/ml. For transduction, adenoviral particles were added to single ddhESC-CMs (20~25 days), EB-hESC-CMs (7+14~21 days), END2-hESC-CMs (16~20 days), EB-iPSC-CMs (7+21~24 days) and EB-mESC-CMs (7+4 days) at a concentration of ~2×$10^9$ PFU (Tse, H. F. et al. (2006) Circulation 114:1000-1011).

Electrophysiology

HESC- and hiPSC-CMs were dissociated into single cells with 1 mg/ml collagenase II and plated on 0.1% gelatin-coated glass coverslips. Electrophysiological experiments were performed using whole-cell patch-clamp technique with an Axopatch 200B amplifier and the pClamp9.2 software (Axon Instruments Inc., Foster City, Calif.). Pipette solution was consisted of (mM): 110 $K^+$ aspartate, 20 KCl, 1 $MgCl_2$, 0.1 Na-GTP, 5 Mg-ATP, 5 $Na_2$-phosphocreatine, 1 EGTA and 10 HEPES, with pH of 7.3. The external Tyrode's solution consisted of (mM): 140 NaCl, 5 KCl, 1 $CaCl_2$, 1 $MgCl_2$, 10 glucose, and 10 HEPES with pH of 7.4. Voltage- and current-clamp recordings were performed at 37° C. within 24 to 48 hours after adenovirus transduction. ESC-CMs were categorized into pacemaker, atrial or ventricular phenotypes based on the maximum diastolic potential (MDP), maximum rate of rise of the AP and AP duration (APD). In general, pacemaker cells always generated spontaneous APs exhibiting a more depolarized MDP, slower maximum rate of rise and the shortest APD. Atrial cells with a triangular AP profile have a faster rate of rise than pacemaker cells, more hyperpolarized MDP or resting membrane potential (RMP), and intermediate APD. Ventricular cells have the most hyperpolarized MDP or RMP, a fast rate of rise and the longest APD that exhibited a prolonged AP phase 2. Different protocols as given in insets were employed to elicit the corresponding currents. 5 mM nifedipine, 30 mM tetrodotoxin (TTX), 1 mM $Ba^{2+}$, 30 mM ZD7288, 10 mM E4031 and 30 mM Chromanol 293B were used to define the $I_{caL}$, $I_{Na}$, $I_{K1}$, $I_f$ $I_{Kr}$, and $I_{Ks}$, respectively. All blockers were purchased from Sigma.

Formulation of Cardiac Electrophysiology Mathematical Model

Ionic currents and membrane potential of ventricular CMs were formulated based on an embryonic chick ventricular cell model (Krogh-Madsen, T. et al. (2005) Am. J. Physiol. Heart Circ. Physiol. 289:H398-H413) and according to the algorithms that have been previously reported (Azene, E. M. et al. (2005) Cardiovascular Research 67:263-273). In this model, the six ionic currents initially included based on previous reports (Boheler, K. R. et al. (2002) Circ. Res. 91:189-201) were slow inward $Ca^{2+}$ current ($I_{Ca}$), slow delayed $K^+$ current ($I_{Ks}$), rapid delayed rectifier $K^+$ current ($I_{Kr}$), pacemaker current ($I_f$), background current ($I_b$), and seal-leak current ($I_{seal}$). The kinetics of the currents was derived empirically from experimental data (Krogh-Madsen, T. et al. (2005) Am. J. Physiol. Heart Circ. Physiol. 289:H398-H413). $I_{K1}$ was absent in this base model to simulate Applicants' experimental data and subsequently manipulated to predict the effects of Kir2.1 overexpression. The computations were performed in Matlab (Mathworks, Natick, Mass.) using a variable order ordinary differential equation solver plus a built-in backward-difference method, with relative tolerance of $10^{-8}$ and absolute tolerance of $10^{-4}$.

Confocal $Ca^{2+}$ Imaging

Single-cell $Ca^{2+}$ transients of Fluo-4-loaded ddhESC-CMs were recorded with a spinning disk confocal microscope (Yokogawa CSU10) at ~180 frames per second with a 40× microscope objective at room temperature in Tyrode's solution consisting of (mM): 140 NaCl, 5 KCl, 1 $MgCl_2$, 2 $CaCl_2$, 10 glucose and 10 HEPES at pH 7.4. $Ca^{2+}$ transients were elicited by a field stimulator at 0.2 Hz and 40 V with 90 ms pulse duration. The $Ca^{2+}$ transient changes were quantified by the background subtracted fluorescent intensity changes normalized to the background subtracted baseline fluorescence using Image J.

Quantitative PCR mRNA was extracted from derived CMs using RNeasy Kit (Qiagen, Valencia, Calif.). cDNA were reverse transcribed from mRNA using Quantitect Reverse Transcription Kit (Qiagen). Platinum SYBR Green qPCR SuperMix-UDG (Invitrogen) was used for qPCR analysis with a BioRad iCycler (BioRad, Hercules, Calif.). The expression level was normalized relative to GAPDH using the $\Delta\Delta C_T$ method.

Transmission Electron Microscopy

Unpaced control and electrically conditioned beating cardiospheres from two separate differentiation batches were manually dissected out, then fixed with Karnovsky's fixative at room temperature. Specimens were further fixed with 1% oxmium tetroxide for 90 min. After acetone dehydration, the specimen were infiltrated with epoxy resin and allowed to polymerize at 70° C. overnight. Sections 60 nm thick were stained with uranyl acetate. A total of 15 unpaced control and 13 electrically conditioned cells were imaged with a FEI/Philips CM120 TEM (Philips/FEI, Endhoven, Netherlands).

Statistics

Data are shown as mean±SEM. Unpaired Student's t test or Chi-square ($\chi^2$) test were used for statistical analysis where $p<0.05$ was considered statistical significant.

Results

Figure 1B:
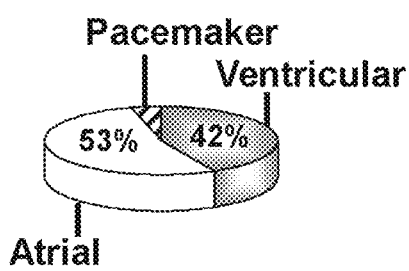
Figure 1C:
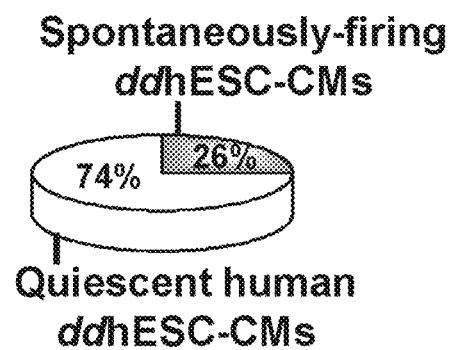
Figure 1D:
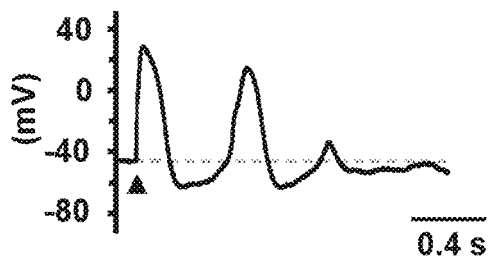
Figure 4A:
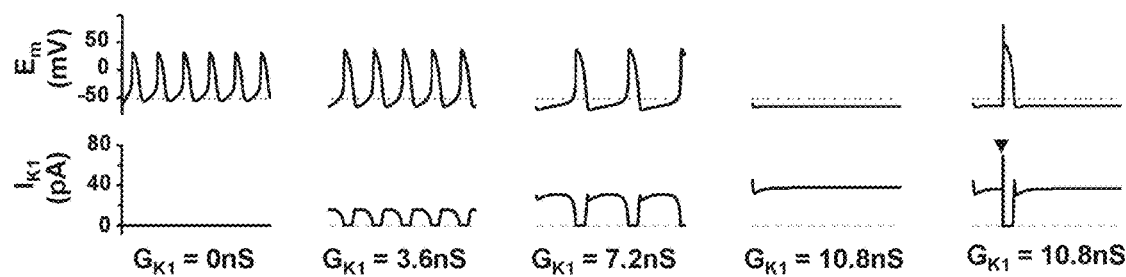
FIGS. 4A-4G show effects of $I_{K1}$ presence on electrophysiology of pluripotent stem cell derived-CMs.

Pro-arrhythmic Properties of Derived CMs are Independent of Cardiogenesis Protocol and Origin of Stem Cell Lines Single ddhESC-CMs from cardiogenic EBs differentiated for 20-25 days were electrophysiologically assessed by whole-cell patch-clamp techniques. The ddhESC-CMs were classified by their ability to generate AP into spontaneously firing and quiescent ddhESC-CMs, and also classified into CM subtypes by the observed signature ventricular, atrial and pacemaker APs (FIG. 1A). Unlike healthy adult CMs, 26% of all ddhESC-CMs displayed a high degree of automaticity or spontaneous firing of APs (FIG. 1C). While the remaining ddhESC-CMs were quiescent, stimulation could elicit a single AP characteristics of ventricular or atrial subtype (FIG. 1A, right), indicating that their excitability remained intact; however, these quiescent-yet-excitable ddhESC-CMs displayed a prominent "phase 4-like" depolarization (FIG. 1A, arrows), a known pro-arrhythmic triggering substrate that is also not seen in mature contractile adult CMs (ten Tusscher, K. H. et al. (2006) Am. J. Physiol. Heart Circ. Physiol. 291:H1088-H1100; Wagner, M. B. et al. (2005) Pediatr. Res. 57:28-34; Wang, Y. et al. (2003) Journal of Molecular and Cellular Cardiology 35:1083-1092). The ddhESC-CM population overall exhibited a distribution of 42% ventricular, 53% atrial and 5% pacemaker CMs (FIG. 1B; n=70). Delayed-after depolarization (DAD) was observed in 23% of quiescent ventricular ddhESC-CMs (FIG. 1D). Furthermore, the resting membrane potentials (RMPs) were significantly more depolarized (FIG. 4E) than ∼−80 mV typical of normal adult (ten Tusscher, K. H. et al. (2006) Am. J. Physiol. Heart Circ. Physiol. 291: H1088-H1100; Wagner, M. B. et al. (2005) Pediatr. Res. 57:28-34; Wang, Y. et al. (2003) Journal of Molecular and Cellular Cardiology 35:1083-1092) and comparable to ∼−53 mV typical of immature human fetal ventricular CMs of 18 weeks.

Figure 1E:
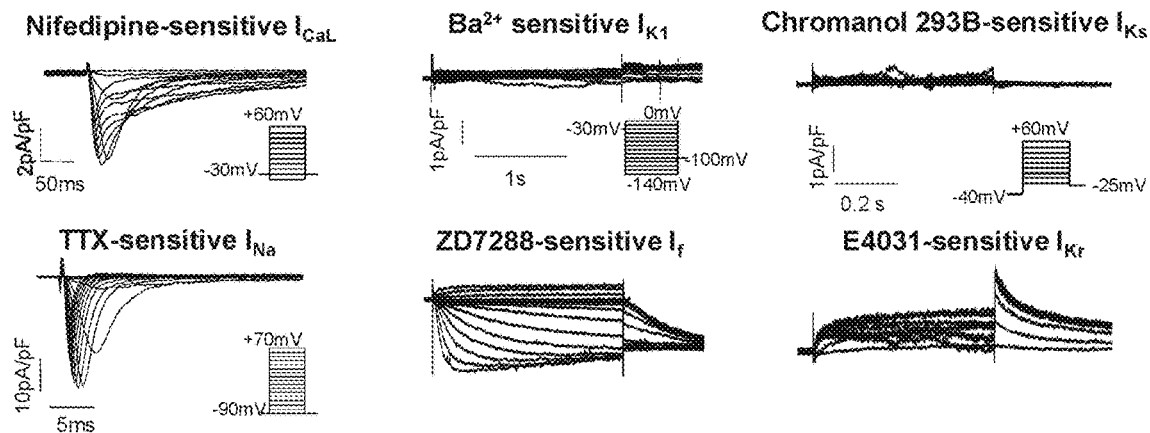
Figure 2A:
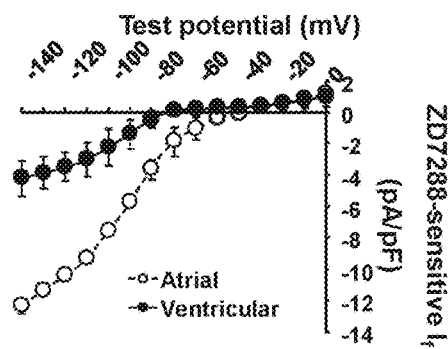
FIGS. 2A-2F show current-voltage, activation and inactivation relationships of currents in ddhESC-CMs.
Figure 2B:
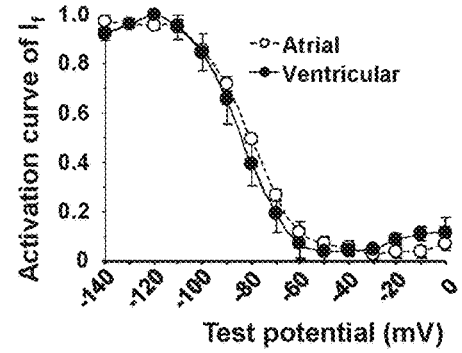
Figure 2C:
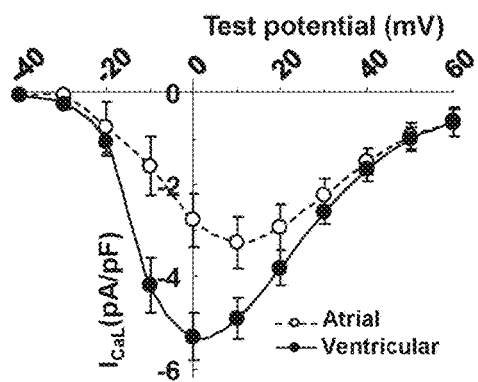
Figure 2D:
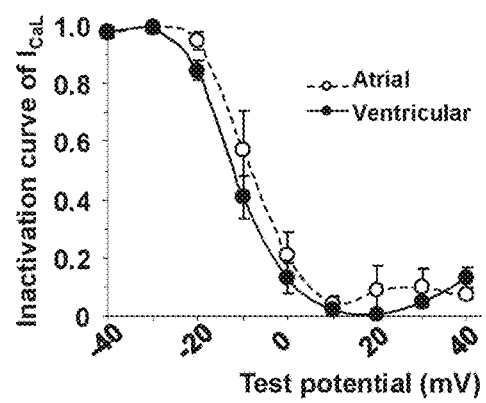
Figure 2E:
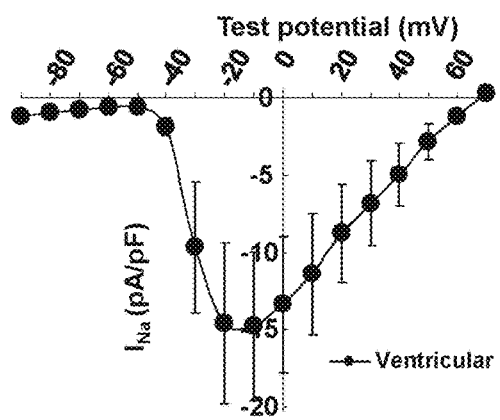
Figure 2F:
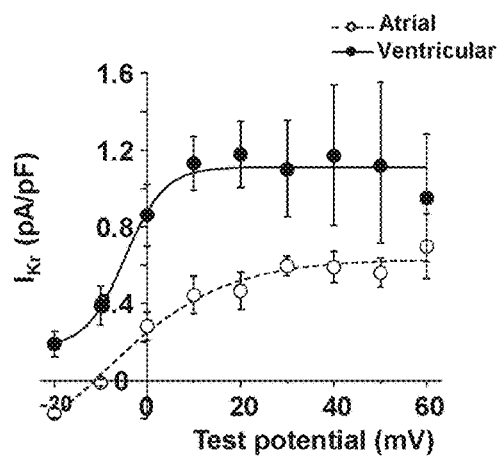

Given the potential for myocardial repair, Applicants next focused on analyzing ventricular ddhESC-CMs. To understand the electrophysiological basis of the observed AP phenotypes, Applicants functionally profiled the individual ionic components present (FIG. 1E and FIG. 2). Ventricular ddhESC-CMs robustly expressed $I_{Na}$, $I_{CaL}$ and $I_{to}$ (Yang, L. et al. (2008) Nature 453:524-528), which are comparable to adult ventricular CMs. $I_f$ that is typically not seen in healthy adult ventricular CMs (except in immature or pathophysiological states such as hypertension and heart failure) was highly expressed in both atrial and ventricular ddhESC-CMs with a higher current density for the atrial relative to ventricular subtype, but their steady-state activation curves were identical (FIGS. 2A and 2B). $I_{CaL}$ was present at higher current density in ventricular relative to atrial ddhESC-CMs with similar steady-state inactivation properties (FIGS. 2D and 2D). However, the inwardly rectifying $K^+$ current ($I_{K1}$) and slow ($I_{Ks}$) components of the delayed rectifier that are present in high current density in adult CMs for repolarization were not present in ventricular ddhESC-CMs. Although not as robust as the adult counterpart, the rapid component of the delayed rectifying $K^+$ current ($I_{Kr}$) was expressed in both atrial and ventricular ddhESC-CMs with a slightly higher current density in the latter (FIG. 2F).

Figure 1F:
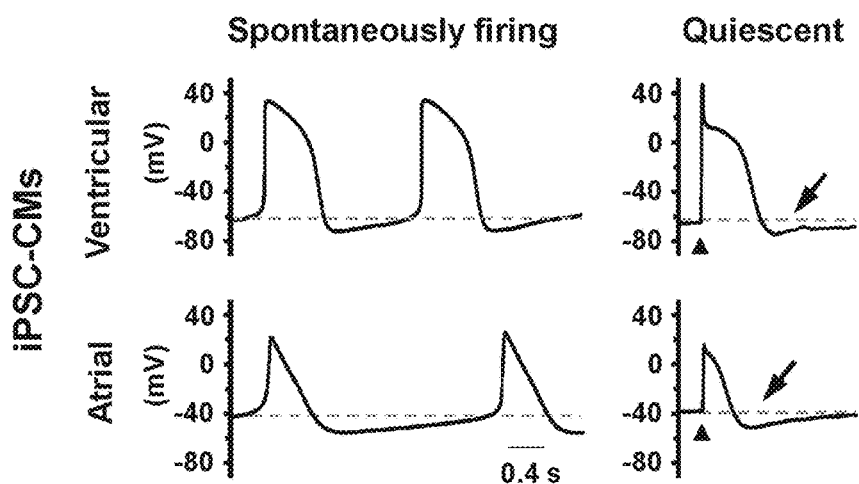
Figure 3A:
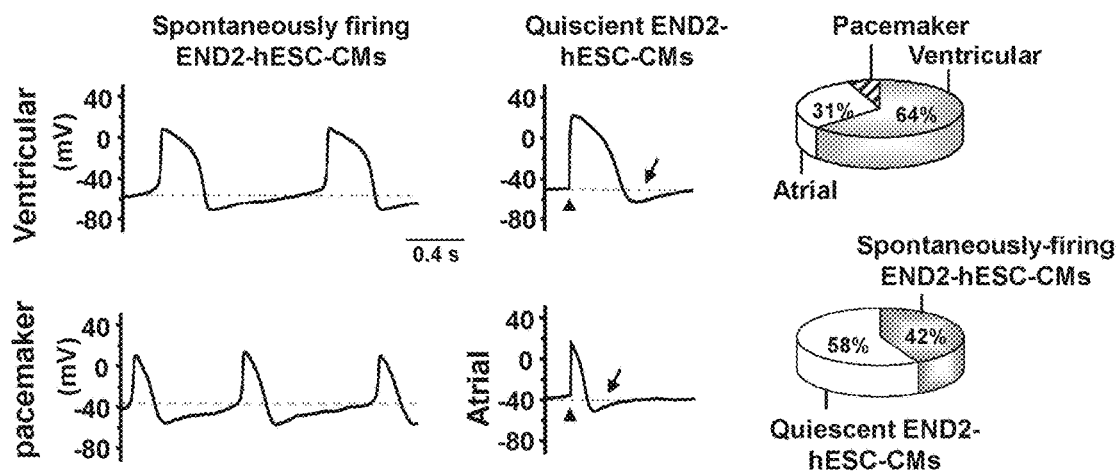
FIGS. 3A-3D show electrophysiological properties of hESC-CMs derived from the HES2 and H1 lines.
Figure 3B:
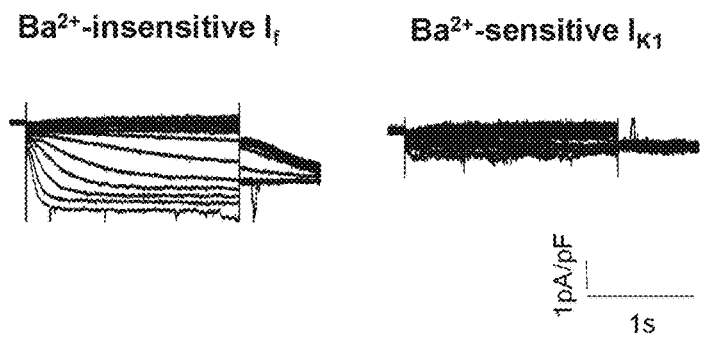
Figure 3C:
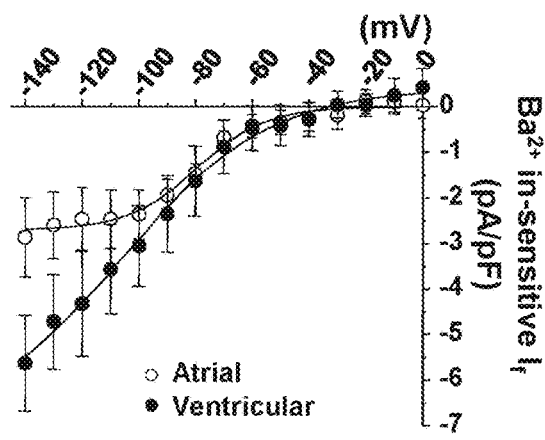
Figure 3D:
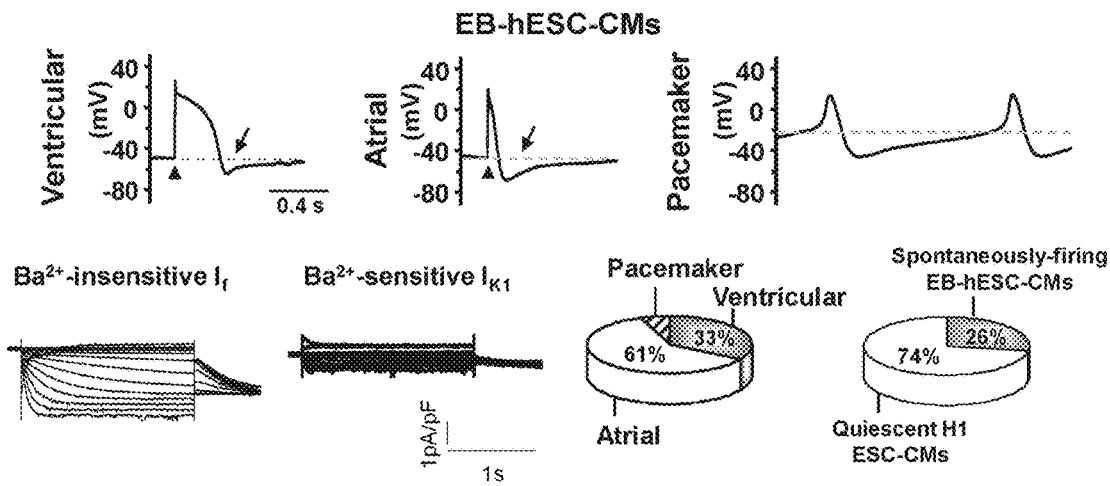

Inductive interactions among the three primitive germ layers figure prominently in embryogenesis (Saxen, L. (1975) Clin. Obstet. Gynecol. 18:149-175), the first step of ddhESC-CMs derivation involved directed mesodermal differentiation (Yang, L. et al. (2008) Nature 453:524-528). Considering the method of induction as well as the specific hESC line may influence the type of CMs that develops (Moore, J. C. et al. (2008) Biochem. Biophys. Res. Commun. 372:553-558), Applicants next examined and compared electrophysiology of hESC-CMs derived by two distinct methods: 1) endodermal induction with END2 co-culturing of the HES2 (END2-hESC-CMs) (Mummery, C. et al. (2003) Circulation 107:2733-2740) and 2) EB formation of the H1 hESC lines (EB-hESC-CMs) (Kehat, I. et al. (2001) The Journal of Clinical Investigation 108:407-414). Like the ddhESC-CMs, immature AP properties such as automaticity, phase 4-like depolarization, depolarized RMP, the presence of DAD and $I_f$, and the absence of $I_{K1}$ were all commonly observed in both END2- (FIGS. 3A-3C) and EB-hESC-CMs (FIG. 3D). Even human induced pluripotent stem cell (Yu, J. et al. (2007) Science 318:1917-1920) (iPSC)-derived CMs by EB formation behaved similarly (FIG. 1F). Taken together, these data suggest that the immature, pro-arrhythmic AP properties are genuine developmental hallmarks of early stage human CMs derived in vitro. Unfortunately, derived CMs failed to mature further even after culturing for >100 days (Sartiani, L. et al. (2007) Stem Cells 25:1136-1144). These data hint at the intriguing possibility that a crucial physical component that drives hESC-CM maturation in vivo is missing in the conventional method of in vitro culture.

$I_{K1}$ is a Major Mechanistic Contributor to the Immature AP of hESC-CMs

In normal fetal CM development, one of the major electrophysiological changes is a progressive increase in $I_{K1}$ and concomitant reduction in $I_f$ (Nass, R. D. et al. (2008) Nat. Clin. Pract. Cardiovasc. Med. 5:196-207). In heart failure, the fetal gene program is re-initiated in adult CMs to cause electrical remodeling (Beuckelmann, D. J. et al. (1993) Circulation Research 73:379-385), such that $I_{K1}$ becomes down-regulated whereas $I_f$ is reciprocally upregulated, thereby predisposing the afflicted individuals to lethal arrhythmias. Along this line, Applicants data collectively hint at three possible mechanisms for the immature AP phenotypes: the presence of $I_f$, the absence of $I_{K1}$, or both. To understand the basis of electrical immaturities and thereby develop a strategy for maturing and eliminating the undesirable proarrhythmic traits of derived CMs, Applicants next performed an in silico analysis of the AP profiles (FIG. 4A) (Krogh-Madsen, T. et al. (2005) Am. J. Physiol. Heart Circ. Physiol. 289:H398-H413; Azene, E. M. et al. (2005) Cardiovascular Research 67:263-273). By incorporating all the ionic components identified (FIG. 1E), Applicants ventricular model sufficed to reproduce the experimentally determined AP parameters. When the maximum conductance of $I_{K1}$ ($G_{K1}$) was increased from 0, the experimentally observed level, to 3.6 nS (i.e., ⅛ of that of adult ventricular cells) and subsequently to 7.2 nS, the firing rate decreased accordingly. When $G_{K1}$ was 10.8 nS or higher, the spontaneous firing ceased along with RMP hyperpolarized to the adult level; these $I_{K1}$-silenced cells remained excitable and could generate a normal ventricular AP when triggered by a stimulus. Silencing could not be achieved by $I_f$ suppression alone; thus, according to Applicants' model, the absence of $I_{K1}$ appears to be a major mechanistic contributor of pro-arrhythmic automaticity.

Figure 4B:
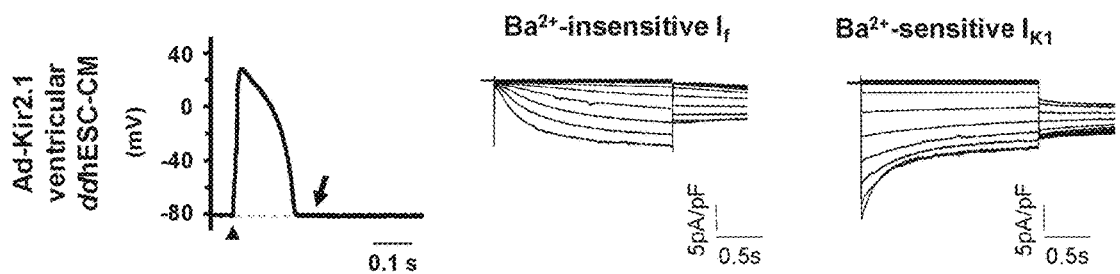
Figure 4C:
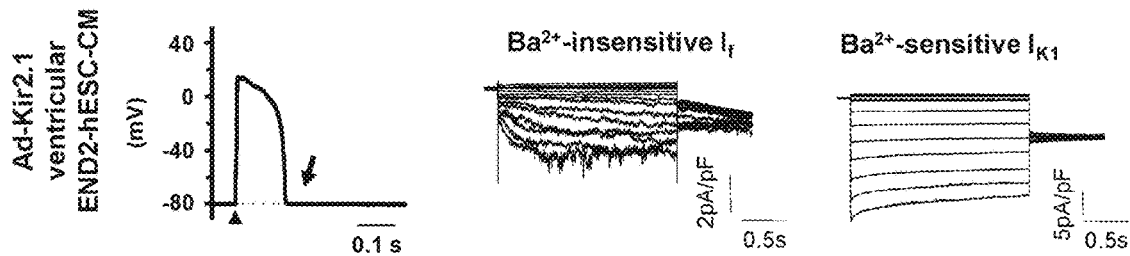
Figure 4D:
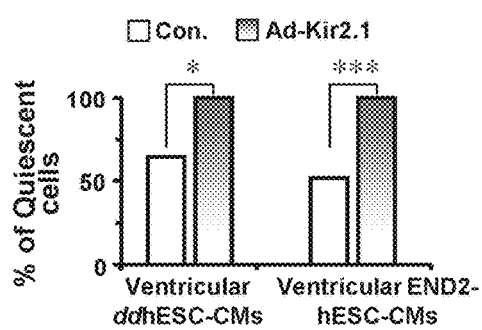
Figure 4E:
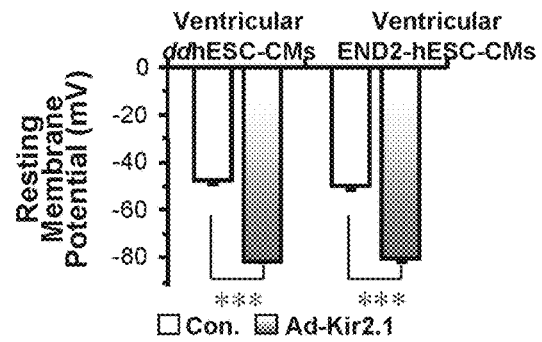
Figure 4F:
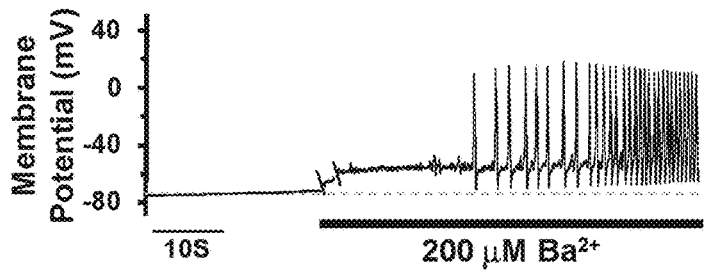
Figure 4G:
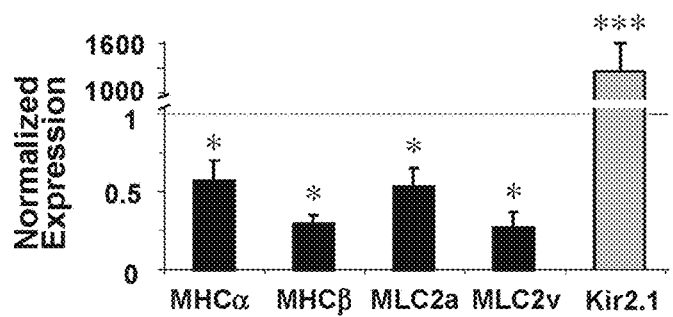

To experimentally test Applicants' mathematical modeling results, Applicants generated the recombinant adenovirus Ad-CMV-GFP-IRES-Kir2.1 (or Ad-Kir2.1) to mediate the expression of Kir2.1 channels that underlie $I_{K1}$ (Yang, J. et al. (1995) Neuron. 15:1441-1447). In contrast to untransduced or Ad-GFP-transduced $I_{K1}$-negative control, Ad-Kir2.1-transduced ventricular ddhESC-(n=7) and END2-hESC-(n=13) CMs robustly expressed $Ba^{2+}$-sensitive $I_{K1}$ (FIGS. 4B, 4C and 4G). More importantly, the percentages of quiescent ventricular ddhESC- and END2-hESC-CMs dramatically increased to 100% (FIG. 4D; p<0.05) with their RMP significantly hyperpolarized (p<0.05, FIG. 4E) to the adult level (p>0.05). Ad-Kir2.1-silenced cells remained excitable and could generate a single AP upon stimulation, but most importantly, the phase 4-like depolarization was completely eliminated (FIGS. 4B and 4C, arrow). Interestingly, Ad-Kir2.1-silenced ventricular ddhESC-CMs reverted back to the spontaneously firing phenotype upon the addition of an $I_{K1}$ blocker, $Ba^{2+}$ (FIG. 4F). Kir2.1 expression also sufficed to mature the AP profiles of atrial ddhESC- and END2-hESC-CMs (FIGS. 5A-5D).

Figure 8A:
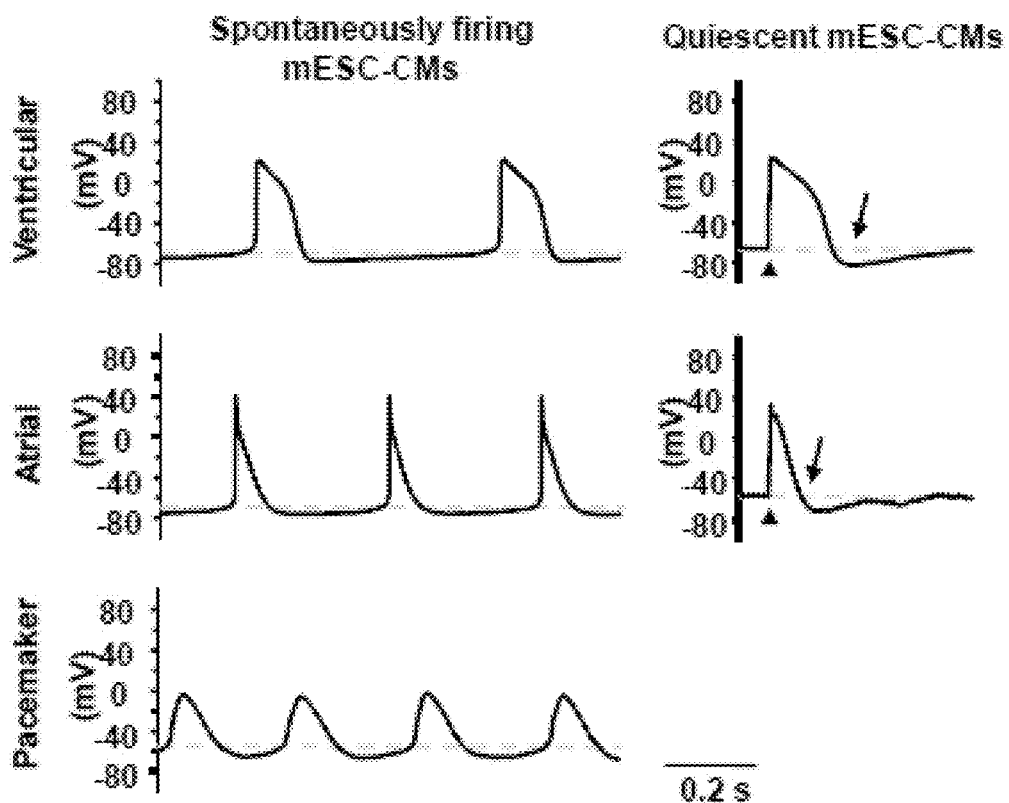
FIGS. 8A and 8B show immature electrophysiological properties of mouse (m)ESC-CMs.
Figure 8B:
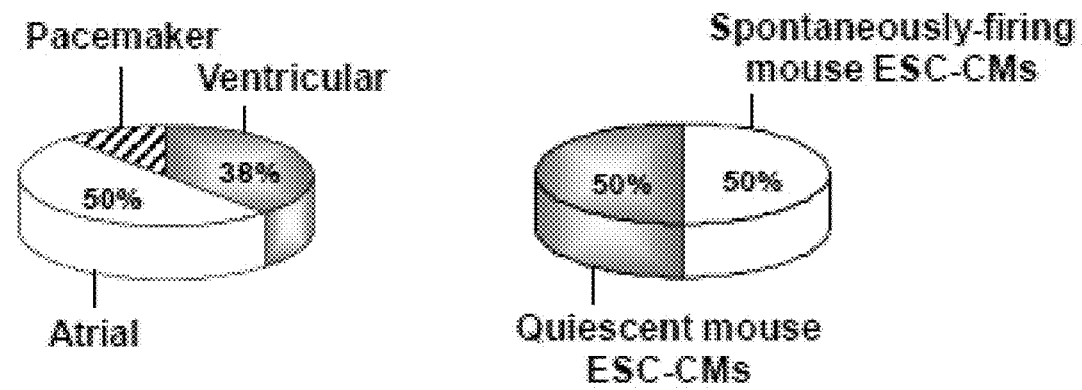
Figure 9A:
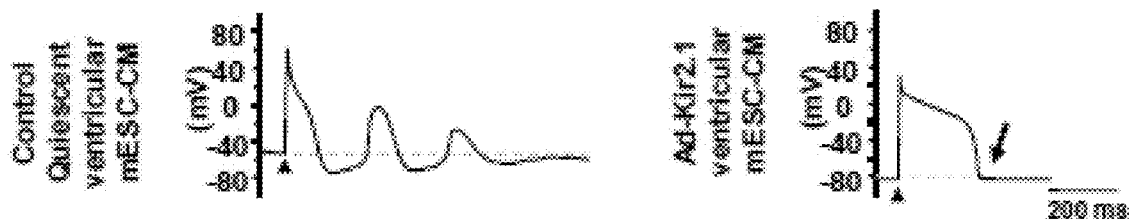
Figure 9B:
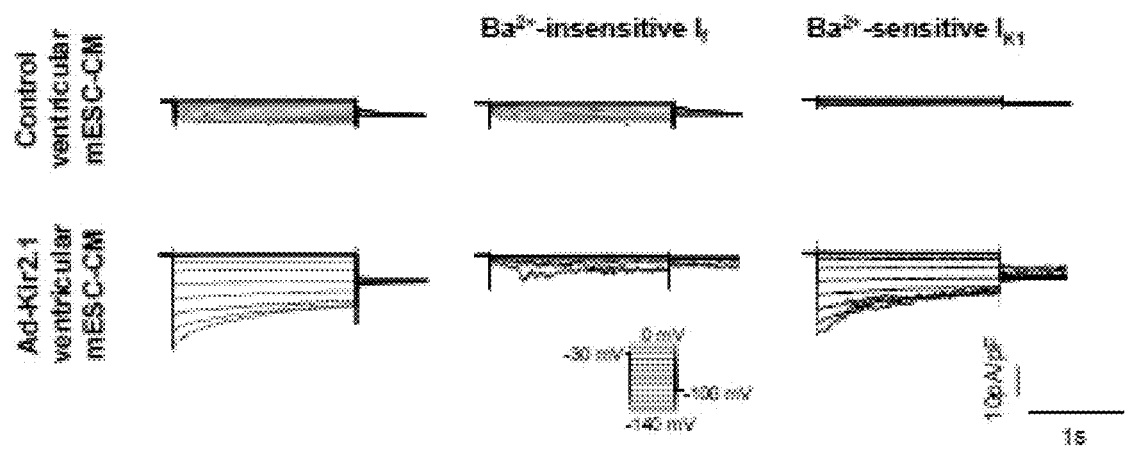
Figure 9C:
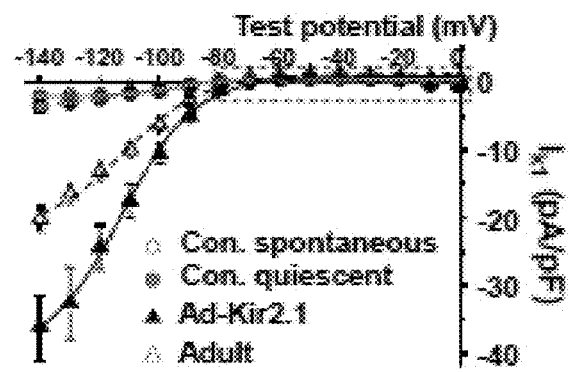
Figure 10B:
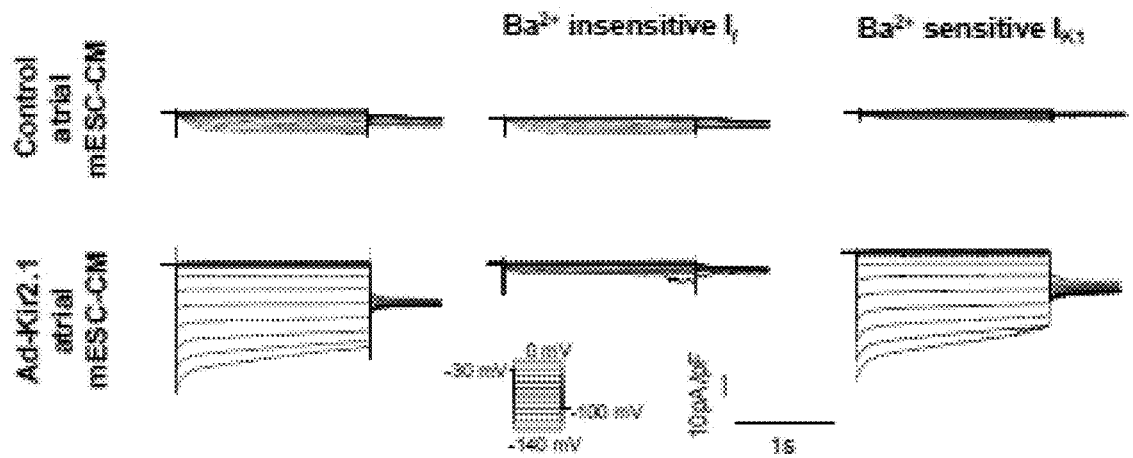
Figure 10C:
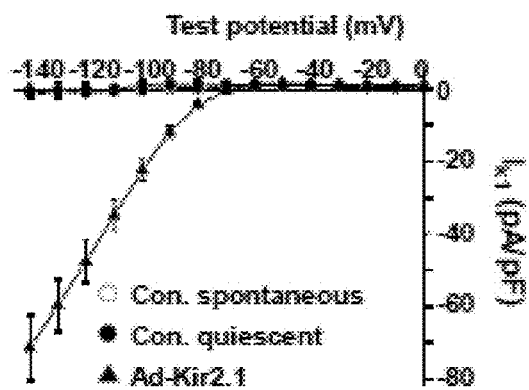
Figure 10D:
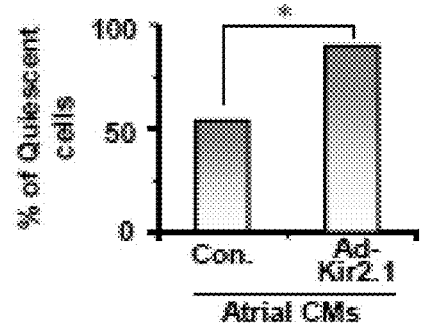
Figure 10E:
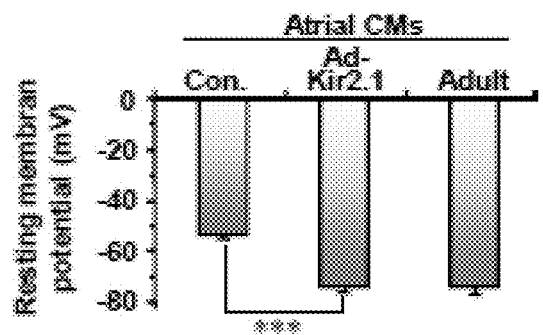

Similar to their human counterparts, murine (m) ventricular and atrial ESC-CMs exhibited comparably immature electrophysiological properties (FIGS. 8A and 8B) that could likewise be rendered adult-like by Kir2.1 expression (FIGS. 9A-9F and 10A-10E). These data collectively indicate that Applicants' observations of electrophysiological immaturities in the derived CMs were a general phenomenon and not cell line-, species- or protocol-dependent.

Physiological Pacing Facilitates Maturation of hESC-CMs In Vitro

Figure 6A:
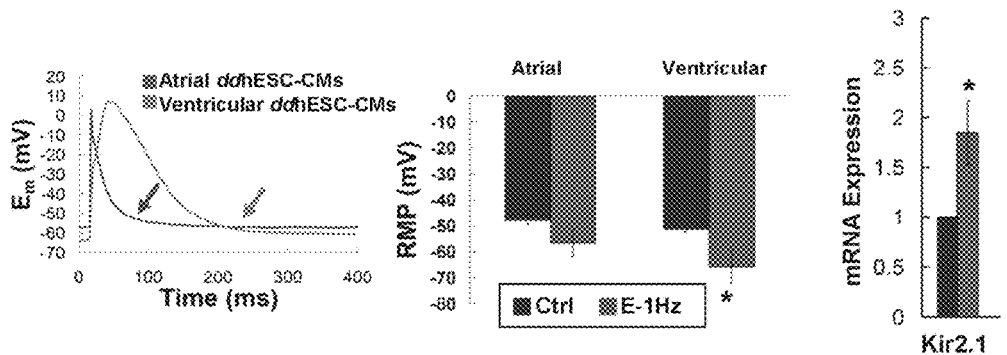
Figure 6B:
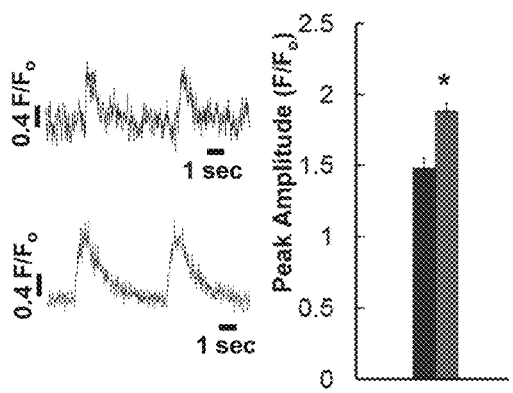
Figure 6C:
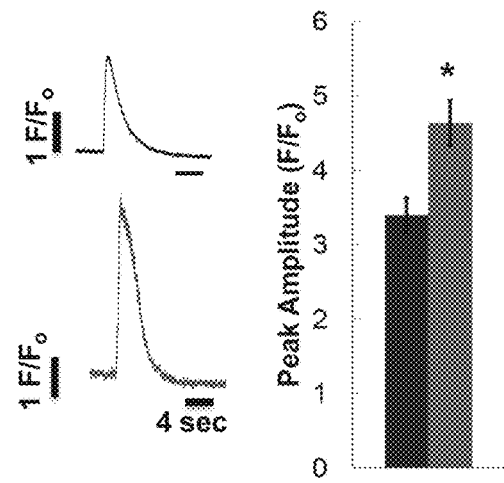
Figure 6D:
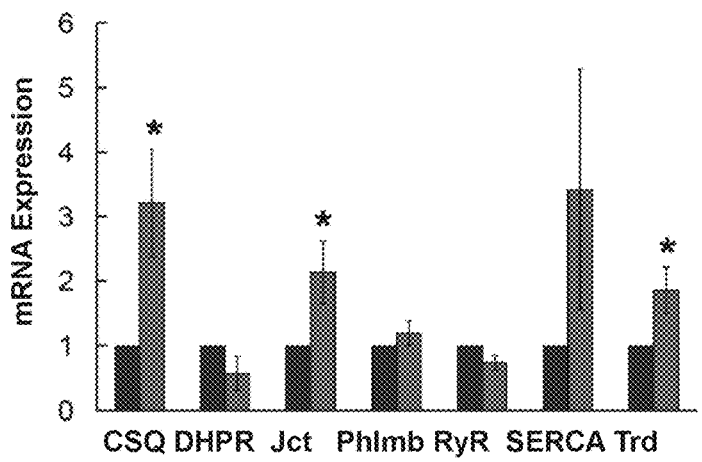
Figure 11:
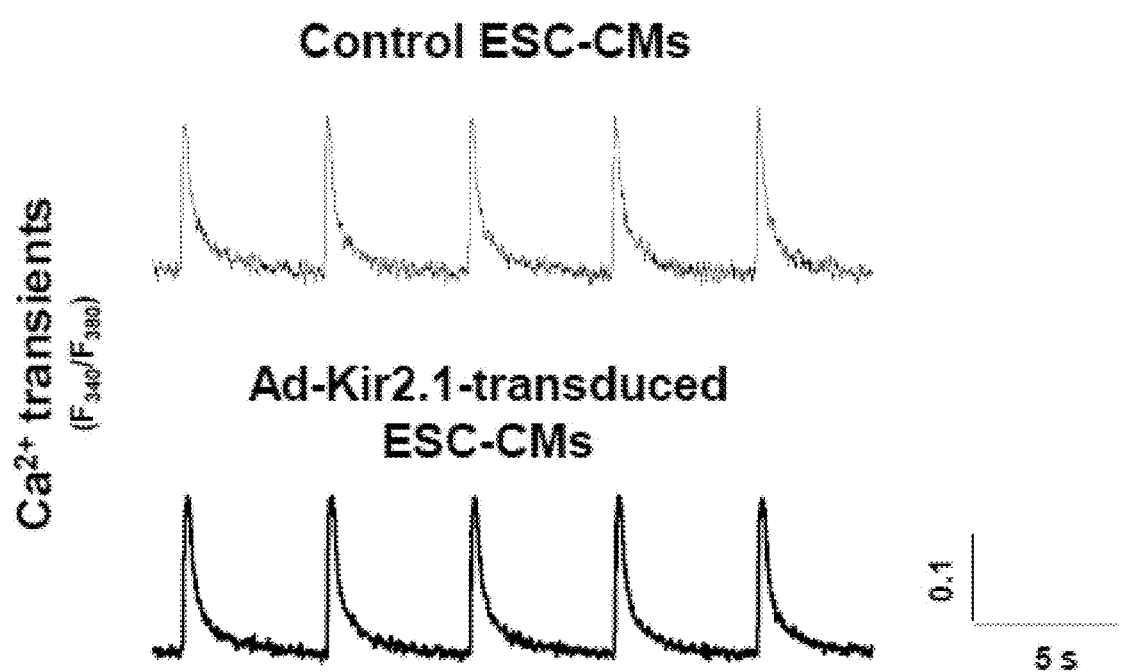
FIG. 11 shows representative tracings of $Ca^{2+}$ transients in control and Ad-Kir2.1-transduced mESC-CMs overexpressing Kir2.1. No significant differences in $Ca^{2+}$ transients were observed.
Figure 12A:
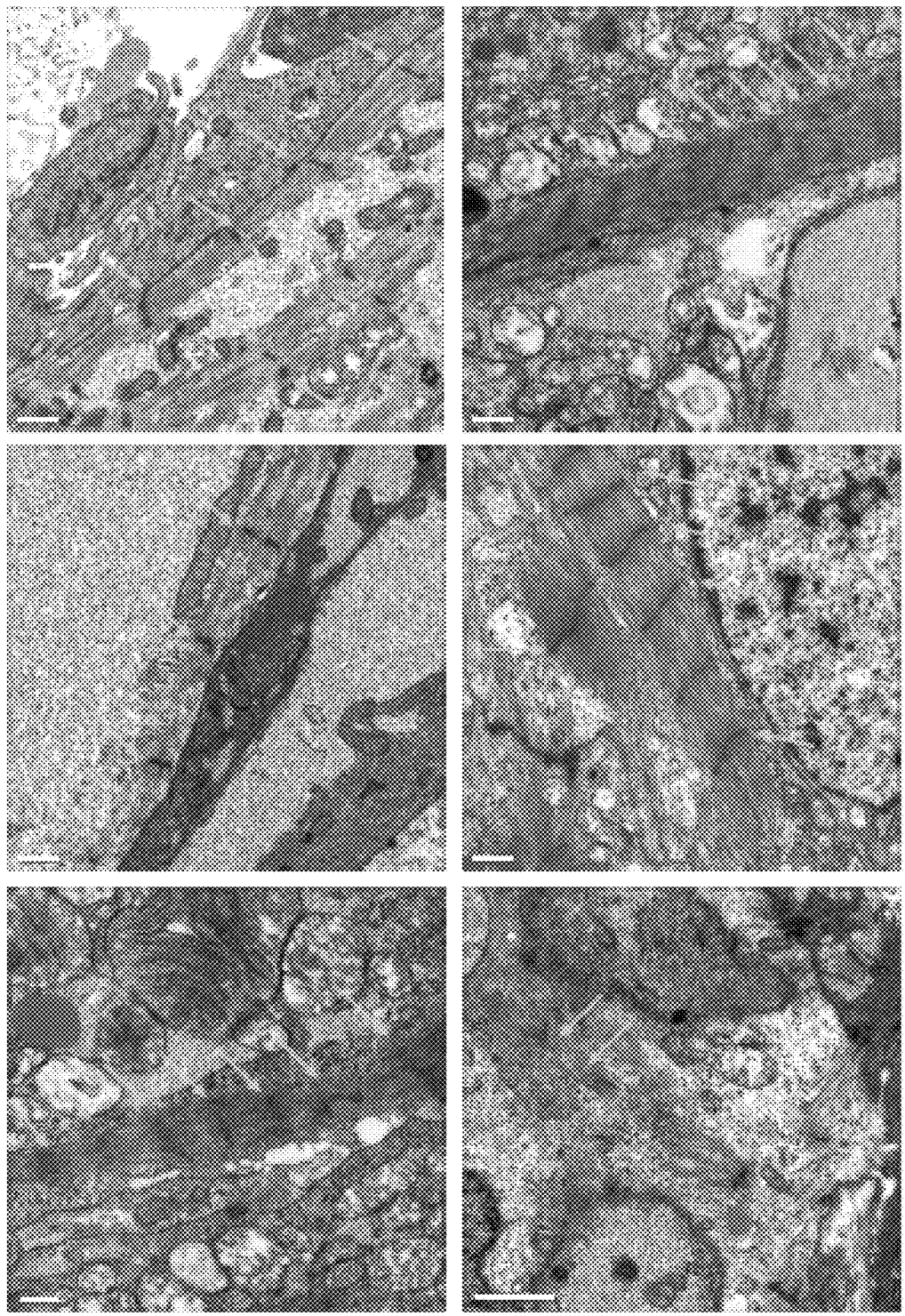
FIGS. 12A and 12B show transmission electron microscopy images of the additional (FIG. 12A) unconditioned ddhESC-CMs showed myofibrils that are less dense and less organized than (FIG. 12B) the electrically conditioned ddhESC-CMs. The z-lines (arrows) can be seen in both groups.
Figure 12B:
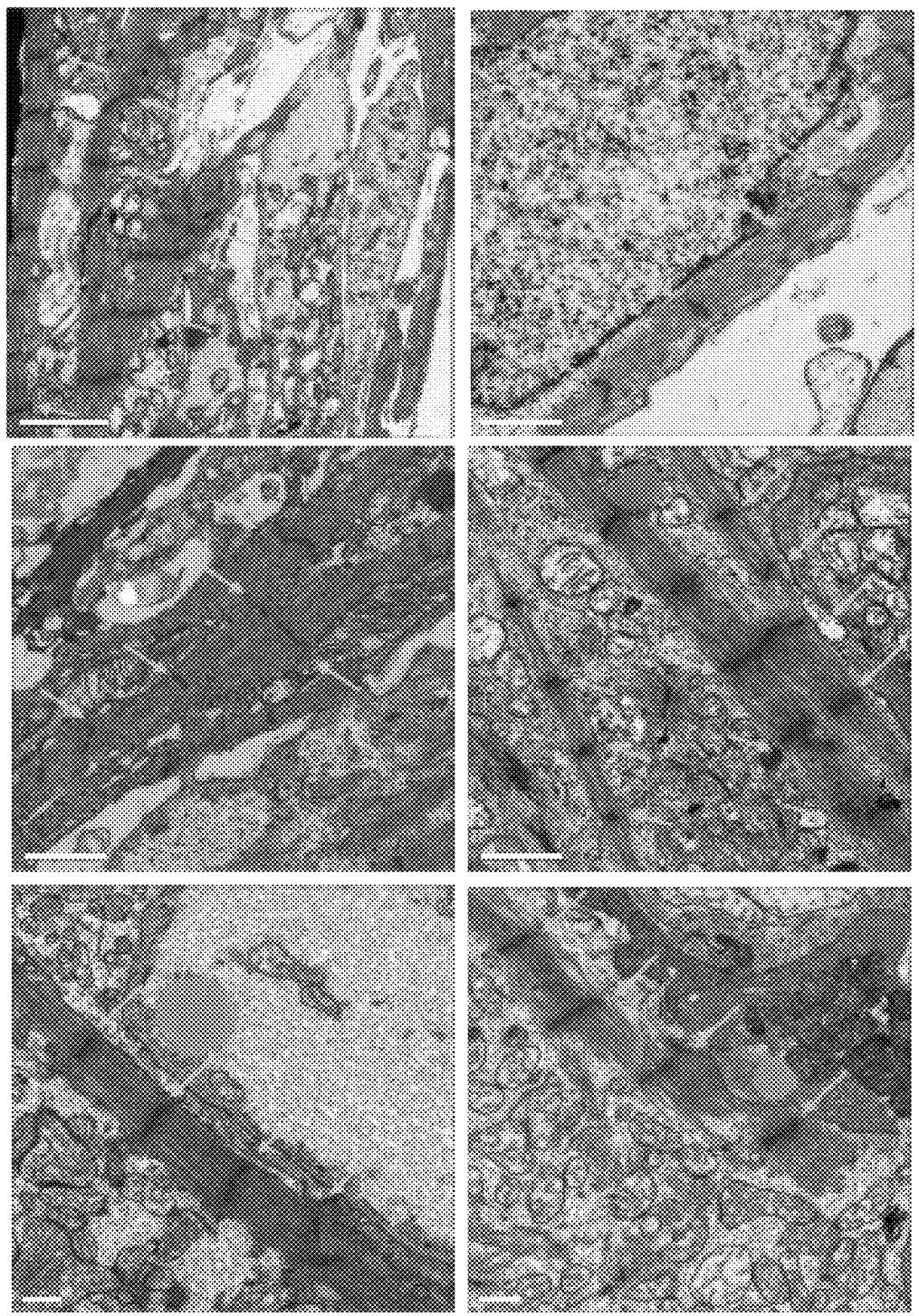
Figure 13A:
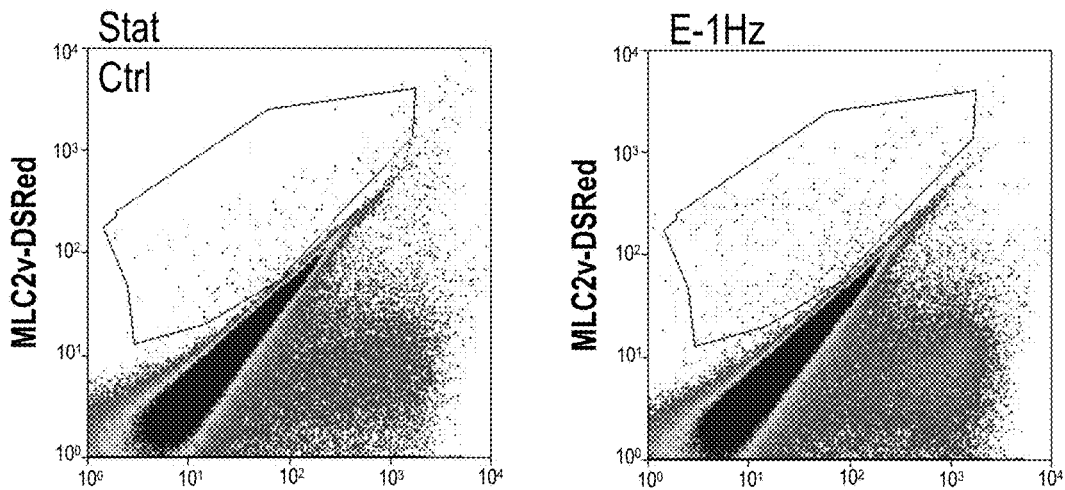
FIGS. 13A and 13B show electrical conditioning increases ventricular phenotype in mESC-CMs.
Figure 13B:
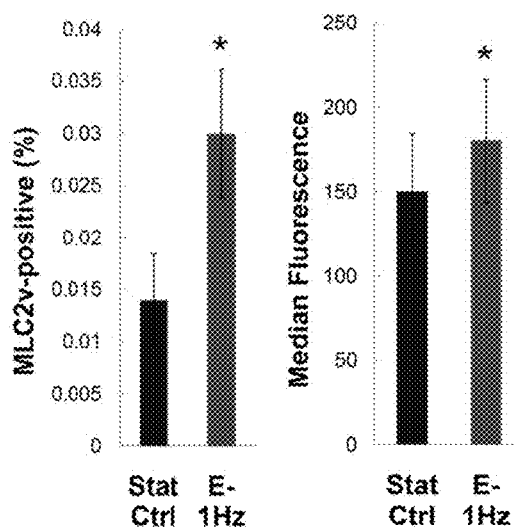

Despite Applicants' achievement of electrical maturation, Ad-Kir2.1-matured CMs continued to exhibit immature $Ca^{2+}$-handling properties with smaller peak $Ca^{2+}$ transient amplitudes and slow kinetics that are comparable to the control group (FIG. 11) (Liu, J. et al. (2007) Stem Cells 25:3038-3044). Indeed, the expression levels of sarcomeric genes, such as MHCα, MHCβ, MLC2a and MLC2v, of the Kir2.1-silenced ddhESC-CMs even became significantly suppressed relative to control ddhESC-CMs (p<0.05; FIG. 4G). Given that sarcomeric proteins of the developing heart are known to respond to changes in contractions (Razeghi, P. et al. (2001) Circulation 104:2923-2931), Applicants' observation could be attributed to the lack of spontaneous beating activities of ddhESC-CMs in culture after Kir2.1-induced cessation of active contractions, which in turn led to the down-regulation of the contractile apparatus. Indeed in developing neurons, Kir2.1 expression can alter their excitability by escalating in response to extrinsic excitation via an activity-dependent mechanism to mediate synaptic plasticity (Razeghi, P. et al. (2001) Circulation 104:2923-2931; Burrone, J. et al. (2002) Nature 420:414-418). To test if electrical activity likewise affects Kir2.1 expression in developing ddhESC-CMs, Applicants' cells mimicked endogenous pacing of adult heart by systematically field-stimulating cells in culture with electrical pulse of 2.5 V/cm at 5 msec pulse duration and 1 Hz frequency for 14 days. Applicants hypothesized that 1) electrical conditioning of ddhESCCMs suffices to promote in vitro electrophysiological maturation, and that 2) the pacing-induced regular contractions can facilitate maturation of $Ca^{2+}$-handling and contractile properties in a manner similar to the fetal heart development. Applicants' experiments showed that this was indeed the case. Both electrically conditioned ventricular and atrial ddhESC-CMs were 100% quiescent with absence of phase 4-depolarization (FIG. 6A, arrows; n=11). Moreover, the RMPs of the atrial and ventricular ddhESC-CMs were significantly hyperpolarized (p<0.05). Such a mature AP phenotype was never observed in >150 time-matched un-stimulated control hESC-CMs that Applicants had recorded. Consistently, Kir2.1 expression became elevated (FIG. 6A). Compared to unpaced controls, electrical conditioning similarly augmented both the electrically induced $Ca^{2+}$ transient amplitude (FIG. 6B; p<0.05) and sarcoplasmic reticulum $Ca^{2+}$ load as shown by caffeine induced $Ca^{2+}$ transients (FIG. 6C; p<0.05) of ddhESC-CMs. Consistently, the expression levels of $Ca^{2+}$-handling proteins typically present in adult CMs but absent or barely expressed in hESC-CMs such as calsequestrin (CSQ), junctin (Jct), and triadin (Trdn) (Liu, J. et al. (2007) Stem Cells 25:3038-3044) as well as the t-tubule biogenesis proteins caveolin-3 (Cav3) and amphiphysin-2 (Amp2) all increased (FIGS. 6D-6E). Consistent with an increase of ddhESC-CMs with maturing ventricular phenotype, electrical conditioning also resulted in a decrease of the atrial natriuretic factor (ANF) (FIG. 6E). More importantly, the contractile proteins MHCα, MHCβ, MLC2a and MLC2v of electrically conditioned ddhESC-CMs were significantly up-regulated (FIG. 6F) relative to the control cells. In addition, the myofilaments became consistently more structured and organized as shown by transmission electron microscopy (TEM) (FIG. 6G, FIGS. 12A and 12B for high resolution images), signifying contractile maturation. The increase in electrical conditioning-induced MLC2v expression could be attributed to a ~43% increase in the number of ventricular CMs as assessed by the number of MLC2v-positive cells relative to the tropomyosin-positive cells using a laser scanning cytometer. Similar to human cells, electrical conditioning likewise increased the expression of MLC2v and the ventricular derivatives in mESC-CMs as demonstrated by flow cytometric analysis of lentivirus generated EFla-GFP-MLC2v-DsRed mESC line where ventricular CMs were identified by their expression of DsRed under the MLC2v promoter (FIGS. 13A and 13B).

Figure 7A:
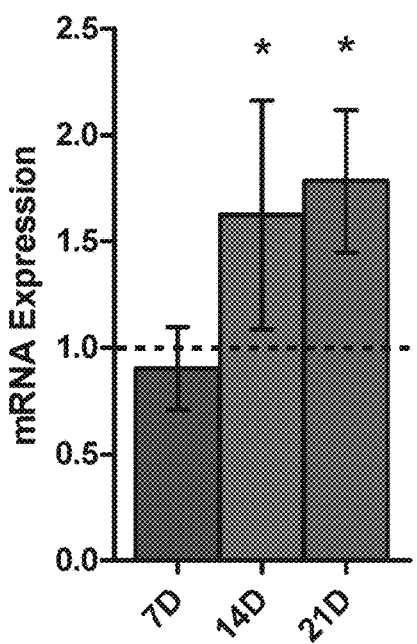
FIG. 7A shows effect of the duration (7, 14 and 21 days) of electrical stimulation at 1 Hz on Kir2.1 expression. Transcript expression normalized to GAPDH, and normalized to time-matched non-stimulated control (broken line) (n=9, from 3 independent batches).
Figure 7B:
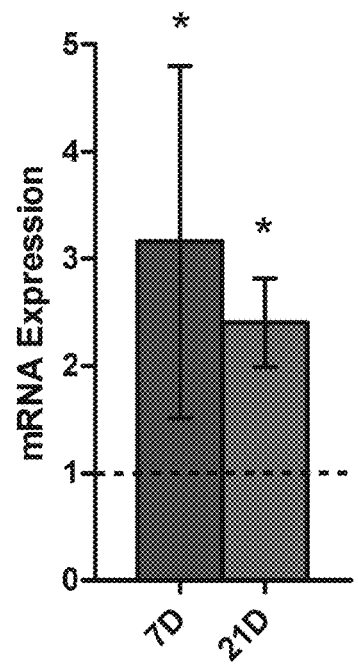
FIG. 7B shows effect of the duration as in FIG. 7A, but performed on later-stage (40-50 days old) hESC-CMs.
Figure 7C:
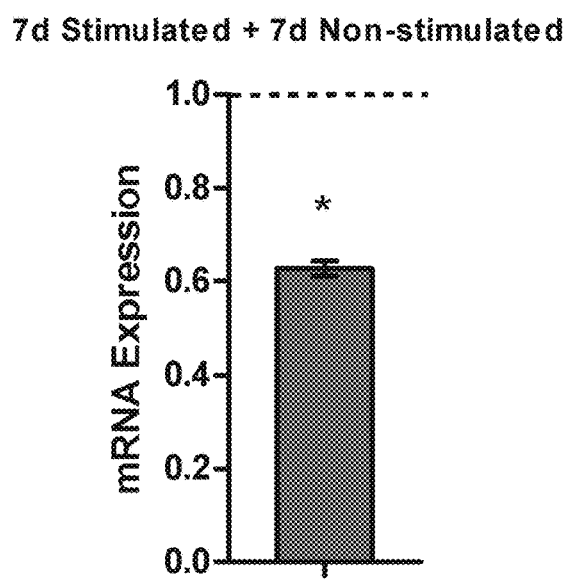
FIG. 7C shows effect of cessation of electrical conditioning of early-stage ddhESC-CMs. Broken line indicates the level of continuous stimulation over the same period.
Figure 7D:
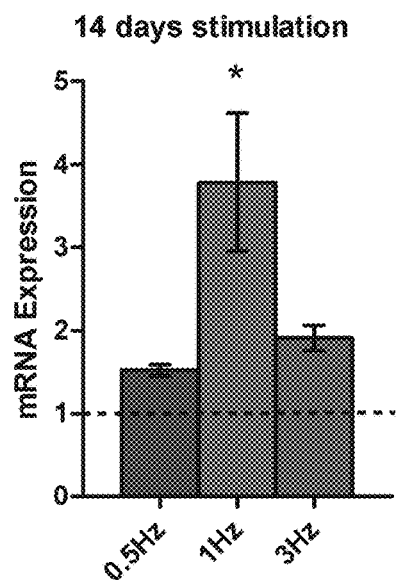
FIG. 7D shows the effect of frequency.

Time-, Aage- and Frequency-Dependence of the Pro-Maturation Effect of Electrical Conditioning Applicants investigated the roles of the duration of cell exposure to field stimulation, age of hESC-VCMs when subjected to electrical conditioning and stimulation frequency (0.5 Hz-2 Hz) in the pro-maturation effect of electrical conditioning on hESC-VCMs. When compared to day 0 control, Kir2.1 expression of early-stage (20-25 days old) hESC-CMs was not different after electrical stimulation (at 1 Hz) for 7 days but became time-dependently increased at day 14 and further elevated at day 21 by ~1.7-fold (FIG. 7A). When stimulated at 1 Hz, later-stage (40-50 days old) hESC-CMs displayed ~3-fold higher expression levels but such increases were not statistically different between days 7 and 21, unlike the early-stage counterpart (FIG. 7B). FIG. 7C shows that when pacing of early-stage hESC-CMs was ceased after stimulating for 14 days, Kir2.1 expression declined after 7 days, indicating that continuous stimulation was needed to maintain or augment the gained expression. Furthermore, electrical conditioning at 1 Hz of early-stage hESC-CMs for 14 days led to 2.3- and 1.9-fold higher Kir2.1 expression than 0.5 and 3 Hz, respectively. Collectively, these results indicate that our mechanism-based approach sufficed to induce maturation in ddhESC-derived CMs.

Discussion

Although conceptually promising as an unlimited source, a number of fundamental hurdles need to be overcome before the use of derived CMs from hESCs or patient-specific iPSCs for clinical and other applications can be realized. It is well accepted that hESC-CMs are electrophysiologically immature, but the underlying mechanisms remain largely unknown. Indeed, multiple ionic currents in hESC-CMs behave differently from those of adult. In this study, various pluripotent stem cell line-derived CMs were investigated as well as different methods of cardiogenic differentiation methods. This data collectively demonstrate that the observed immature electrophysiological properties are independent of the specific pluripotent stem cell types and lines, differentiation protocols as well as species, suggesting that a crucial environmental cue might be missing in the in vitro culturing system thereby leading to the artifactual developmental arrest.

Critical Role of $I_{K1}$ in the Maturation of hESC-CMs

For maintaining an electrophysiologically stable phenotype with a hyperpolarized resting membrane potential close to the reversal potential of $K^+$, an $I_{K1}$ magnitude of at least 50% that of adult ventricular CMs is required. Although the $I_{K1}$ magnitude of hESC-CMs has been shown to increase with prolonged culture of 100 days post-differentiation (Sartiani, L. et al. (2007) Stem Cells 25:1136-1144), the current density in these aged cells is still below the threshold for attaining a mature ventricular electrical phenotype (Bailly, P. et al. (1998) Circulation 98:2753-2759). Therefore, it is impractical to maintain the cells for more than 100 days to achieve only a slight, if not entirely insignificant, improvement for clinical and other applications. One goal of the present study is to design strategies to effectively drive their maturation. By first exploring the basis that underlies the observed electrophysiological immaturities, Applicants identified the lack of $I_{K1}$ as one of the major mechanistic contributors of cellular automaticity. Forced expression of Kir2.1 channels in hESC-CMs alone sufficed to completely eliminate all the immature and proarrhythmic traits and thereby reproducing the adult AP phenotype. Although Ad-Kir2.1-matured hESC-CMs "corrected" automaticity immaturity, these cells continued to exhibit immature $Ca^{2+}$-handling properties. Moreover, these quiescent cells have reduced expression of contractile proteins, MHCα, MHCβ, MLC2a and MLC2v, as quantified by qPCR.

Mechanisms Underlying the Increased Maturation by Electrical Stimulation

Considering the data and the tight E-C coupling between electrophysiological and $Ca^{2+}$-handling properties, Applicants hypothesized that rhythmic electrical conditioning of hESC-CMs in vitro to mimic endogenous pacing may achieve E-C maturation through: 1) chronic pacing with field-stimulation may induce ion channel expression changes, 2) pacing-induced active contractions of electrically silenced hESC-CMs with mature APs can in turn facilitate $Ca^{2+}$-handling and contractile maturation in a manner similar to the normal fetal heart development. Of note, although immature hESC-CMs do spontaneously fire APs and contract and without being bound by theory, Applicants submit that these activities may be too weak, unsustained and sporadic in comparison to the physiological levels for effective facilitation of maturation in vitro. Electrical conditioning robustly led to many aspects of cellular maturation of hESC-CMs, including electrophysiological maturation without phase 4-depolarization similar to Kir2.1 gene transfer, $Ca^{2+}$-handing maturation with increased peak $Ca^{2+}$ transient amplitude and SR $Ca^{2+}$ load, structured organization of myofilaments as well as an up-regulation of contractile and t-tubule biogenesis proteins. Although the short-term electrical conditioning did mature numerous aspects of CM functions relative to control, the resting membrane potential of electrically conditioned ventricular ddhESC-CMs is still about 10 mV more depolarized, with smaller peak $Ca^{2+}$ transient amplitude and slower kinetics, than that of adult ventricular CMs. Future studies will be required to optimize physical parameters of electrical conditioning such as the voltage pulse, pulse duration and frequency for maximized facilitating effect.

These observations were qualitatively similar in some ways to what have been observed in rodent CMs. For instance, neonatal rat and ESC-like P19 mouse embryonic carcinoma cell (ECC)-derived CMs stimulated to actively contract by pulsed electric field can self-align sarcomeres leading to improved contractility (Au, H. T. H. et al. (2007) Biomaterials 28(29):4277-4293; Radisic, M. et al. (2004) Proc. Nat. Acad. Sci. USA 101:18129-18134). Without being bound by theory, Applicants speculate that the rhythmic field-stimulations of hESC-CMs that otherwise intrinsically beat at low and/or irregular frequency may result in cyclic increase in intracellular $Ca^{2+}$ concentration, which can increase their averaged $Ca^{2+}$ residence time. Such an increase in intracellular $Ca^{2+}$ may in turn contribute to the maturation effect observed via the second messenger system (e.g., by activating the calcineurin-NFAT pathway) (Kassiri, Z. et al. (2002) Circulation Research 90:578-585; Lammerding, J. et al. (2004) Annals of the New York Academy of Sciences 1015:53-70; Lebeche, D. et al. (2004) Circulation 110:3435-3443; Zobel, C. et al. (2002) Circulation 106: 2385-2391).

Significance of Cell Maturation In Vitro Prior to Transplantation

More immature stem cell-derived CMs has been suggested to be more ischemic-resistant and tolerant to the hypoxic environment after transplantation (Boheler, K. R. et al. (2011) Stem Cells Int. 2011:214203). The in vivo environment has also been demonstrated to induce electrophysiological maturation of immature CMs comparable to the host cells after transplantation but only for those that have fully integrated with the host cells (Halbach, M. et al. (2007) Circ Res. 101:484-492). Those transplanted CMs without electrical coupling remains electrophysiologcially immature, which can be arrhythmogenic as demonstrated herein. Therefore, it is also imperative to find a balance between safety and efficacy by defining what maturation status is best for in vivo transplantation since immature and mature hESC-CMs likely respond differently to ischemic and hypoxic environment. Eliminating intrinsic triggers for arrhythmia of the hESC-CMs to ensure no additional electrophysiological complications from their presence is of critical importance. The safety of these cells must be addressed before pondering their potential benefits to the recipient.

The strategy reported here, developed by first obtaining an understanding of the cellular differences and the underlying mechanisms, offers a simple non-genetic way to facilitate the E-C maturation of otherwise developmentally arrested derived CMs, thereby eliminating significant undesirable immature pro-arrhythmogenic traits. Furthermore, the successful use of derived CMs as human heart disease models and cardiotoxicity screening tools depends on their ability to recapitulate the properties of their adult counterparts. In combination with other advances in directed differentiation and cardiovascular progenitor identification (Yang, L. et al. (2008) Nature 453:524-528; Bu, L. et al. (2009) Nature 460:113-117; Moretti, A. et al. (2006) Cell 127:1151-1165), this approach can facilitate the clinical translation and enable more accurate human heart disease modeling, drug discovery and cardiotoxicity screening. The modified cells of this disclosure have no native counterparts in the body; their cardiac derivatives and the modified cells as described herein are also not identical (e.g., smaller in size, Ca transient properties are different, certain key cardiac genes are differentially expressed) to what are seen in nature.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A method for inducing an electrophysiologically mature phenotype in a human cell that is not electrophysiologically mature, the method comprising administering to the human cell an effective amount of electrical pacing, thereby inducing the electrophysiologically mature phenotype in the human cell,
wherein the human cell that is not electrophysiologically mature is a ventricular cell or an atrial cell that is characterized by having one or more of the following features: (a) repetitive firing, (b) spontaneous firing, (c) phase 4 depolarization, (d) a resting membrane potential or maximum diastolic potential more positive than −80 mV, and (f) delayed after-depolarization;
wherein the effective amount of electrical pacing comprises a pulsed electrical current of from about 2.0 to about 3.0 volts/cm (v/cm) for about 2 millisecond (msec) to about 8 msec, at a frequency of about 0.5 Hertz (HZ) to about 1.5 HZ; and
wherein the electrophysiologically mature phenotype is characterized by the human cell having one or more of the following features: (i) quiescent-yet-excitable, (ii) absence of phase 4 depolarization, and (iii) absence of spontaneous firing, and (iv) a resting membrane potential more negative than −65 mV, wherein the method excludes expression of recombinant Kir2.1 in the cell to enhance or increase Kir2.1 expression and wherein Kir2.1 expression becomes elevated.

2. A method for preparing an electrophysiologically mature cardiomyocyte from a human cell that is not electrophysiologically mature, comprising administering to the human cell an effective amount of electrical pacing, thereby preparing an electrophysiologically mature cardiomyocyte,
wherein the human cell that is not electrophysiologically mature is a ventricular cell or an atrial cell that is characterized by having one or more of the following features: (a) repetitive firing, (b) spontaneous firing, (c) phase 4 depolarization, (d) a resting membrane potential or maximum diastolic potential more positive than −80 mV, and (f) delayed after-depolarization;
wherein the effective amount of electrical pacing comprises a pulsed electrical current of from about 2.0 to about 3.0 volts/cm (v/cm) for about 2 millisecond (msec) to about 8 msec, at a frequency of about 0.5 Hertz (HZ) to about 1.5 HZ;
wherein the electrophysiologically mature cardiomyocyte is characterized by one or more of the following features: (i) quiescent-yet-excitable, (ii) absence of phase 4 depolarization, and (iii) absence of spontaneous firing, and (iv) a resting membrane potential more negative than −80 mV, wherein the method excludes expression of recombinant Kir2.1 in the cell to enhance or increase Kir2.1 expression and wherein Kir2.1 expression becomes elevated.

3. The method of claim 1, wherein the human cell is derived from one or more of an embryonic stem cell, a pluripotent stem cell, an embryoid body, a mesodermal cardiosphere or an induced pluripotent stem cell.

4. The method of claim 2, wherein the electrophysiologically mature cardiomyocyte produced by the method is further characterized by increased expression of one or more contractile proteins of the group consisting of myosin heavy chain alpha (MHCα), myosin heavy chain beta (MHCβ), myosin light chain alpha2a (MLC2a), myosin light chain alpha2v (MLC2v), and cardiac ion channel pump proteins, relative to expression in the cell that is not electrophysiologically mature prior to application of the method.

5. The method of claim 1, wherein the electrophysiologically mature phenotype is further characterized by increased expression of one or more contractile proteins of the group consisting of myosin heavy chain alpha (MHCα), myosin heavy chain beta (MHCβ), myosin light chain alpha2a (MLC2a), myosin light chain alpha2v (MLC2v), and cardiac ion channel pump proteins, relative to expression in the cell prior to application of the method.

6. The method of claim 1 or 2, wherein the effective amount of electrical pacing is administered for a duration of 1 day to 4 weeks.

7. The method of claim 5, wherein the effective amount of electrical pacing is administered for a duration of 7 days to 21 days.

8. The method of claim 5, wherein the effective amount of electrical pacing is administered for a duration of 14 days to 4 weeks.

* * * * *